(12) United States Patent
Rubin

(10) Patent No.: US 11,904,076 B2
(45) Date of Patent: Feb. 20, 2024

(54) AIR PURIFYING APPARATUS, METHOD AND SYSTEM

(71) Applicant: AIR SANZ HOLDINGS PTY LTD, South Melbourne (AU)

(72) Inventor: Richard Harold Rubin, South Melbourne (AU)

(73) Assignee: AIR SANZ HOLDINGS PTY LTD, South Melbourne (AU)

( * ) Notice: Subject to any disclaimer, the term of this patent is extended or adjusted under 35 U.S.C. 154(b) by 1252 days.

(21) Appl. No.: 16/382,547

(22) Filed: Apr. 12, 2019

(65) Prior Publication Data
US 2019/0231918 A1 Aug. 1, 2019

Related U.S. Application Data

(62) Division of application No. 14/390,092, filed as application No. PCT/AU2013/000268 on Mar. 15, 2013, now abandoned.

(30) Foreign Application Priority Data

Apr. 2, 2012 (AU) .................................. 2012901314

(51) Int. Cl.
*A61L 9/12* (2006.01)
*B01D 46/00* (2022.01)
(Continued)

(52) U.S. Cl.
CPC ................. *A61L 9/122* (2013.01); *A61L 2/18* (2013.01); *A61L 9/04* (2013.01); *A61L 9/127* (2013.01);
(Continued)

(58) Field of Classification Search
CPC ............. A61L 9/122; A61L 9/127; A61L 9/04
See application file for complete search history.

(56) References Cited

U.S. PATENT DOCUMENTS

| 6,645,429 B1 * | 11/2003 | Raniwala | .............. B65B 55/027 |
| | | | 422/305 |
| 2007/0157817 A1 * | 7/2007 | Lee | ........................ B01D 47/14 |
| | | | 96/294 |

(Continued)

*Primary Examiner* — Donald R Spamer
(74) *Attorney, Agent, or Firm* — B. Aaron Schulman, Esq.; Stites & Harbison, PLLC

(57) ABSTRACT

A human-activity-environment air-purifying apparatus is provided that draws in airflow from an ambient environment, kills germs in the airflow within the apparatus and expels purified airflow back into the environment. The apparatus has a housing with an interior chamber. An airflow enters the chamber through an inlet. From the interior chamber, the airflow is expelled through an outlet. The apparatus has a germ-killing-system that kills germs in the airflow and has an airflow-generator which causes the airflow to flow from the inlet to the outlet. In one aspect, the apparatus has a three-dimensional filter structure that has air-filter-surfaces that define a filter interior region and encompassed by the air-filter-surfaces of the filter structure. The filter is positioned in connection with the inlet so that airflow entering the inlet is dispersed into the housing interior chamber in multiple directions exclusively through the air-filter-surfaces of the three-dimensional filter structure.

17 Claims, 38 Drawing Sheets

(51) Int. Cl.
    *A61L 9/04* (2006.01)
    *A61L 2/18* (2006.01)
    *A61L 9/14* (2006.01)
    *B01D 46/24* (2006.01)
    *B01D 46/52* (2006.01)
    *F24F 8/158* (2021.01)
    *B01D 46/62* (2022.01)
    *F24F 8/24* (2021.01)

(52) U.S. Cl.
    CPC ............ *A61L 9/14* (2013.01); *B01D 46/0028* (2013.01); *B01D 46/2411* (2013.01); *B01D 46/521* (2013.01); *B01D 46/62* (2022.01); *F24F 8/158* (2021.01); *A61L 2209/111* (2013.01); *A61L 2209/133* (2013.01); *A61L 2209/14* (2013.01); *B01D 2275/10* (2013.01); *B01D 2275/205* (2013.01); *B01D 2275/208* (2013.01); *F24F 8/24* (2021.01)

(56) References Cited

U.S. PATENT DOCUMENTS

| | | | |
|---|---|---|---|
| 2008/0019861 A1* | 1/2008 | Silderhuis | F24F 8/192 422/4 |
| 2010/0247404 A1* | 9/2010 | Ptak | B01D 46/10 55/486 |

* cited by examiner

AIR PURIFYING APPARATUS, METHOD AND SYSTEM

CROSS-REFERENCE TO RELATED APPLICATIONS

This application is a divisional of U.S. patent application Ser. No. 14/390,092, having a filing date of Oct. 2, 2014, which is a 371 application of International Application PCT/AU2013/000268, filed Mar. 15, 2013, and which claims the benefit of priority application AU 2012901314 filed Apr. 2, 2012, all of said applications incorporated herein by reference.

FIELD OF INVENTION

The present invention relates to improvement in apparatus which draw in an airflow from an ambient human-activity environment, kill germs in the airflow, then expel the purified air from the apparatus back into the ambient environment.

The present invention relates particularly to hand dryers, hand sanitizers, air purifiers and other apparatus that include an air purifier such as vacuum cleaning apparatus.

BACKGROUND

Human-activity environments, which are frequented by people, tend to be conducive for spreading germs and particularly disease-causing viruses among the people intermingling in the human-activity environment.

Moreover, there is constant change in the variety of viruses that circulate through a human population in any particular season of time. Each year, there are new strains of viruses which are different from the strains from previous seasons. Thus, anti-virus substances, designed to counteract earlier variants, may not be as effective against strains that emerge in the new season.

When some anti-virus substances are manufactured to be of sufficient strength to kill certain viruses, a side effect is that the strength of those antivirus substances can also inadvertently pose a health risk to humans. There are germ-killing substances, adapted to be harmful to germs, that are also toxic to humans. For example, substances that are able to kill virulent airborne viruses, such as H1N1 virus, may also be toxic to humans or can at least instigate harmful side effects in humans. For example, the substances, intended to kill the germs, could at the same time trigger allergic reactions in humans.

For apparatus that are designed to draw in airflow from ambient human-activity environments, such apparatus may inadvertently become collectors and breeding sites for germs. For example, electric hand dryers, that are installed in toilets, can draw in germs from the ambient atmosphere of the toilet.

In the prior art, in such apparatus that draw in an airflow, it is known to provide filters that are impregnated with antivirus substances. The present inventor's earlier International Application No. PCT/AU2005/001803 (Rubin) required airflow in a hand dryer housing to pass through several sheets of flat filter material, where the filters are arranged in series, one filter after the other. In other words, all the airflow inside the hand dryer housing had to be forced through this series of small sheets of filters. This required a fan with a powerful fan-motor to generate airflow of sufficient force to enable the airflow to flow through the sequence of sheets of filters. In practice, use of a more powerful fan-motor can result in higher noise levels generated from within the hand dryer housing.

Faced with the need of generating more powerful airflow through the germ-killing apparatus, a known approach has been to focus on achieving improvements in fan-motor design in order to provide stronger and more powerful fan-motors. Thus, the more powerful fan-motors, while creating more powerful airflow, can inadvertently lead to problems associated with the higher levels of noise in the human activity environment. In the prior art, an approach to the problem of high fan-motor noise is to improve the electrical and/or mechanical design of the fan-motors in an attempt to reduce emitted noise, while maintaining the amount of power required for fast airflow through such apparatus.

Another problem in known hand dryers is that the time needed to dry a user's hands can be substantially longer compared to, say, the user drying their hands with towel.

Another problem in known hand dryers and air purifiers, which draw in and expel the airflow, is that over time a large degree of build-up of grime from the airflow builds up on external surfaces of the apparatus were the airflow enters and leaves. FIGS. 19A and 19B are underside views of examples of known hand dryers attached to a wall 3. Over time, such known hand dryers experience build-up of grime on the undersides of the apparatus, as view in FIGS. 19A and 19B.

An object of the present invention is to overcome or at least ameliorate one or more of the problems, or to provide an improved alternative.

This specification and its description contains several inventive aspects, and it is not intended that each and every inventive aspect should be able to solve each and every one of the above problems. Rather, each inventive aspect is able to overcome or at least ameliorate at least one or more problems.

Any discussion of prior art above and herein in this specification, either singly or in combination, is not to be construed as an admission of the state of common general knowledge of the skilled addressee.

SUMMARY OF INVENTION

The present specification contains several aspects of the present invention:

According to a first aspect of the present invention, there is provided a human-activity-environment air-purifying apparatus that draws in an airflow from an ambient human-activity-environment, kills germs in the airflow within the apparatus and expels the airflow purified back into the human-activity-environment, the apparatus comprising:
- a housing having an interior chamber into which an airflow enters through an inlet and from which interior chamber the airflow is expelled through an outlet;
- an airflow-germ-killing-system adapted to kill germs in the airflow;
- an airflow-generator which causes the airflow to flow from the inlet to the outlet;
- wherein the inlet includes multiple inlet apertures that are arranged, when in use mounted on a wall, to each draw in part of any incoming airflow from a different direction relative to other of the multiple inlets.

When mounted on the wall, the apparatus may have a central axis, and preferably each of the inlet apertures has a plane that defines a front face of its opening, and wherein the plane of one of the inlet apertures preferably is not co-planar with the plane of the other of the inlet apertures.

Preferably, the respective planes of each of the apertures are not perpendicular to the central axis in order that the face of each inlet aperture points away from the central axis and not directly downwards in the direction of the central axis.

Preferably, the multiple inlet apertures are able, in use, to each draw in part of any incoming airflow in a lateral direction relative to the central axis.

Preferably, the inlet includes two inlet apertures that draw in the incoming airflow laterally from the right hand side and left hand side of the central axis.

According to a second aspect of the present invention, there is provided a human-activity-environment air-purifying apparatus that draws in an airflow from an ambient human-activity-environment, kills germs in the airflow within the apparatus and expels the airflow purified back into the human-activity-environment, the apparatus comprising:
- a housing having an interior chamber into which an airflow enters through an inlet and from which interior chamber the airflow is expelled through an outlet;
- an airflow-germ-killing-system adapted to kill germs in the airflow;
- an airflow-generator which causes the airflow to flow from the inlet to the outlet;
- wherein the airflow-germ-killing-system includes a three-dimensional filter structure comprising air-filter-surfaces that define a filter interior region therein and encompassed by the air-filter-surfaces of the filter structure, the encompassed filter interior region, in use, positioned in connection with the inlet so that airflow entering the inlet is dispersed into the housing interior chamber in multiple directions exclusively through the air-filter-surfaces of the three-dimensional filter structure.

The three-dimensional filter structure may be formed as a container or a box with one side fully opened The air-filter-surfaces may include wall-structure and ceiling-structure.

The air-filter-surfaces may comprise a non-flat surface structure.

The air-filter-surfaces may comprise a multi-faceted surface structure having a pleated or corrugated structure.

The air-filter-surfaces may comprise multiple layers of different filter material, and wherein the multiple layers of the air-filter-surfaces may comprise a sequence of layers from nearest to the filter interior region to furthest from the filter interior region as follows:
i) a germ-killing filter layer that carries germ-killing-substance; and
ii) a germ-killing-substance interception filter layer that intercepts or substantially intercepts the germ-killing-substance.

The sequence of layers from nearest to the filter interior region to furthest from the filter interior region may comprise:
i) said germ-killing filter layer that carries germ-killing-substance; and
ii) said germ-killing-substance interception filter layer that intercepts or substantially intercepts the germ-killing-substance, and
iii) a material entrapment layer that entraps at least any filter material that come from said germ-killing filter layer and said germ-killing-substance interception filter layer.

The germ-killing-substance interception filter layer may include charcoal or carbon.

The material entrapment layer may include anti-fibre-migration filter material that is able to entrap material that has potential to cause nasal irritation or allergies in humans.

The airflow-germ-killing-system may comprise germ-killing-substance positioner that is able to position one or more sources of one or more air-diffusible germ-killing-substances inside the filter interior region that air-diffuse the germ-killing-substances upon engagement with any airflow in the filter interior region.

Each of the one or more sources before air-diffusion occurs may be initially in the form of a solid or gel.

The airflow-germ-killing-system may include a wick-delivery-system that includes a wick mechanism able to effuse into the airflow within the apparatus a germ-killing-liquid-substance stored in a replaceable container.

The wick-delivery-system may include a filter holder that is able to support the wick mechanism and also a further germ-killing-substance interception filter layer that intercepts the germ-killing-liquid-substance that effuses from the wick mechanism.

The filter holder may also be able to support a further material entrapment layer that entraps at least any filter material that comes from said further germ-killing-substance interception filter layer.

The filter holder may include one or more side apertures adapted to allow, in use, a portion of the airflow to enter the filter holder through the one or more side apertures so as to pass across a face of the further filter layer while, in use, another portion of the airflow enters through the further filter layer, such that the passage of airflow through the one or more side apertures serves to draw the airflow through the further filter layer.

The apparatus may include airflow-path-size-alterable arrangement that enables adjustment of the size of at least part of a path that the airflow takes within the apparatus.

The airflow-generator may include a fan in a fan-housing and may also include a motor in a motor-housing, said part of the path that the airflow takes includes a gap between the fan-housing and the motor-housing, and wherein the airflow-path-size-alterable arrangement may be able to allow adjustment of the gap in order to alter any airflow through the gap.

The airflow-germ-killing-system may include a germ-killing-substance-sprayer that sprays germ-killing-liquid-substance into the airflow at a location where, in use, the germ-killing-liquid-substance does not coat onto surfaces of the apparatus itself.

The germ-killing-substance-sprayer may be arranged to spray the germ-killing-liquid-substance into the airflow at a point where, in use, the airflow has already exited the apparatus so as not to coat onto surfaces of the apparatus itself.

The germ-killing-substance-sprayer may have a spray-outlet in the form of an arrangement of several atomizer spray ducts which are arranged on a duct-support, each of the spray ducts arranged to spray liquid in a different direction.

The duct-support may be able to be rotated as spray is emitted from its spray ducts.

The duct-support may have a direction of rotation that is able to be intermittently and periodically changed from clockwise to anti-clockwise.

According to a third aspect of the present invention, there is provided use of an apparatus, according to the 2nd aspect of the invention, wherein an anti-germ substance used in or inside the three-dimensional filter structure is substantially toxic to humans, and any anti-germ substance used elsewhere in the filter interior region, airflow path and outside of the three-dimensional filter structure is substantially non-toxic to humans.

According to a fourth aspect of the present invention, there is provided a method of using an apparatus according to 2nd aspect, wherein an anti-germ substance used in or inside the three-dimensional filter structure is substantially toxic to humans, and any anti-germ substance used elsewhere in the filter interior region, airflow path and outside of the three-dimensional filter structure is substantially non-toxic to humans.

According to a fifth aspect of the present invention, there is provided an airflow-germ-killing-system-filter adapted to be used in a human-activity-environment air-purifying apparatus that draws in an airflow from an ambient human-activity-environment, kills germs in the airflow within the apparatus and expels the airflow purified back into the human-activity-environment, the apparatus comprising:
 a housing having an interior chamber into which an airflow enters through an inlet and from which interior chamber the airflow is expelled through an outlet;
 an airflow-germ-killing-system adapted to kill germs in the airflow;
 an airflow-generator which causes the airflow to flow from the inlet to the outlet;
 wherein the airflow-germ-killing-system-filter comprises a three-dimensional filter structure having air-filter-surfaces that define a filter interior region therein and encompassed by the air-filter-surfaces of the filter structure, the encompassed filter interior region, in use, positioned in connection with the inlet so that airflow entering the inlet is dispersed into the housing interior chamber in multiple directions exclusively through the air-filter-surfaces of the three-dimensional filter structure.

The three-dimensional filter structure may be formed as a container or a box with one side fully opened.

The air-filter-surfaces may include wall-structure and ceiling-structure.

The air-filter-surfaces may comprise a non-flat surface structure.

The air-filter-surfaces may comprise a multi-faceted surface structure having a pleated or corrugated structure.

The air-filter-surfaces may comprise multiple layers of different filter material, and wherein the multiple layers of the air-filter-surfaces may comprise a sequence of layers from nearest to the filter interior region to furthest from the filter interior region as follows:
 i) a germ-killing filter layer that carries germ-killing-substance; and
 ii) a germ-killing-substance interception filter layer that intercepts or substantially intercepts the germ-killing-substance.

The sequence of layers from nearest to the filter interior region to furthest from the filter interior region may comprise:
 i) said germ-killing filter layer that carries germ-killing-substance; and
 ii) said germ-killing-substance interception filter layer that intercepts or substantially intercepts the germ-killing-substance, and
 iii) a material entrapment layer that entraps at least any filter material that come from said germ-killing filter layer and said germ-killing-substance interception filter layer.

The germ-killing-substance interception filter layer may include charcoal or carbon.

According to a sixth aspect of the present invention, there is provided a human-activity-environment air-purifying apparatus that draws in an airflow from an ambient human-activity-environment, kills germs in the airflow within the apparatus and expels the airflow purified back into the human-activity-environment, the apparatus comprising:
 a housing having an interior chamber into which an airflow enters through an inlet and from which interior chamber the airflow is expelled through an outlet;
 an airflow-germ-killing-system adapted to kill germs in the airflow;
 an airflow-generator which causes the airflow to flow from the inlet to the outlet;
 wherein the apparatus has an underside and a base-mounting adapted to be attached to a wall, and wherein both the inlet and the outlet are on the underside of the apparatus such that the inlet is not between the outlet and the base-mounting.

The inlet and outlet may be arranged on the underside generally in a row or sequence where the direction of the row or sequence is generally alongside the base-mounting.

On the surface where the outlet and inlet are positioned, the inlet may occupy a very substantial portion of said surface that is outside the outgoing-airflow-protected-surface-region.

According to a seventh aspect of the present invention, there is provided a vacuum cleaner air-purifying apparatus that draws in an airflow from an ambient human-activity-environment, kills germs in the airflow within the apparatus and expels the airflow purified back into the human-activity-environment, the apparatus comprising:
 a housing having an interior chamber into which an airflow enters through an inlet and from which interior chamber the airflow is expelled through an outlet;
 an airflow-germ-killing-system adapted to kill germs in the airflow;
 an airflow-generator which causes the airflow to flow from the inlet to the outlet;
 wherein the airflow-germ-killing-system includes a three-dimensional filter structure comprising air-filter-surfaces that define a filter interior region therein and encompassed by the air-filter-surfaces of the filter structure, the encompassed filter interior region, in use, positioned in connection with a path of the airflow inside the vacuum cleaner so that airflow entering the inlet is dispersed into the housing interior chamber in multiple directions exclusively through the air-filter-surfaces of the three-dimensional filter structure.

According to an eighth aspect of the present invention, there is provided a human-activity-environment air-purifying apparatus that draws in an airflow from an ambient human-activity-environment, kills germs in the airflow within the apparatus and expels the airflow purified back into the human-activity-environment, the apparatus comprising:
 a housing having an interior chamber into which an airflow enters through an inlet and from which interior chamber the airflow is expelled through an outlet;
 an airflow-germ-killing-system adapted to kill germs in the airflow;
 an airflow-generator which causes the airflow to flow from the inlet to the outlet;
 wherein the airflow-germ-killing-system includes a wick-delivery-system that includes a wick mechanism able to effuse into the airflow within the apparatus a germ-killing-liquid-substance stored in a replaceable container.

The wick-delivery-system may include a filter holder that is able to support the wick mechanism and also a further germ-killing-substance interception filter layer that intercepts the germ-killing-liquid-substance that effuses from the wick mechanism.

The filter holder may also be able to support a further material entrapment layer that entraps at least any filter material that comes from said further germ-killing-substance interception filter layer.

The filter holder may include one or more side apertures adapted to allow, in use, a portion of the airflow to enter the filter holder through the one or more side apertures so as to pass across a face of the further filter layer while, in use, another portion of the airflow may enter through the further filter layer, such that the passage of airflow through the one or more side apertures serves to draw the airflow through the further filter layer.

According to a ninth aspect of the present invention, there is provided a human-activity-environment air-purifying apparatus that draws in an airflow from an ambient human-activity-environment, kills germs in the airflow within the apparatus and expels the airflow purified back into the human-activity-environment, the apparatus comprising:
  a housing having an interior chamber into which an airflow enters through an inlet and from which interior chamber the airflow is expelled through an outlet;
  an airflow-germ-killing-system adapted to kill germs in the airflow;
  an airflow-generator which causes the airflow to flow from the inlet to the outlet;
  wherein the apparatus includes airflow-path-size-alterable arrangement that enables adjustment of the size of at least part of a path that the airflow takes within the apparatus.

The airflow-generator may include a fan in a fan-housing and also may include a motor in a motor-housing, said part of the path that the airflow takes includes a gap between the fan-housing and the motor-housing, and wherein the airflow-path-size-alterable arrangement may be able to allow adjustment of the gap in order to alter any airflow through the gap.

According to a tenth aspect of the present invention, there is provided a human-activity-environment air-purifying apparatus that draws in an airflow from an ambient human-activity-environment, kills germs in the airflow within the apparatus and expels the airflow purified back into the human-activity-environment, the apparatus comprising:
  a housing having an interior chamber into which an airflow enters through an inlet and from which interior chamber the airflow is expelled through an outlet;
  an airflow-germ-killing-system adapted to kill germs in the airflow;
  an airflow-generator which causes the airflow to flow from the inlet to the outlet;
  wherein the airflow-germ-killing-system includes a germ-killing-substance-sprayer that is able to spray germ-killing-liquid-substance into the airflow at a location where, in use, the germ-killing-liquid-substance does not coat onto surfaces of the apparatus itself.

The germ-killing-substance-sprayer may be arranged to spray the germ-killing-liquid-substance into the airflow at a point where, in use, the airflow has already exited the apparatus so as not to coat onto surfaces of the apparatus itself.

The germ-killing-substance-sprayer may have a spray-outlet in the form of an arrangement of several atomizer spray ducts which are arranged on a duct-support, each of the spray ducts arranged to spray liquid in a different direction.

The duct-support may be able to be rotated as spray is emitted from its spray ducts.

The duct-support may have a direction of rotation that is able to be intermittently and periodically changed from clockwise to anti-clockwise.

According to an eleventh aspect of the present invention, there is provided a human-activity-environment air-purifying apparatus that draws in an airflow from an ambient human-activity-environment, kills germs in the airflow within the apparatus and expels the airflow purified back into the human-activity-environment, the apparatus comprising:
  a housing having an interior chamber into which an airflow enters through an inlet and from which interior chamber the airflow is expelled through an outlet;
  an airflow-germ-killing-system adapted to kill germs in the airflow;
  an airflow-generator which causes the airflow to flow from the inlet to the outlet;
  wherein the airflow-germ-killing-system includes a germ-killing-substance-sprayer that sprays germ-killing-liquid-substance into the airflow,
  and wherein the germ-killing-liquid-substance comprises at least one antimicrobial agent and a disperser.

The at least one antimicrobial agent may be a quaternary ammonium salt and the disperser may be an alkyl glucoside.

The at least one antimicrobial agent may include a first anti-microbial agent comprising alkyl dimethyl benzyl ammonium chloride and a second anti-microbial agent comprising didecyl dimethyl ammonium chloride.

The ratio between the first and the second antimicrobial agent may be approximately 4:6.

The disperser may include one or more of decylglucoside and octylglucoside.

The disperser may include decylglucoside and octylglucoside in the ratio of approximately 6:5.

The at least one antimicrobial agent may include a third antimicrobial a biguanide.

The biguanide may be a poly-hexamethylene biguanide.

In exemplary embodiments that have a third antimicrobial agent, the ratio of the combination of the first and second antimicrobial agents to the third antimicrobial agent may be approximately 1:1.

The airflow-germ-killing-system may include a three-dimensional filter structure as described above in other aspects of the invention.

According to a twelfth aspect of the present invention, there is provided use of a germ-killing-liquid-substance in a human-activity-environment air-purifying apparatus that draws in an airflow from an ambient human-activity-environment, kills germs in the airflow within the apparatus and expels the airflow purified back into the human-activity-environment, the apparatus comprising:
  a housing having an interior chamber into which an airflow enters through an inlet and from which interior chamber the airflow is expelled through an outlet;
  an airflow-germ-killing-system adapted to kill germs in the airflow;
  an airflow-generator which causes the airflow to flow from the inlet to the outlet;
  wherein the airflow-germ-killing-system includes a germ-killing-substance-sprayer that is able to spray germ-killing-liquid-substance into the airflow, and wherein the germ-killing-liquid-substance comprises at least one antimicrobial agent and a disperser.

According to a thirteenth aspect of the present invention, there is provided a method of spraying at least one antimicrobial agent onto and spreading the agent over a user's hands, the method comprising:

spraying a germ-killing-liquid-substance using a human-activity-environment air-purifying apparatus that draws in an airflow from an ambient human-activity-environment, kills germs in the airflow within the apparatus and expels the airflow purified back into the human-activity-environment, the apparatus comprising:

a housing having an interior chamber into which an airflow enters through an inlet and from which interior chamber the airflow is expelled through an outlet;

an airflow-germ-killing-system adapted to kill germs in the airflow;

an airflow-generator which causes the airflow to flow from the inlet to the outlet;

wherein the airflow-germ-killing-system includes a germ-killing-substance-sprayer that is used to spray the germ-killing-liquid-substance into the airflow, and wherein the germ-killing-liquid-substance comprises at least one antimicrobial agent and a disperser, and wherein the germ-killing-liquid-substance comprises at least one antimicrobial agent and a disperser, and the method includes using the airflow, and the disperser to spread the least one antimicrobial agent across the user's skin of the hands.

BRIEF DESCRIPTION OF THE DRAWING FIGURES

In order that the present invention might be more fully understood, embodiments of each of the aspects of the invention will be described, by way of example only, with reference to the accompanying drawings, in which.

Figure 1:
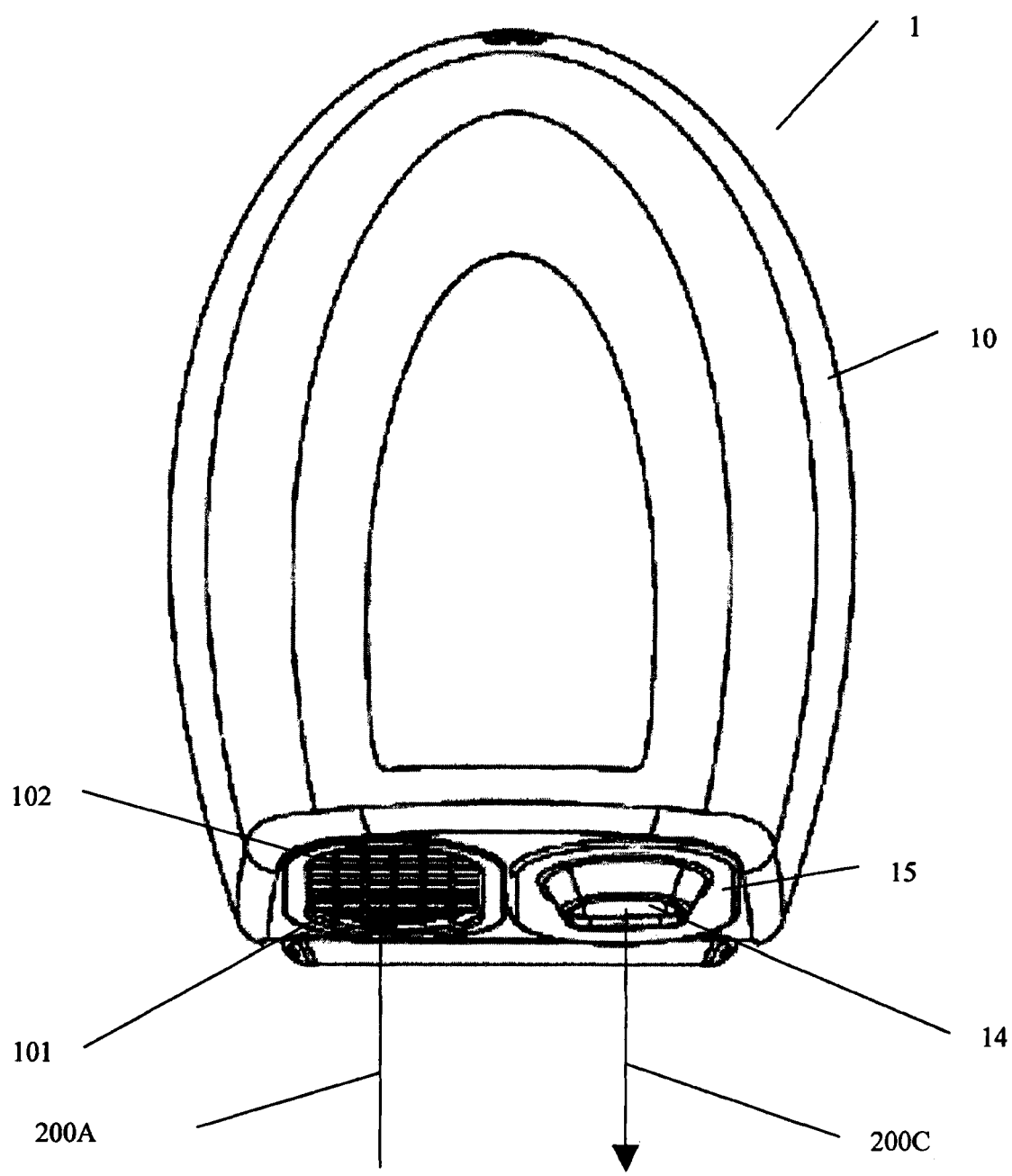
FIG. 1 is a bottom perspective view of an embodiment of an air purifying apparatus in the form of a hand dryer, where the dryer is viewed at an angle from below when the unit is mounted on an upright surface, such as a wall.
Figure 4:
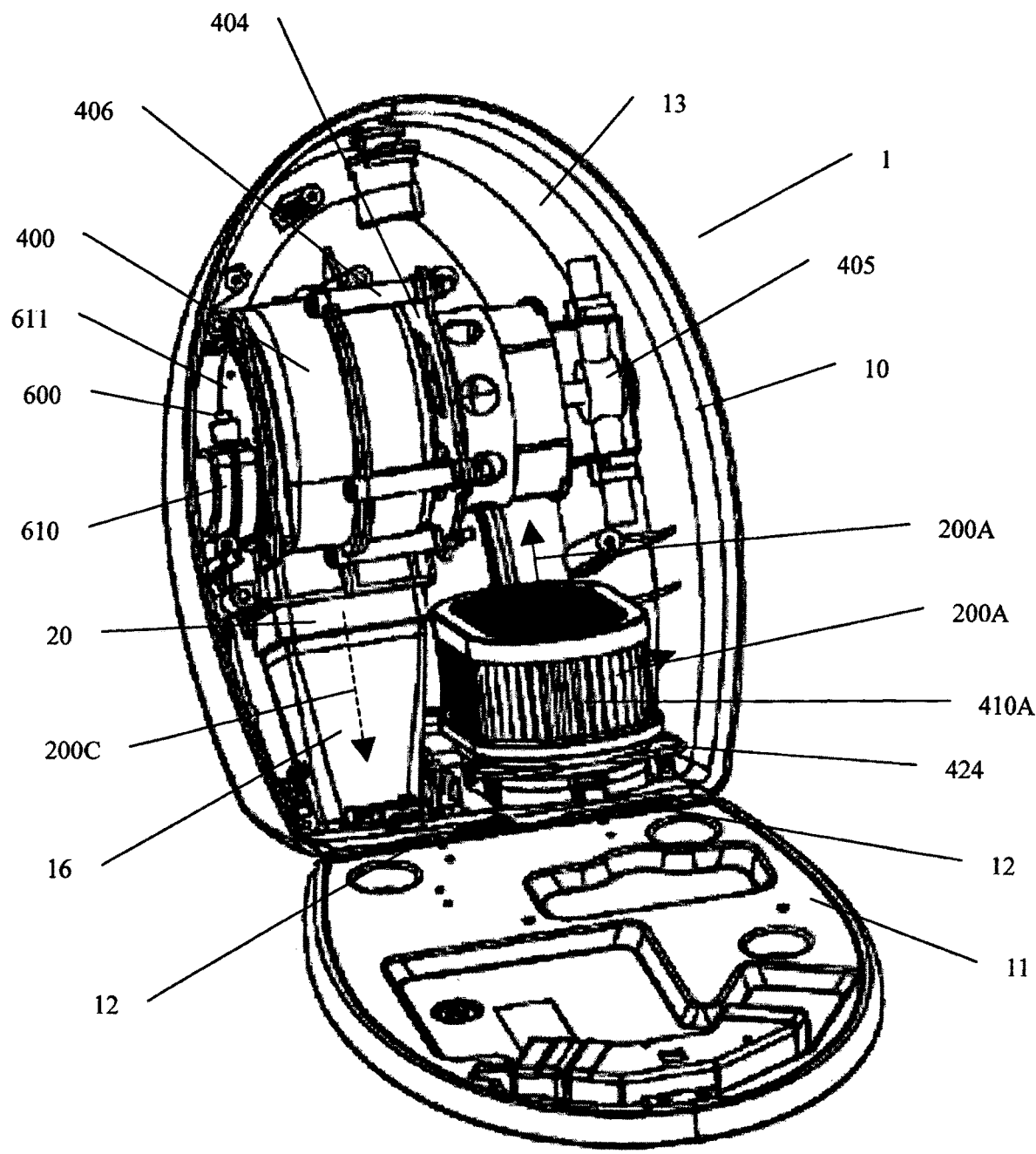
Figure 5:
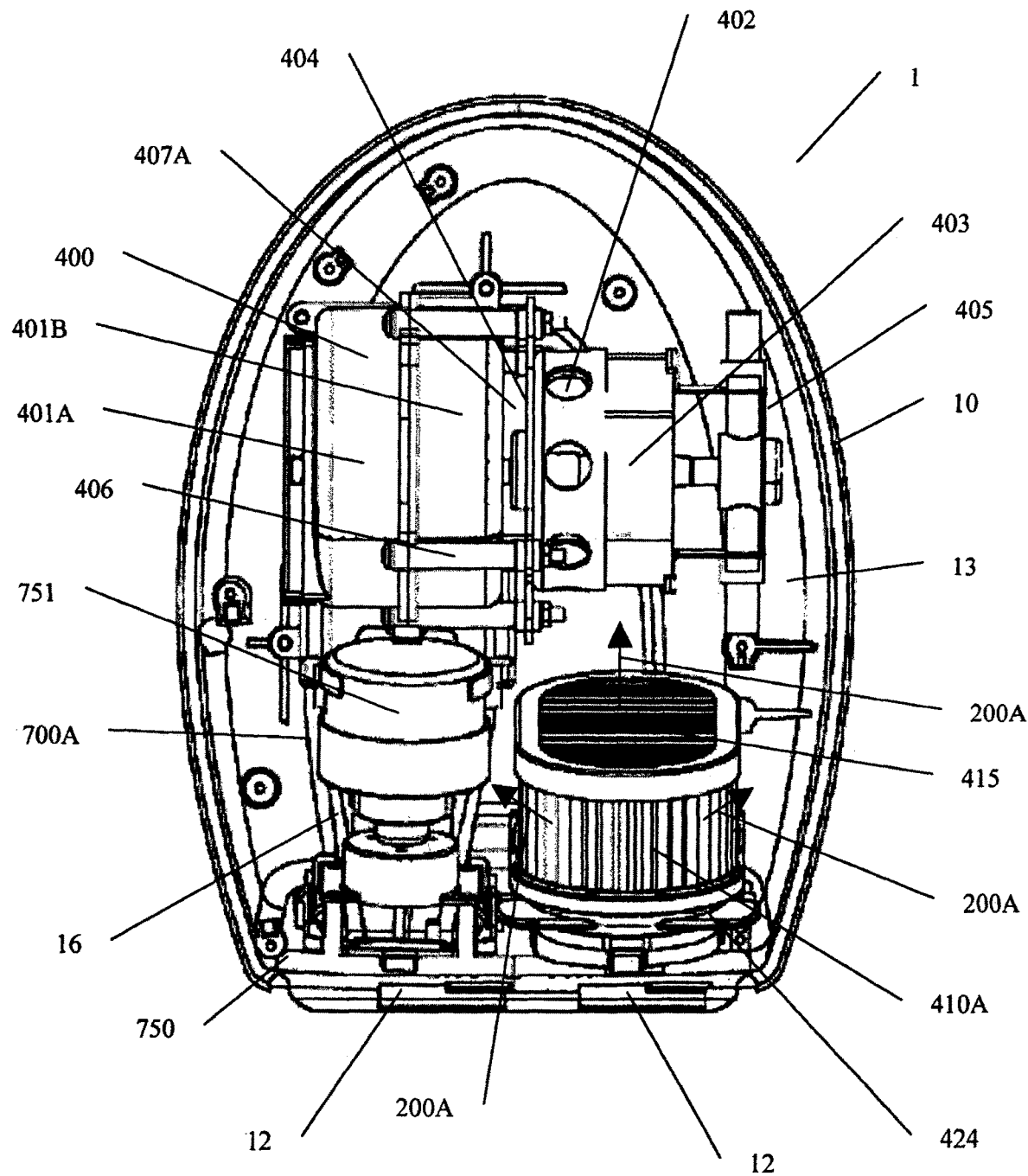
Figure 6A:
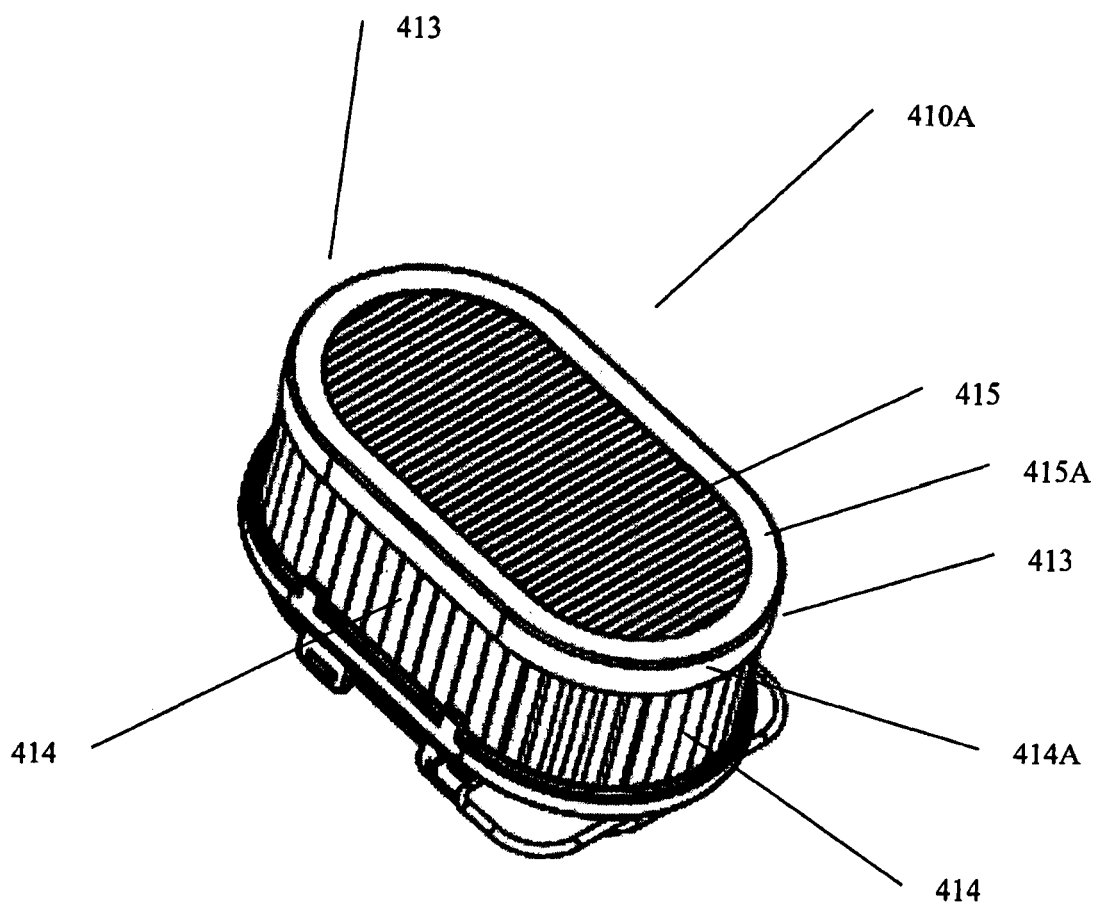
Figure 6B:
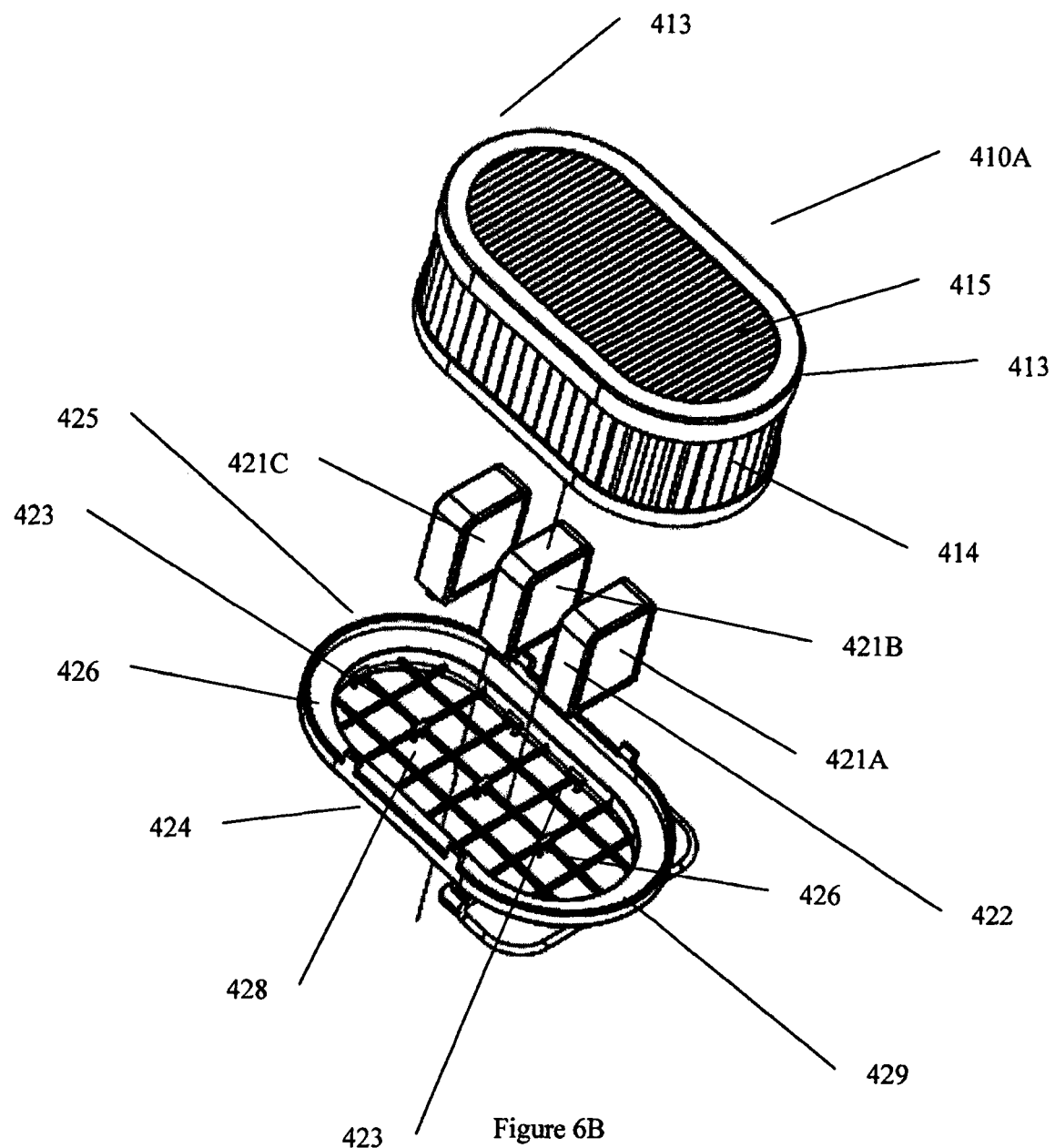
Figures 6C, 6D:
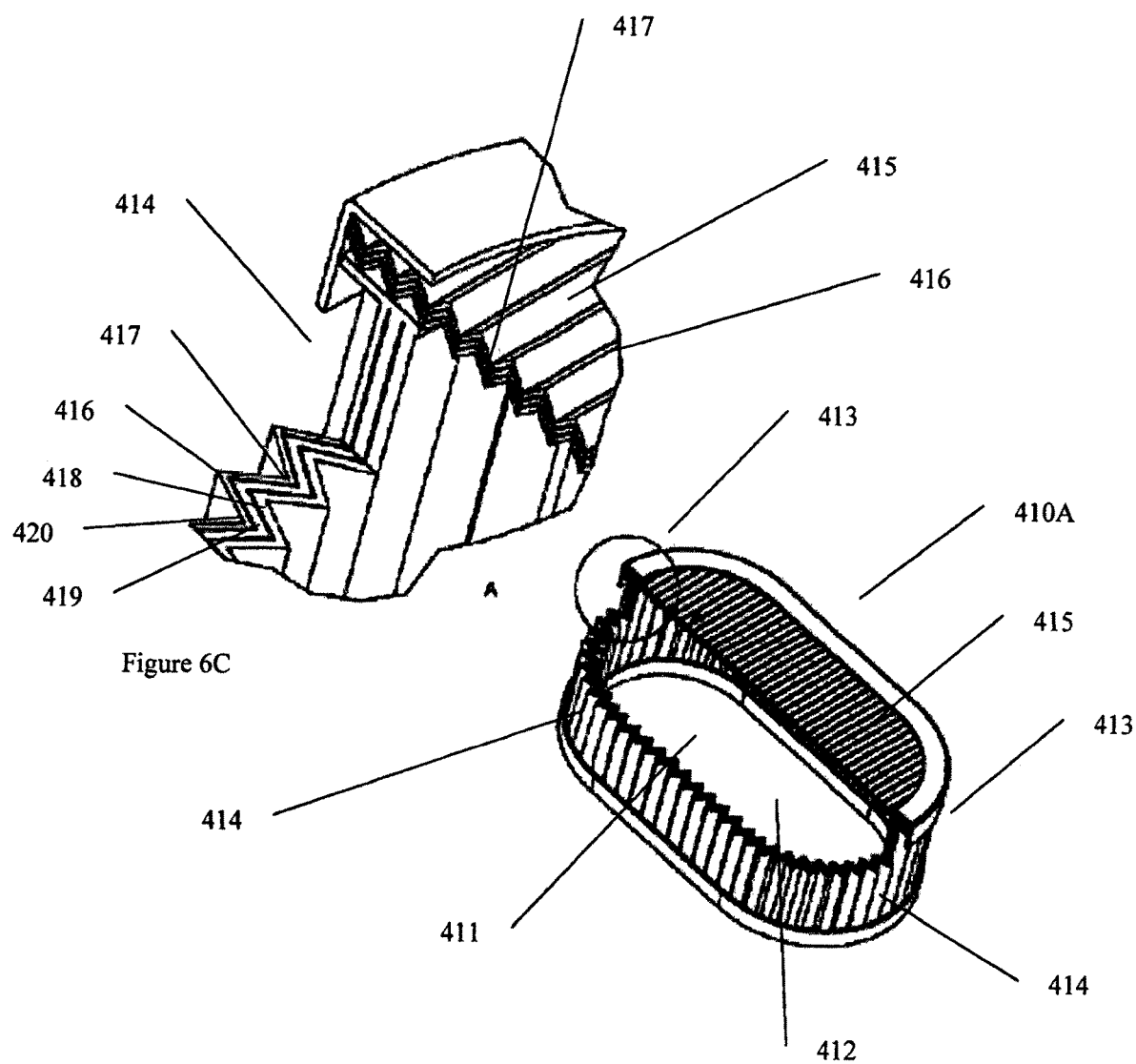
Figure 6E:
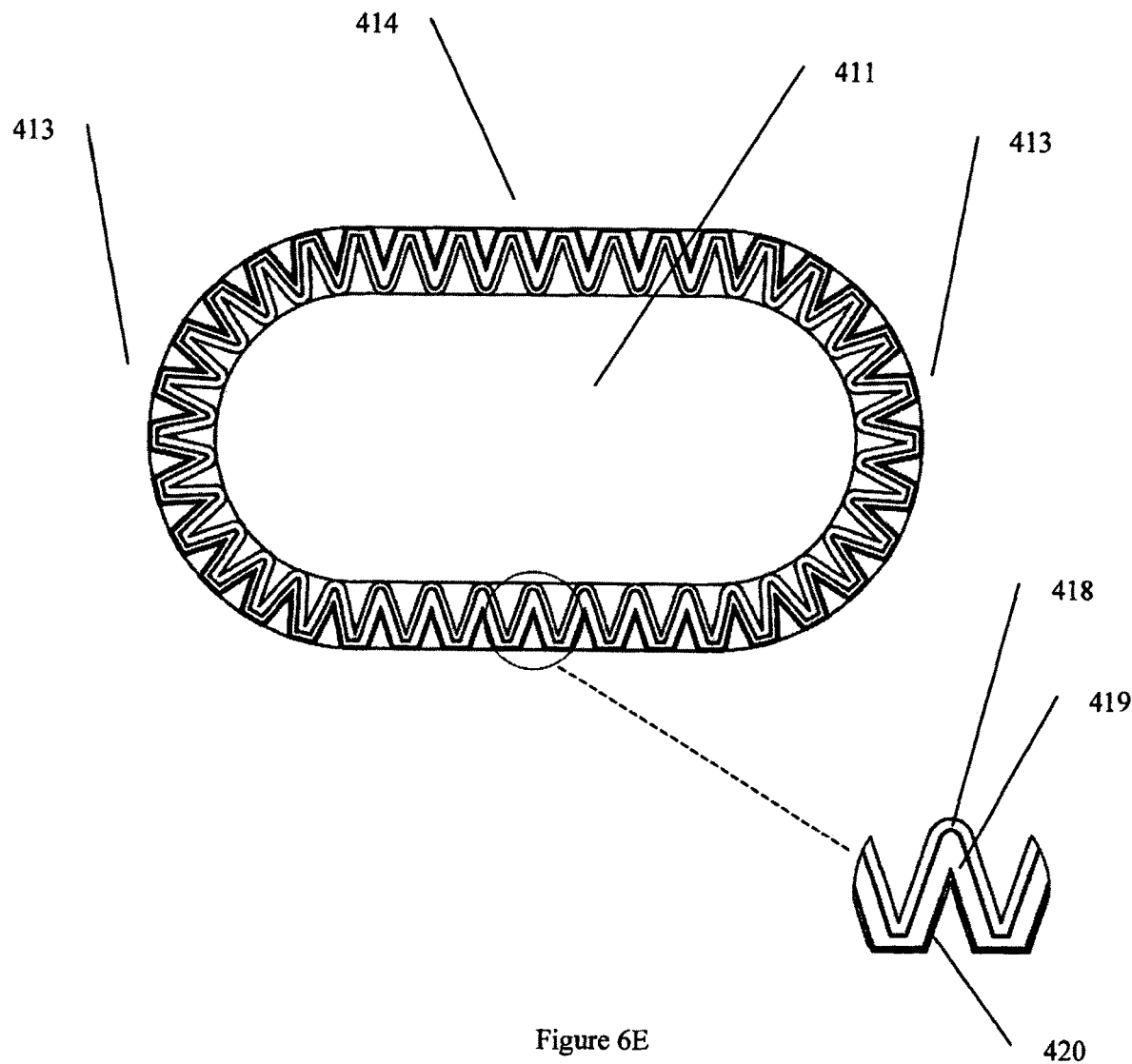
Figure 6F:
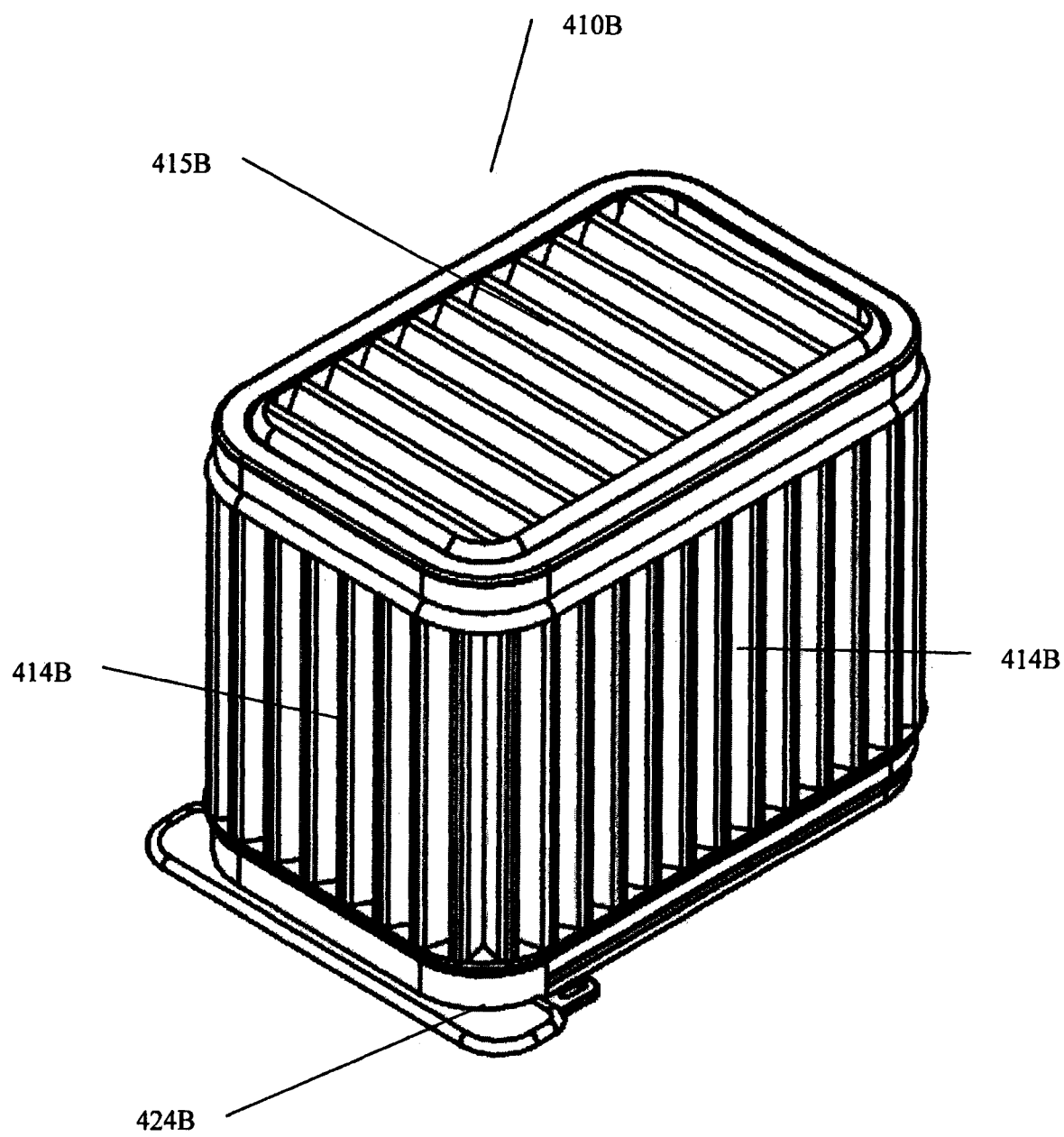
Figure 6G:
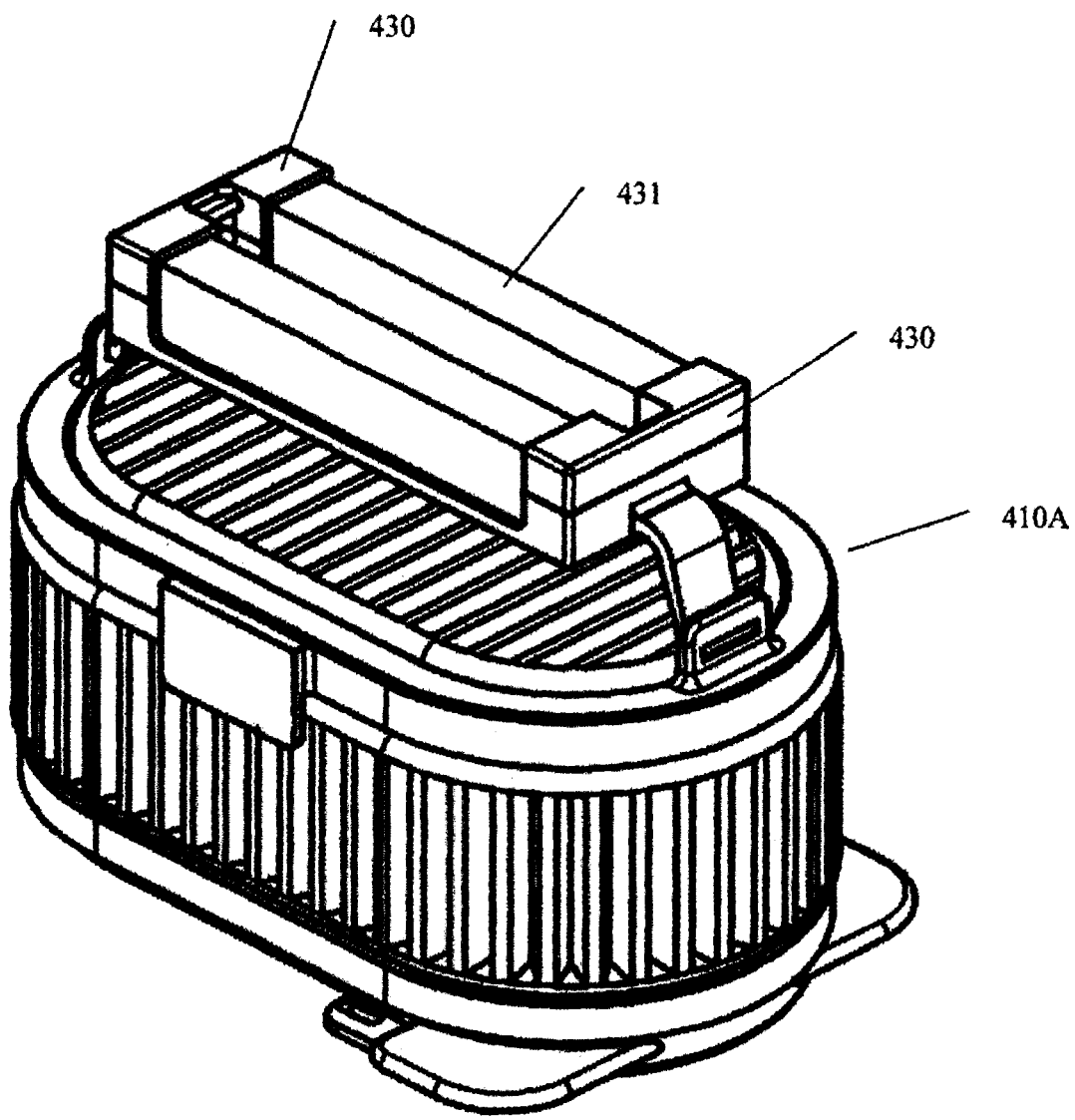
Figure 7:
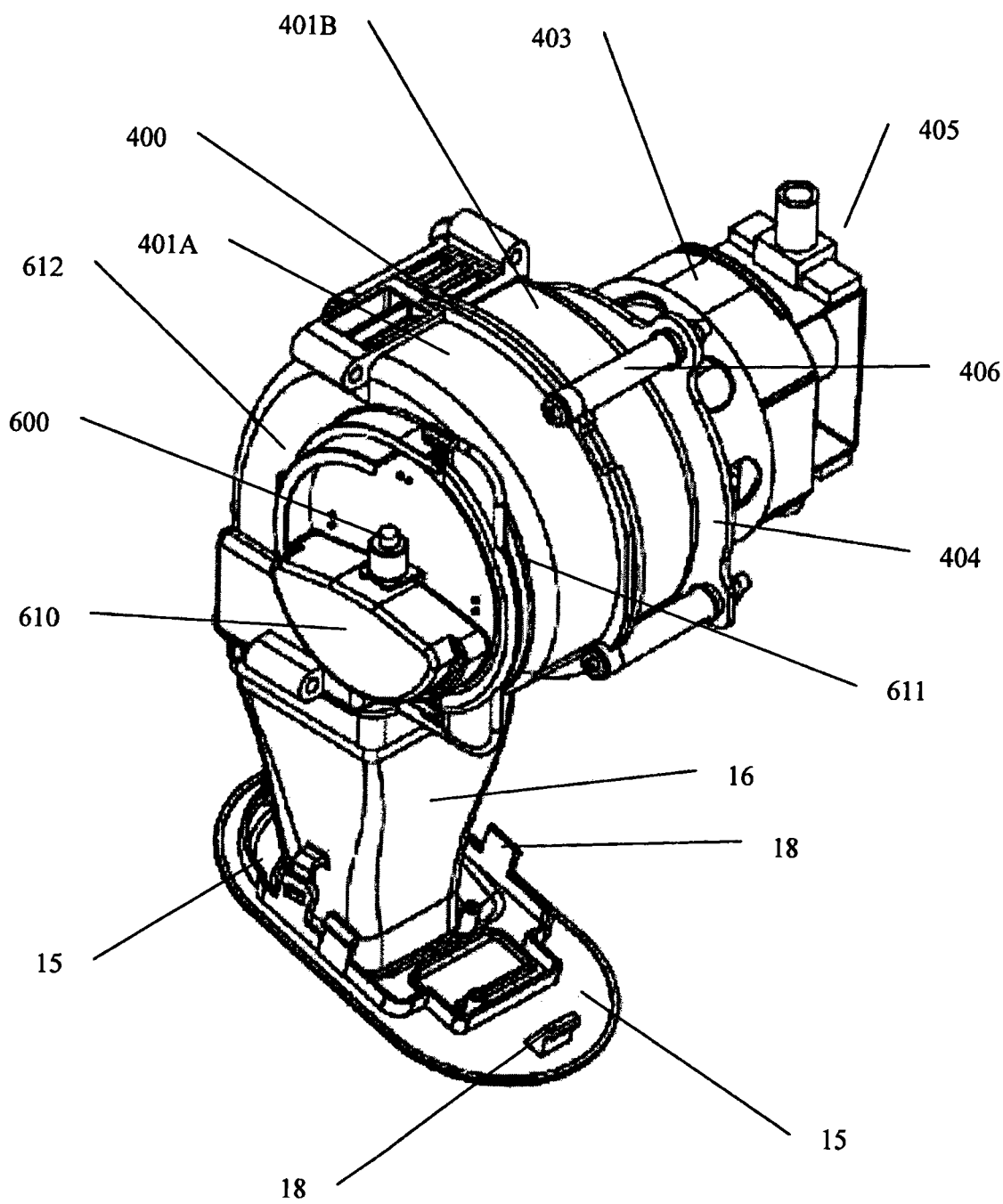
Figure 8A:
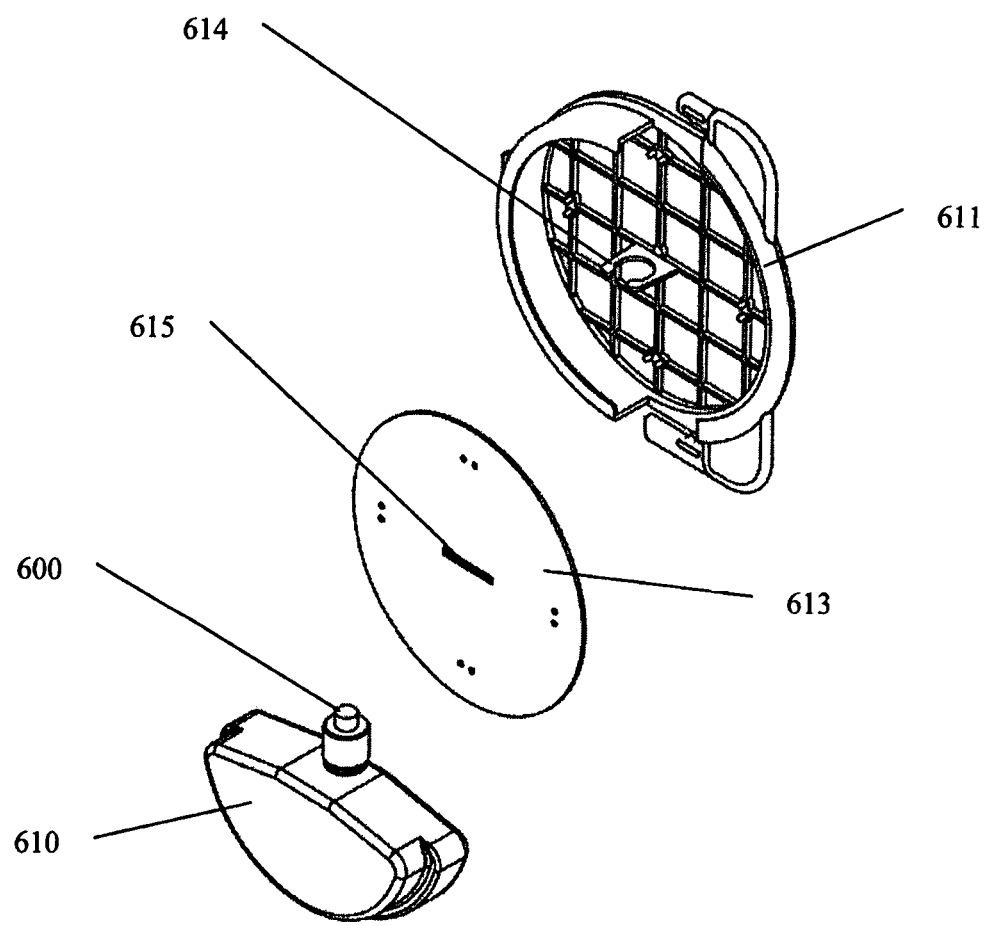
Figure 8B:
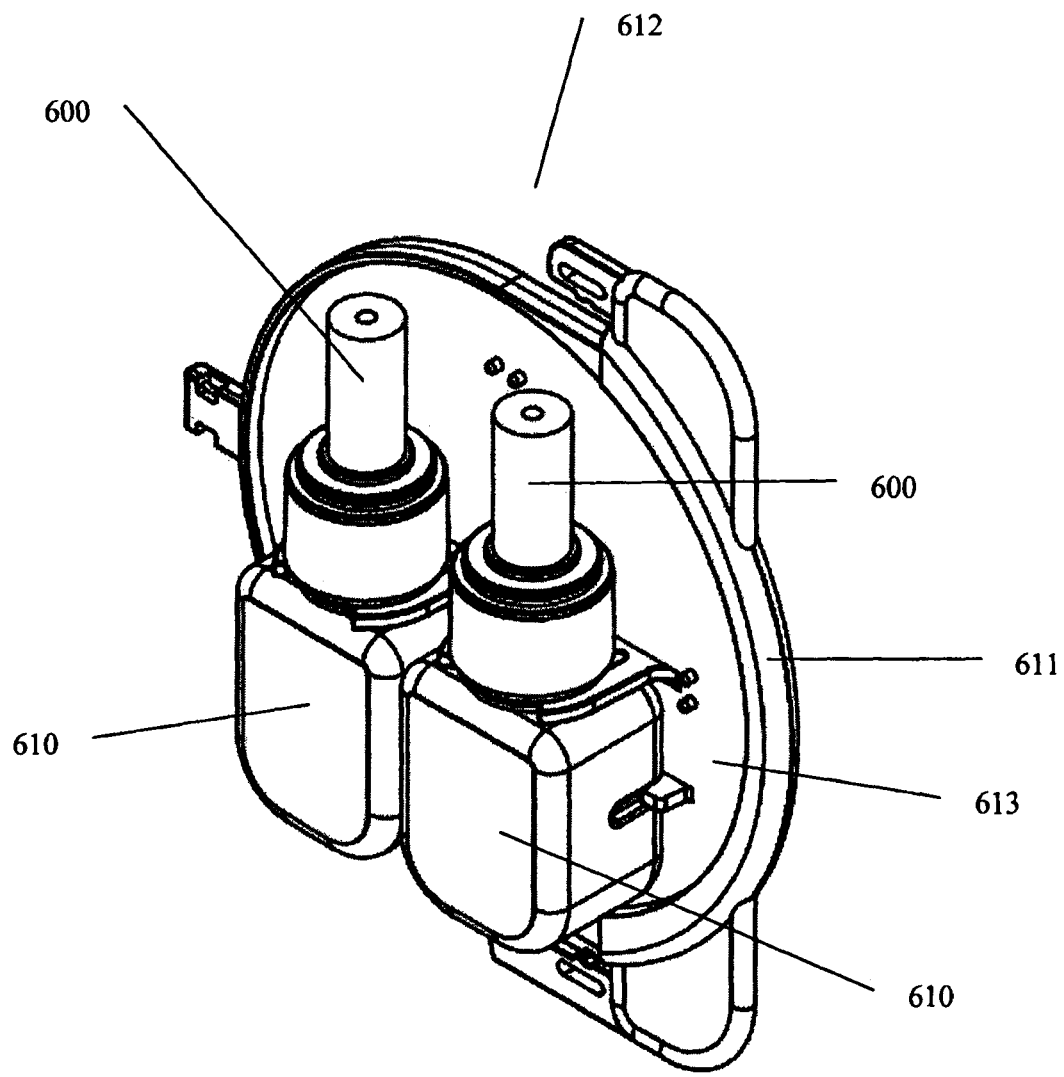
Figure 9A:
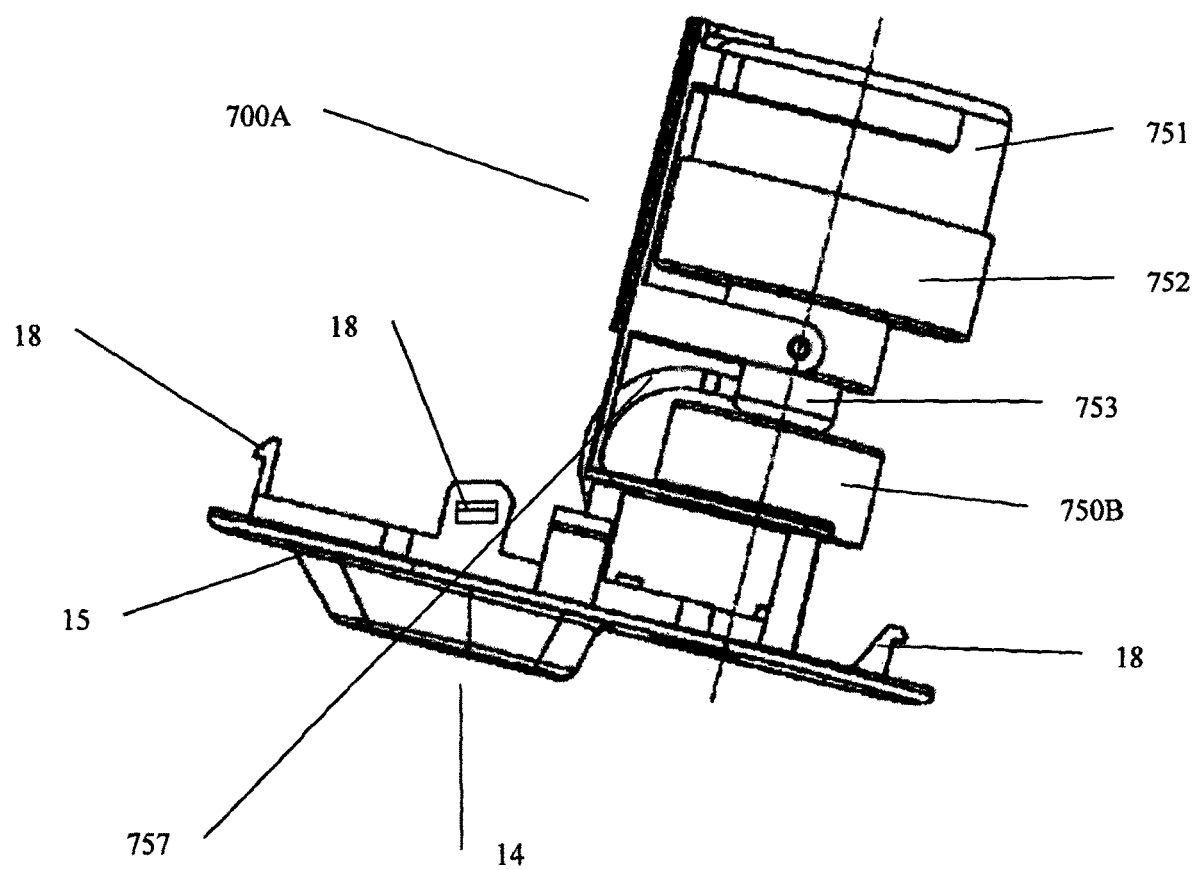
Figure 9B:
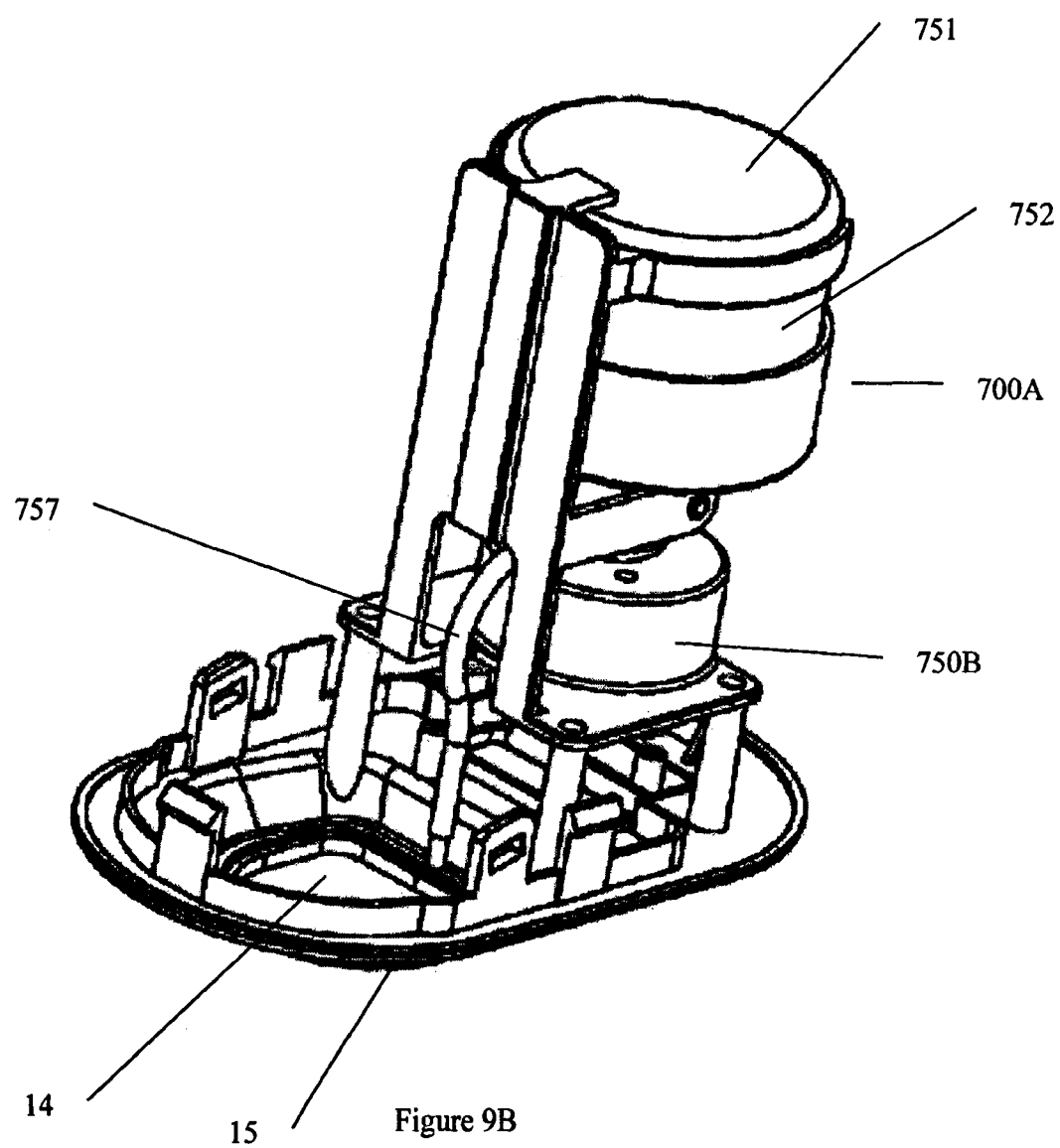
Figure 9C:
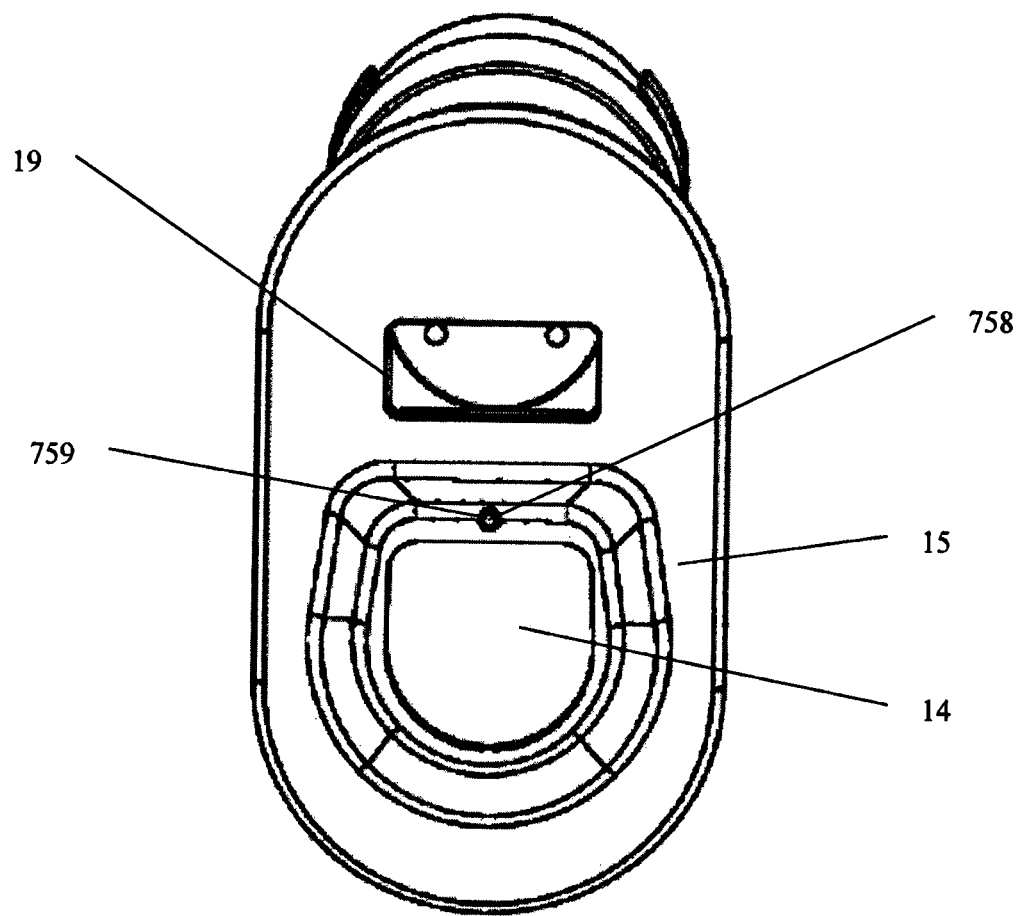
Figure 9D:
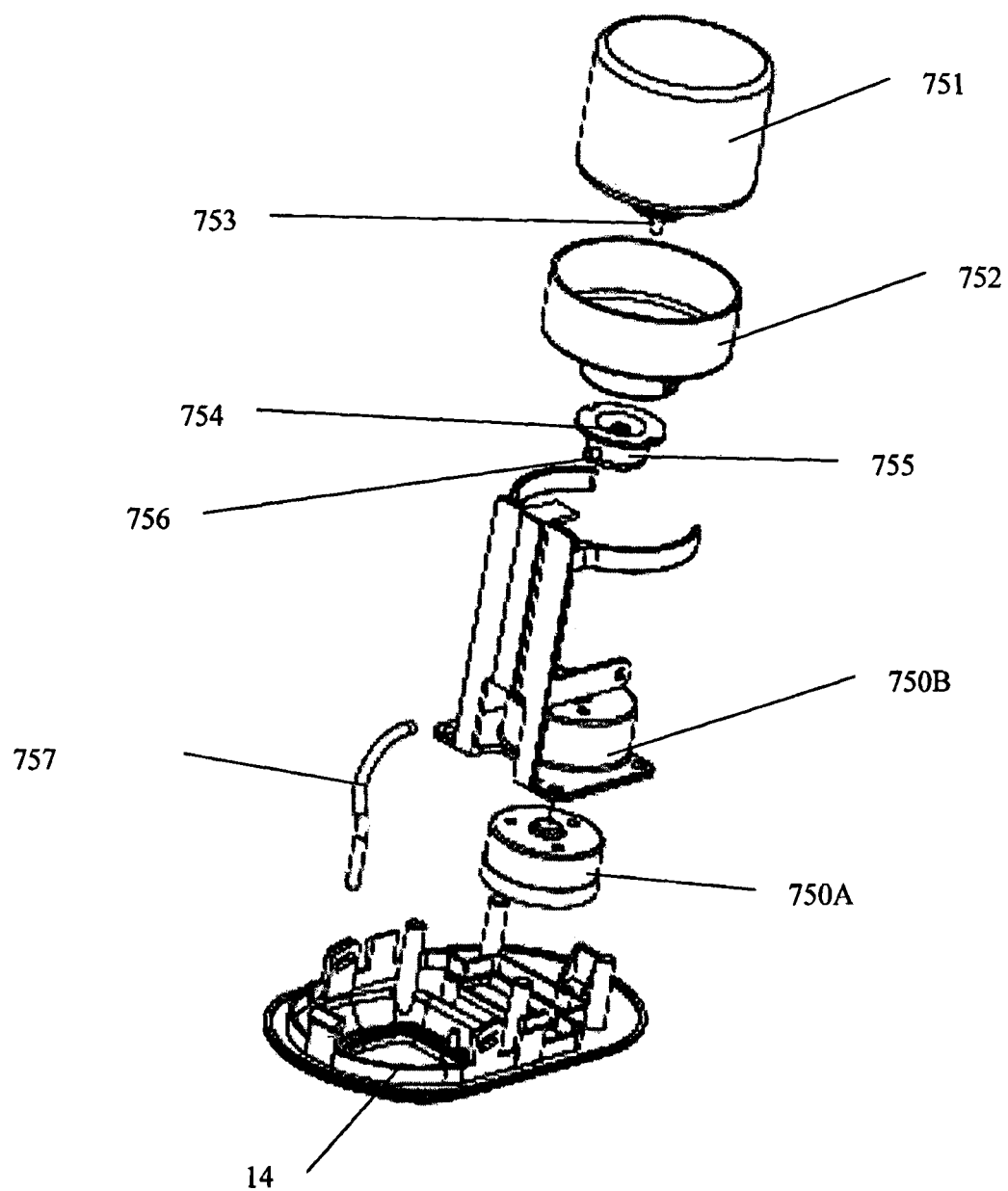
Figure 10:
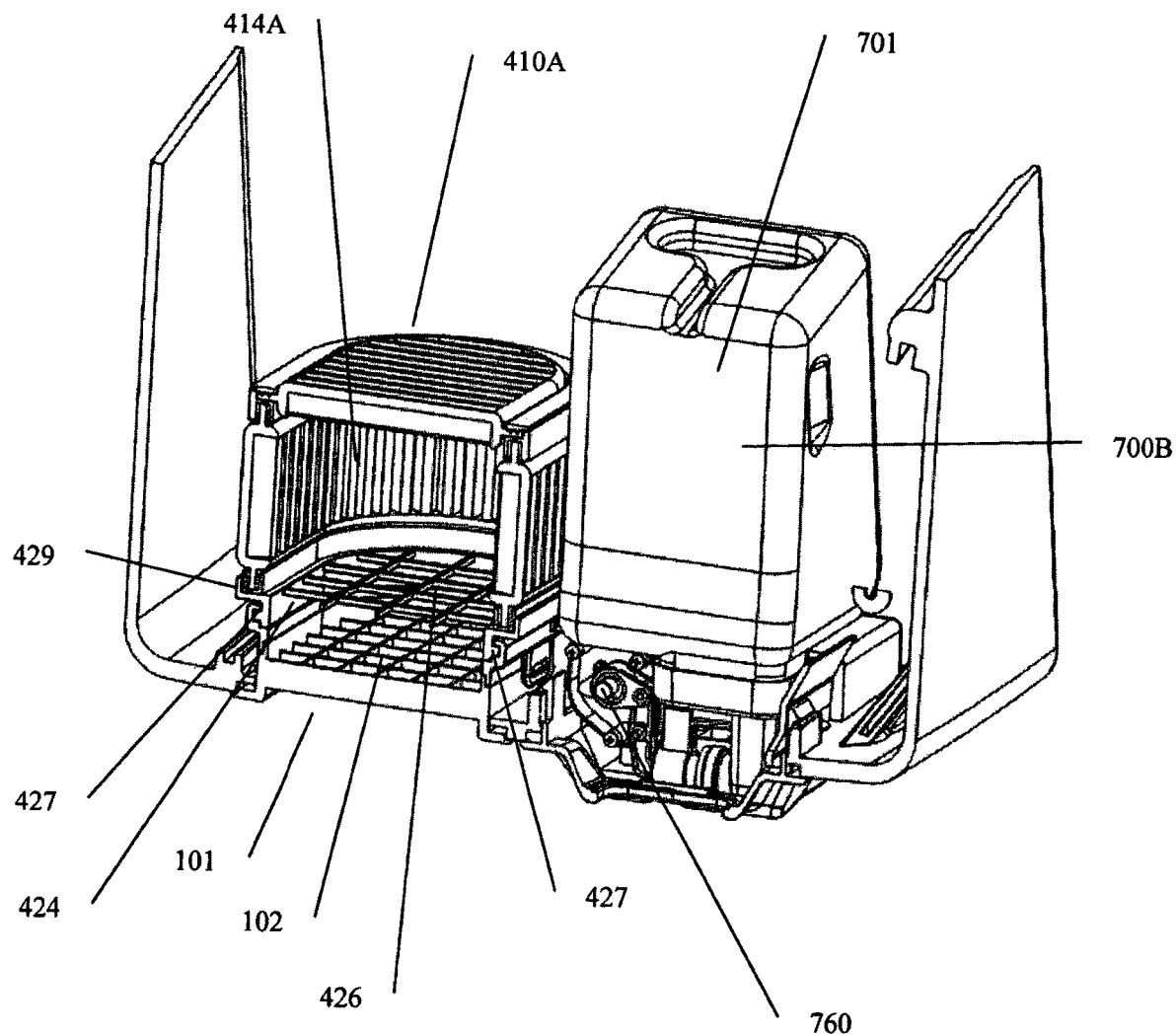
Figure 11A:
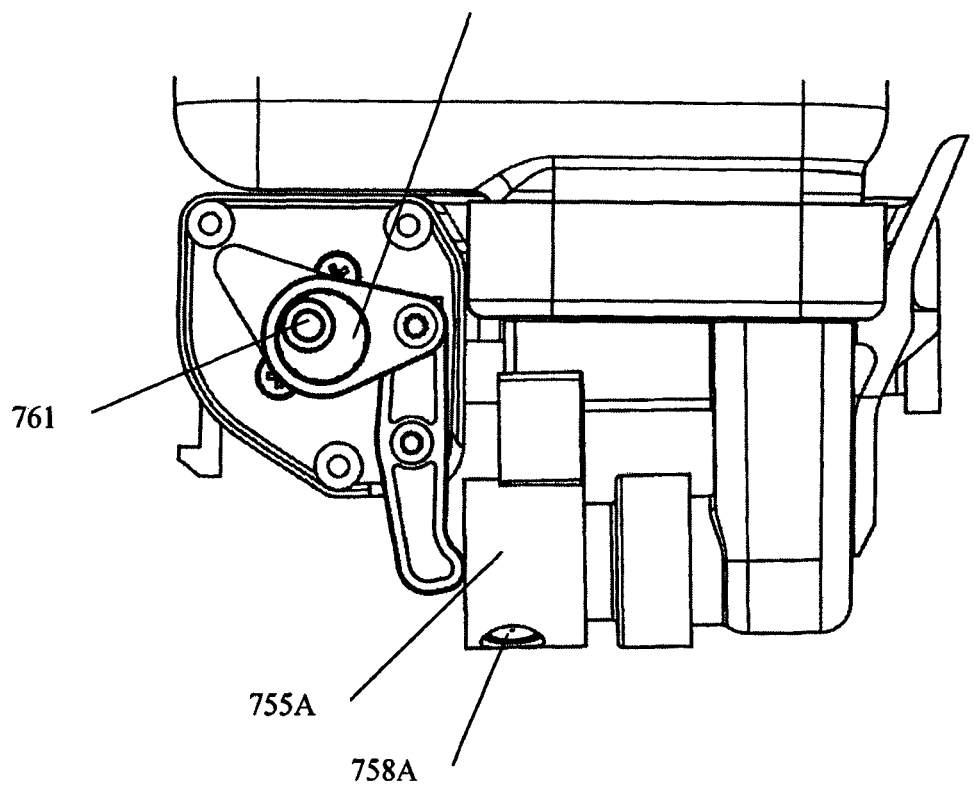
Figure 11B:
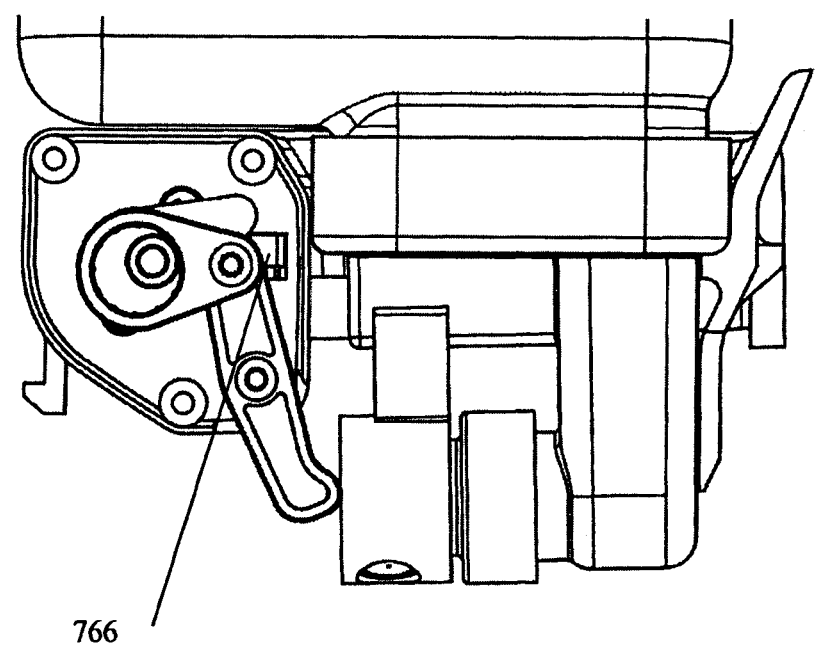
Figure 12A:
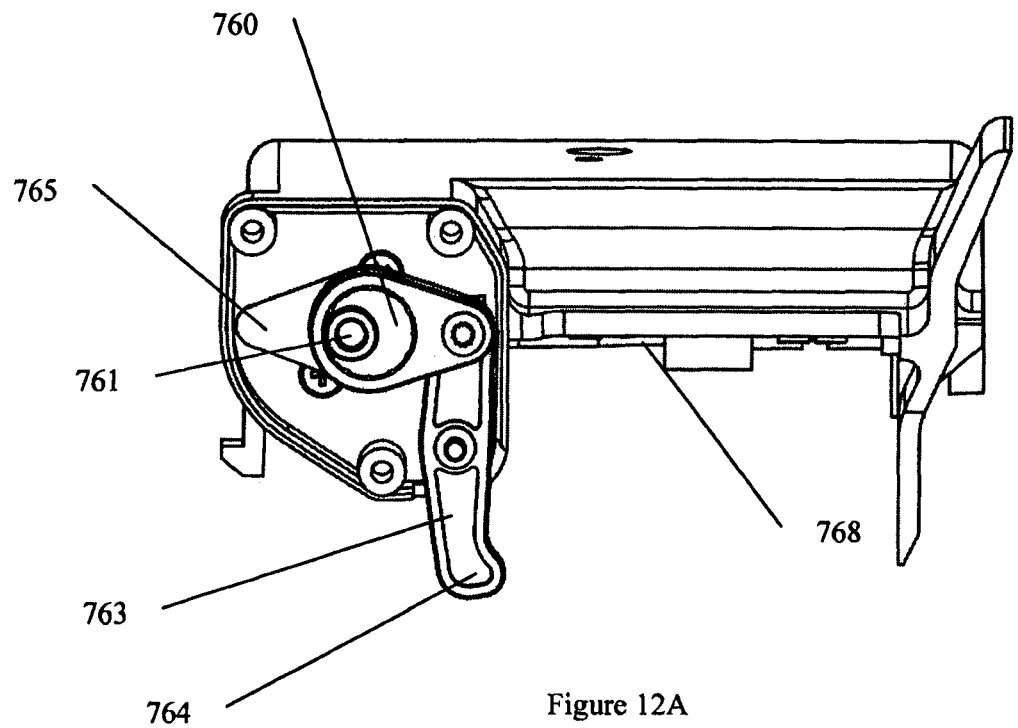
Figure 12B:
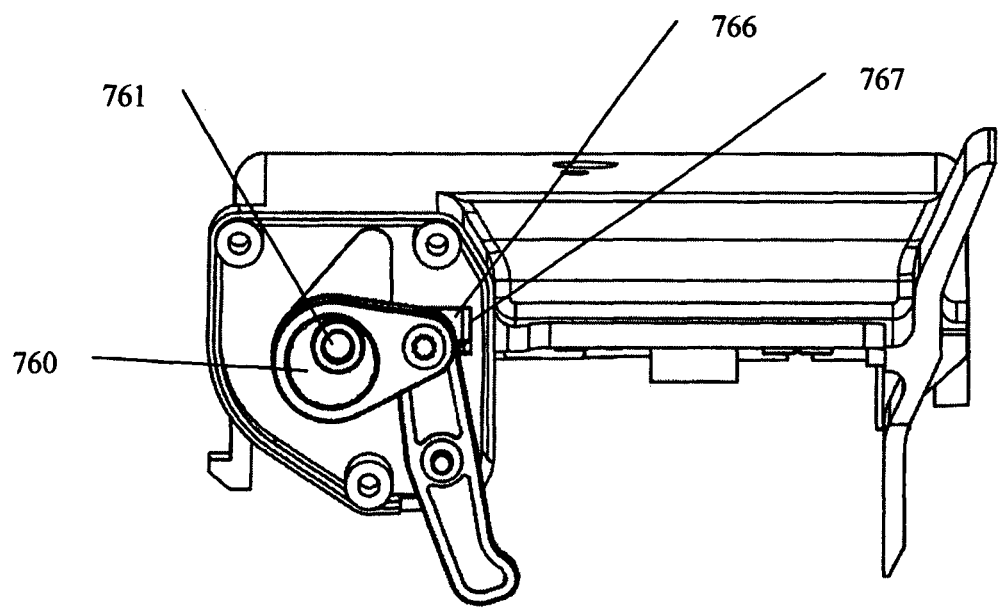
Figure 12C:
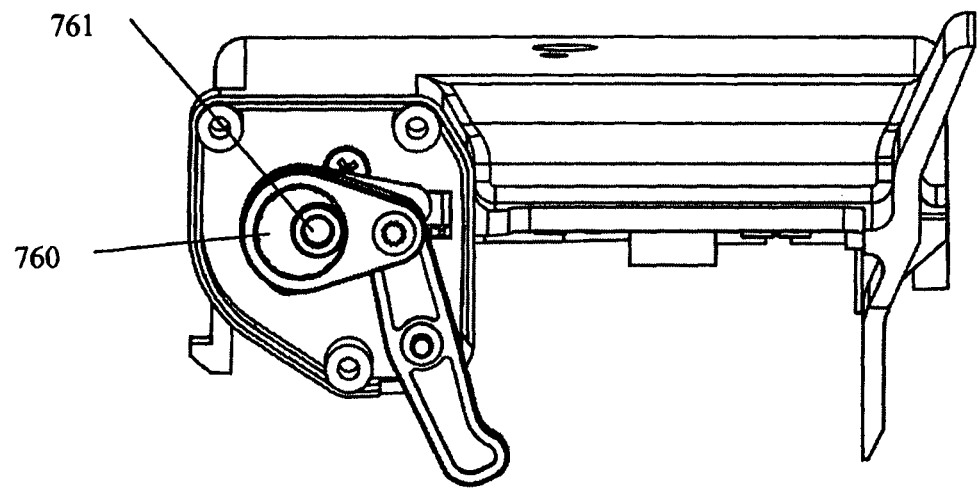
Figure 12D:
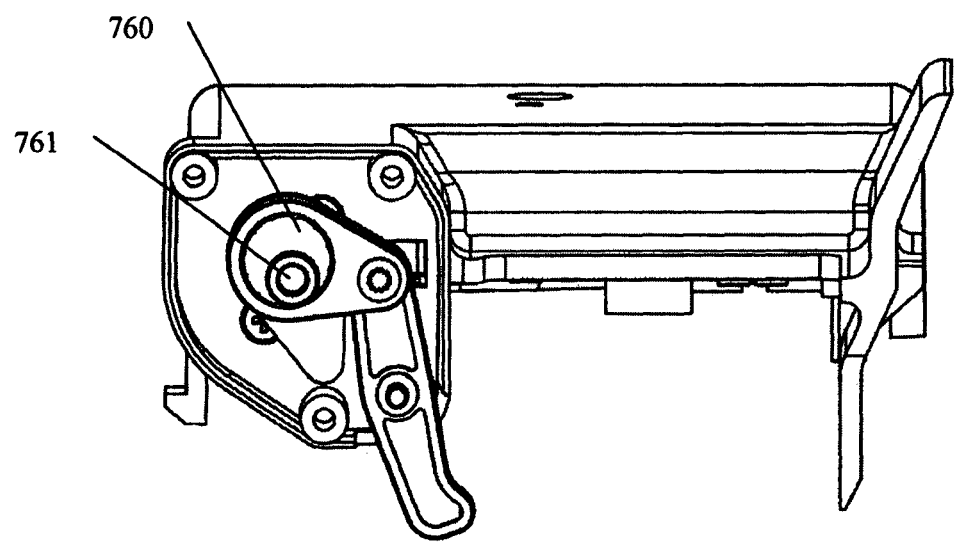
Figure 12E:
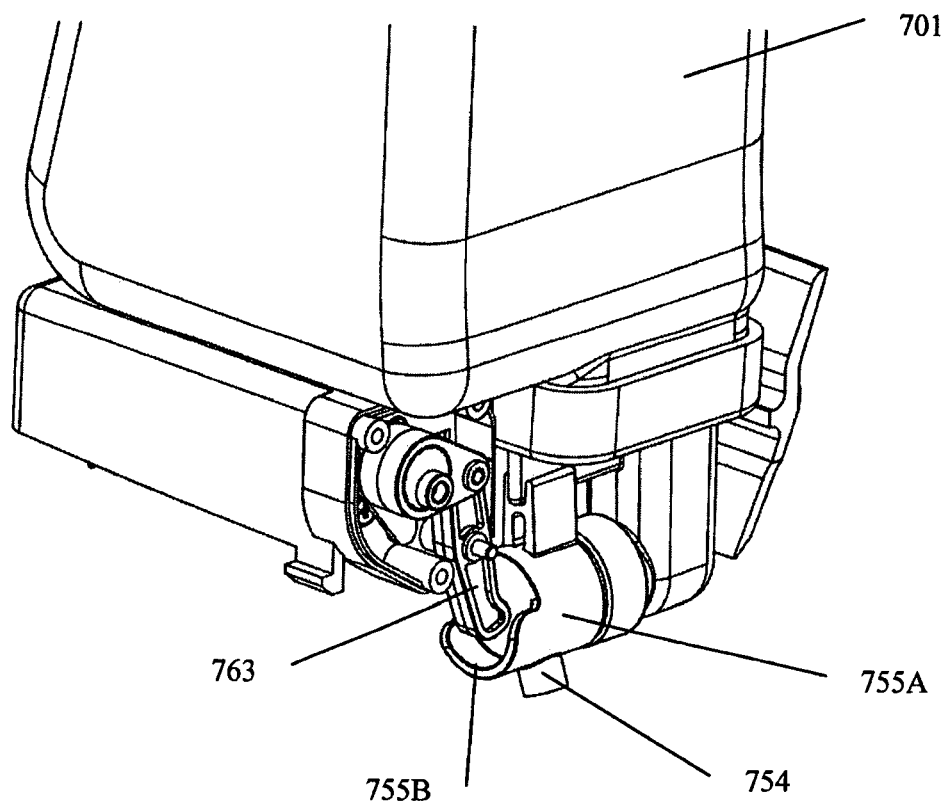
Figures 13A, 13B:
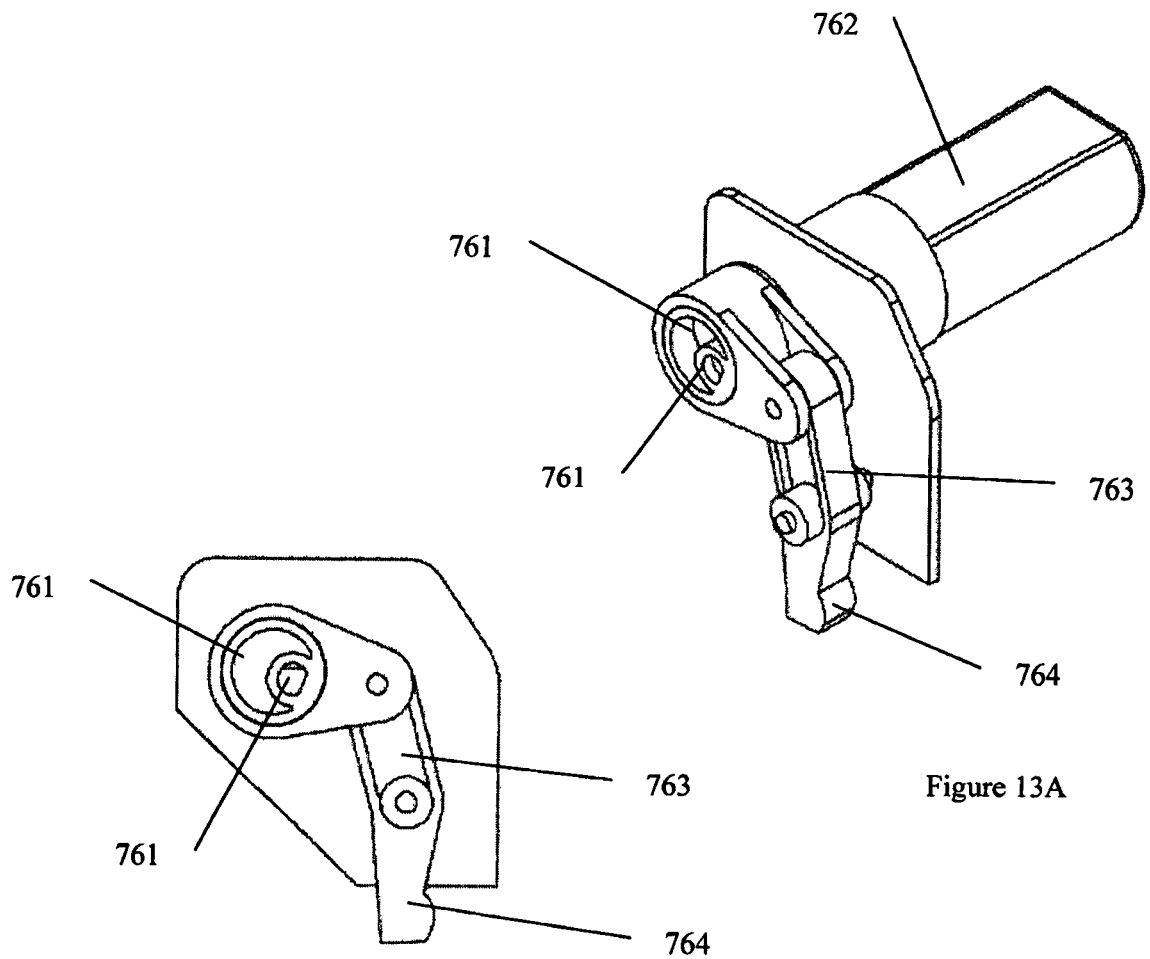
Figure 14A:
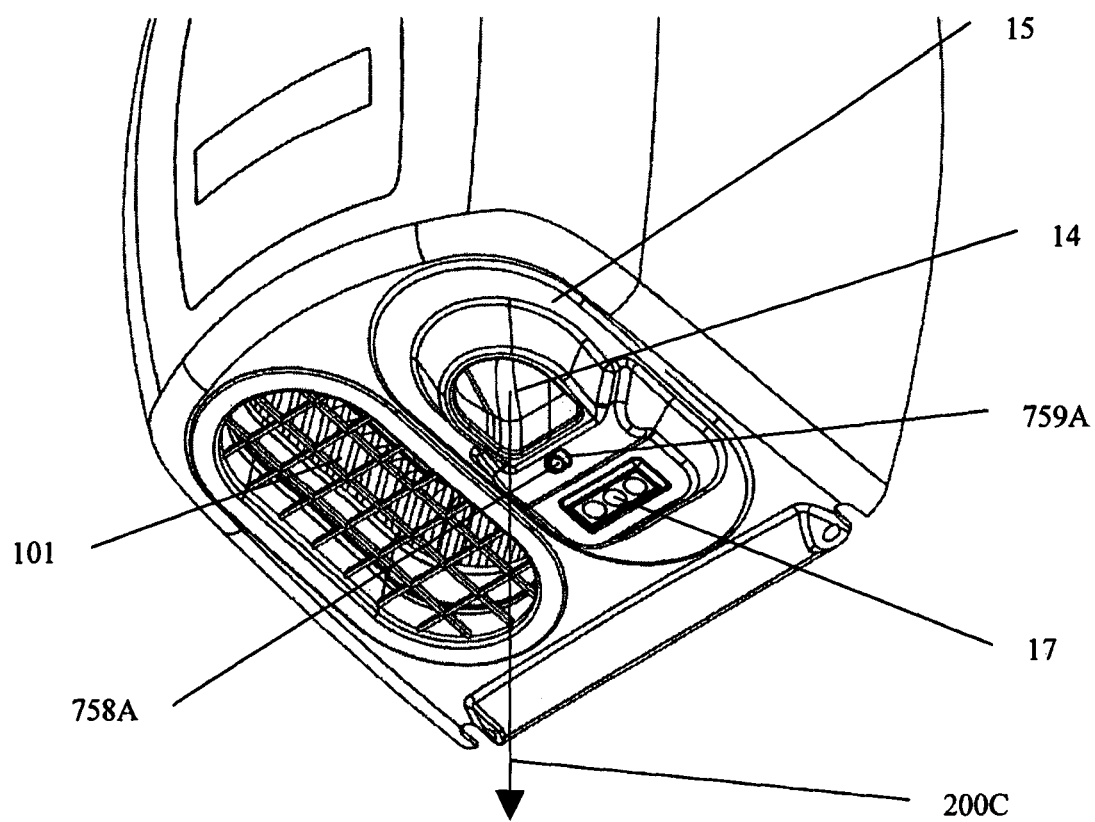
Figure 14B:
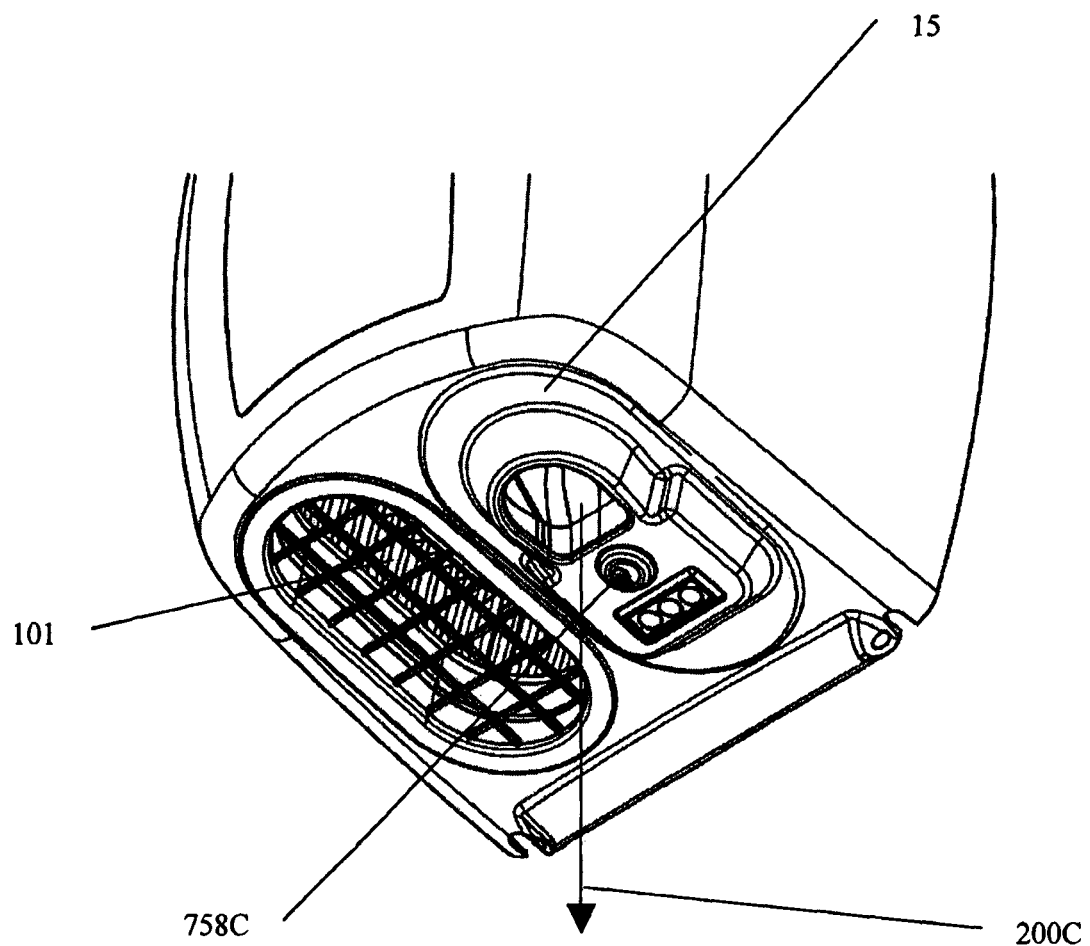
Figure 14C:
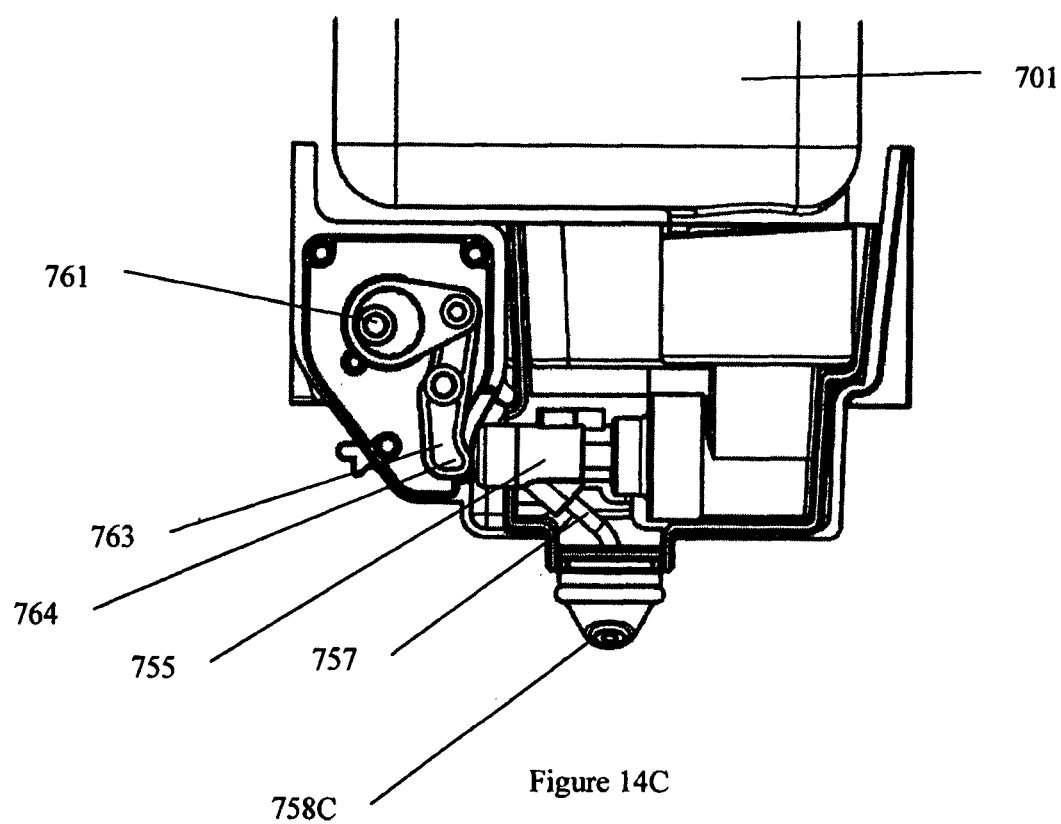
Figure 15A:
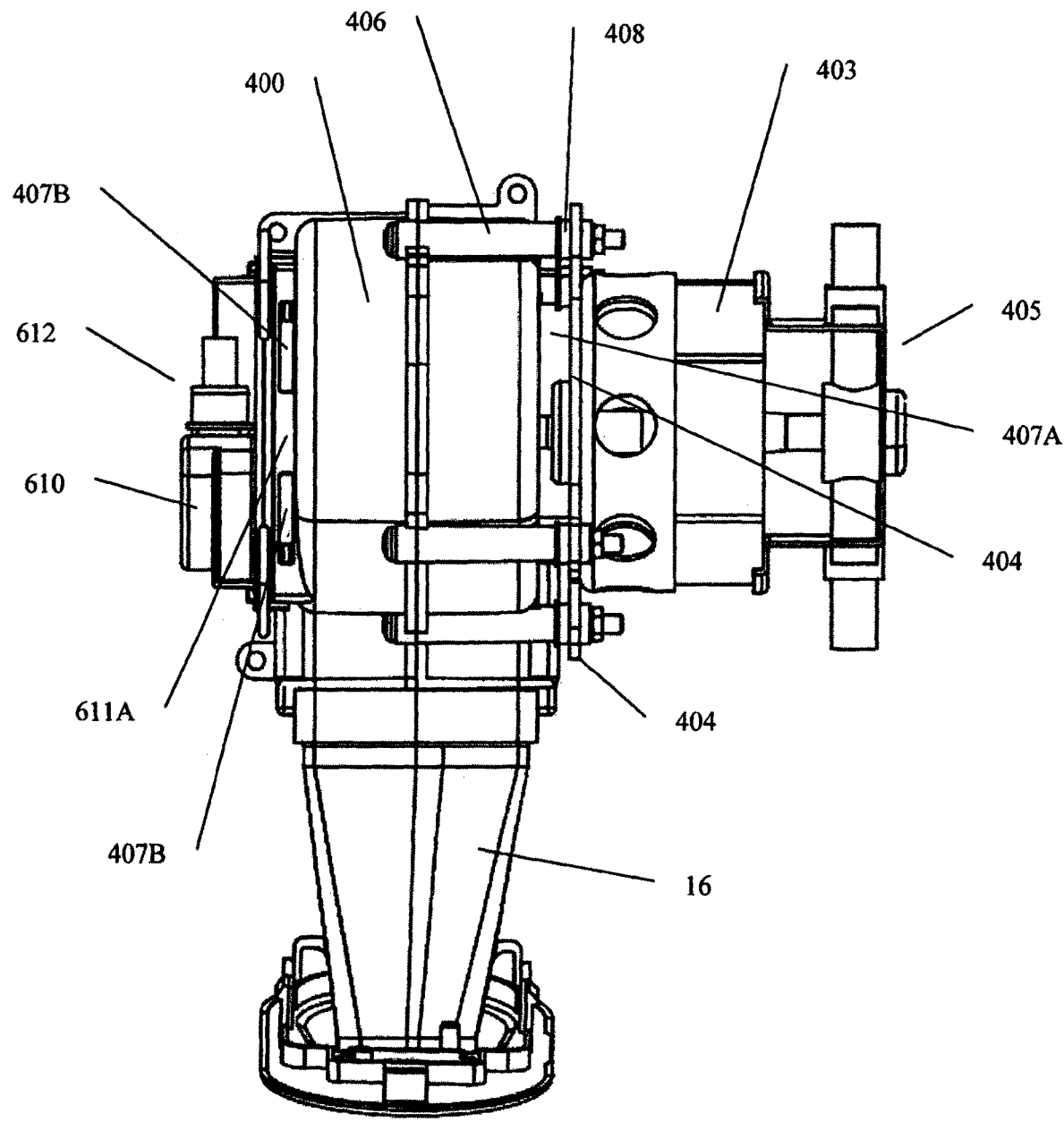
Figure 15B:
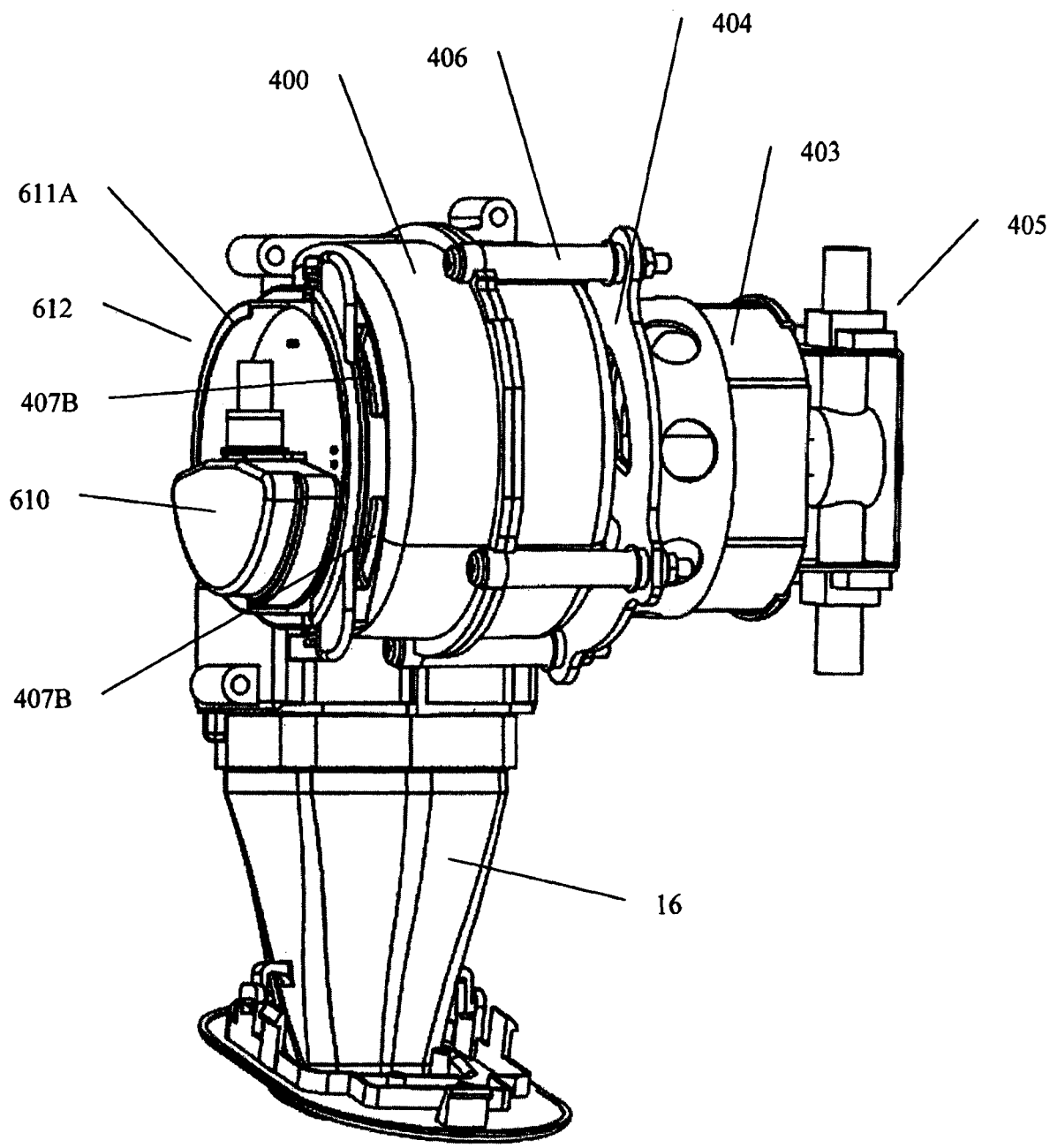
Figure 15C:
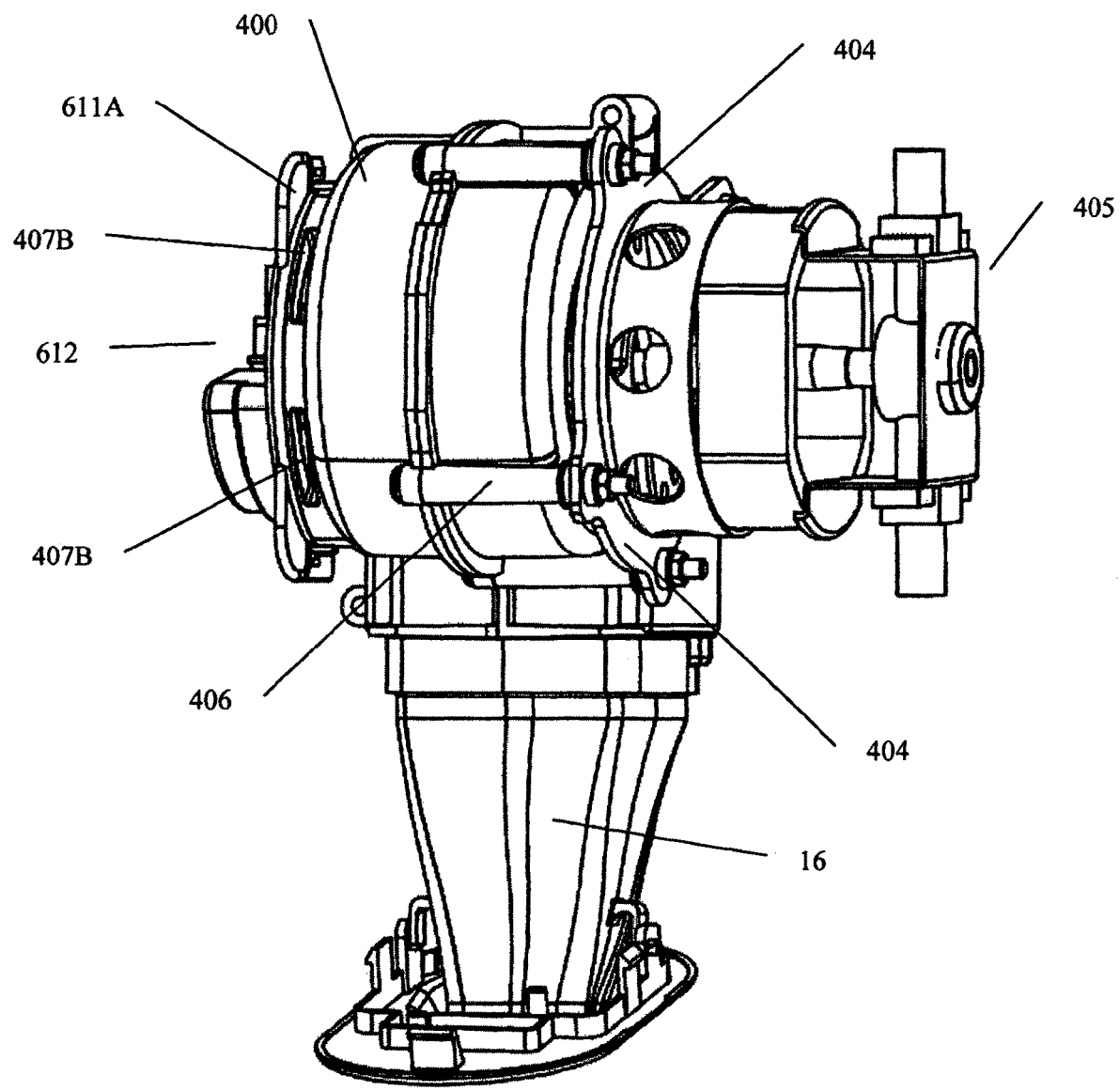
Figure 16A:
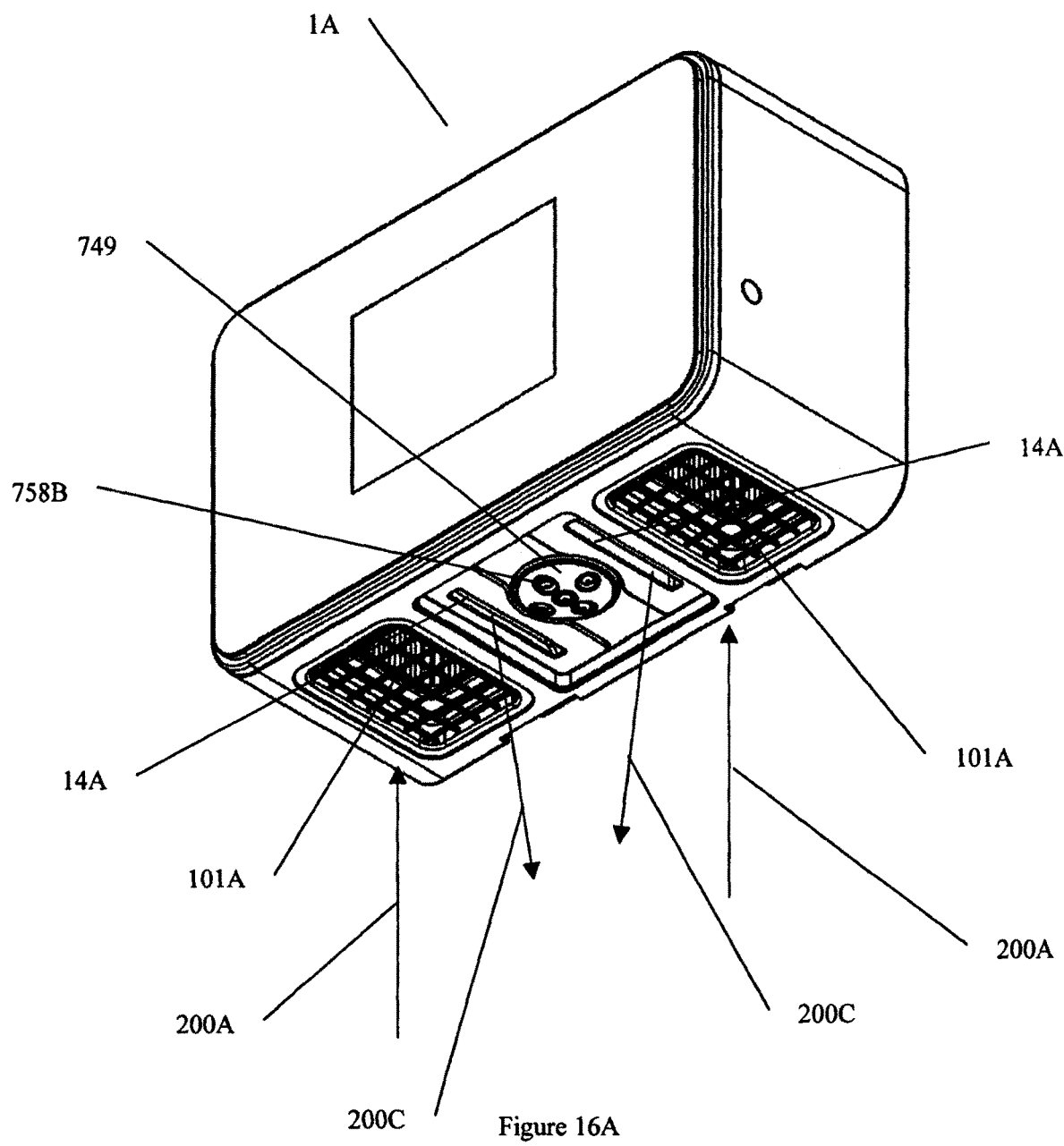
Figure 16B:
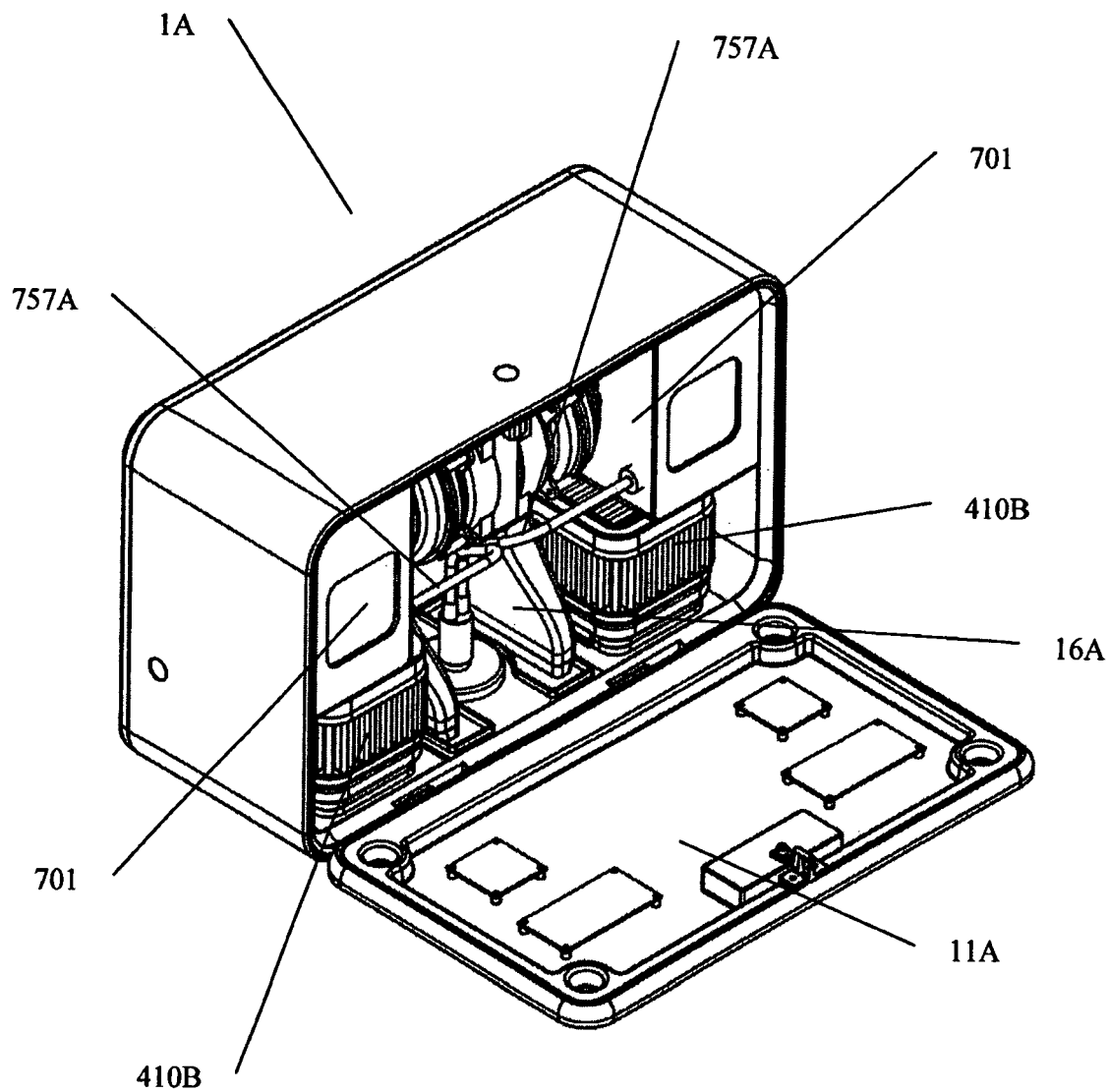
Figure 16C:
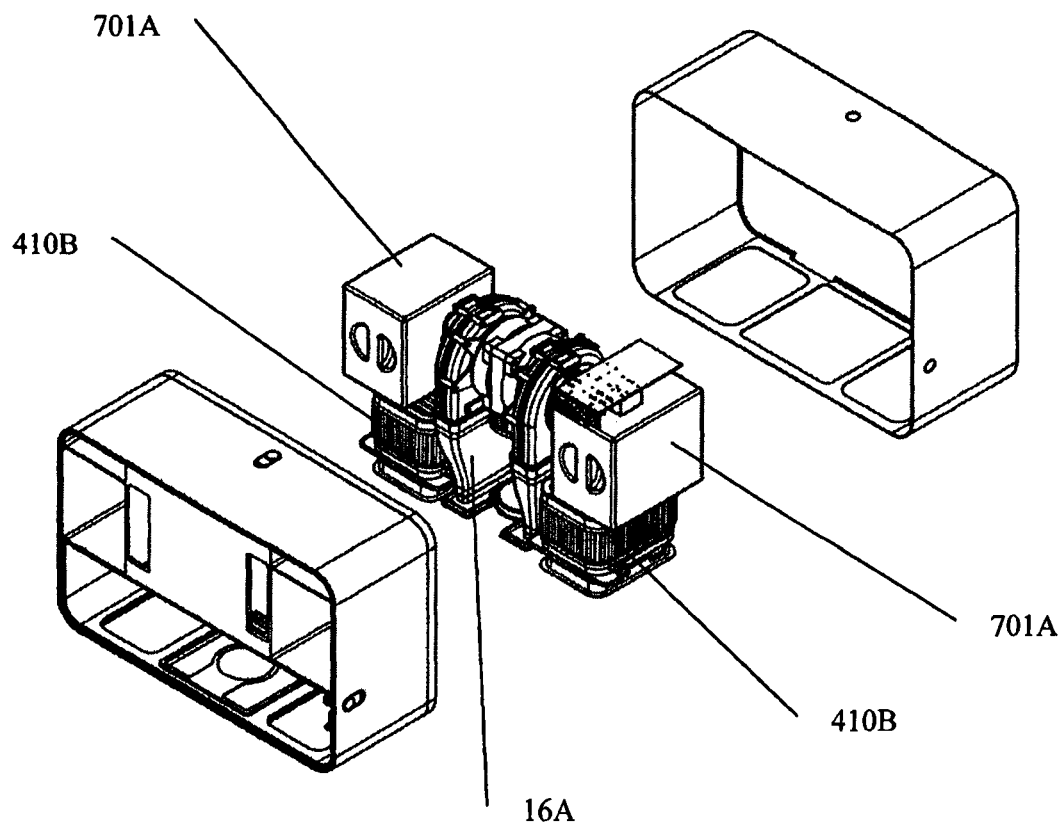
Figure 16D:
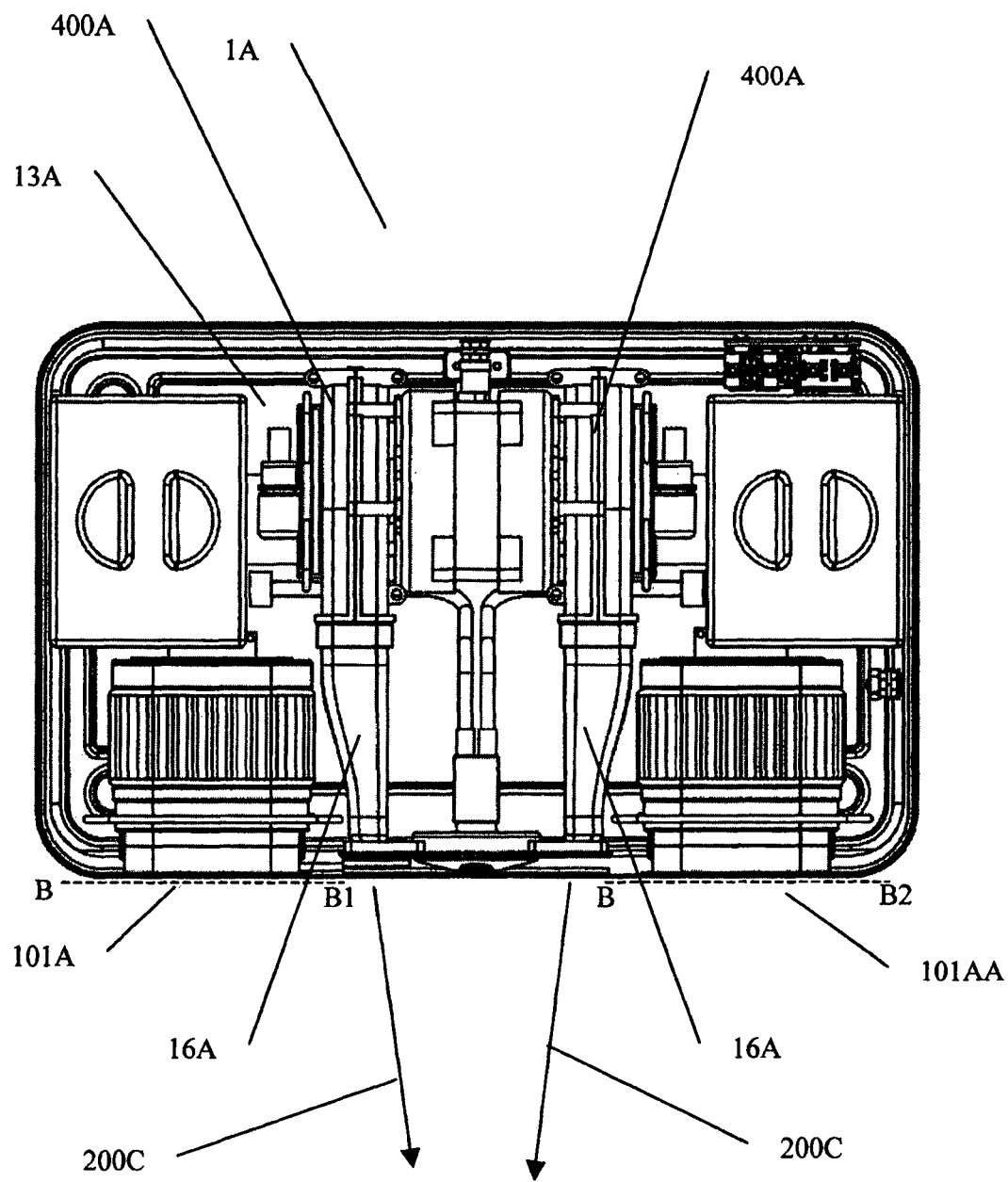
Figure 17A:
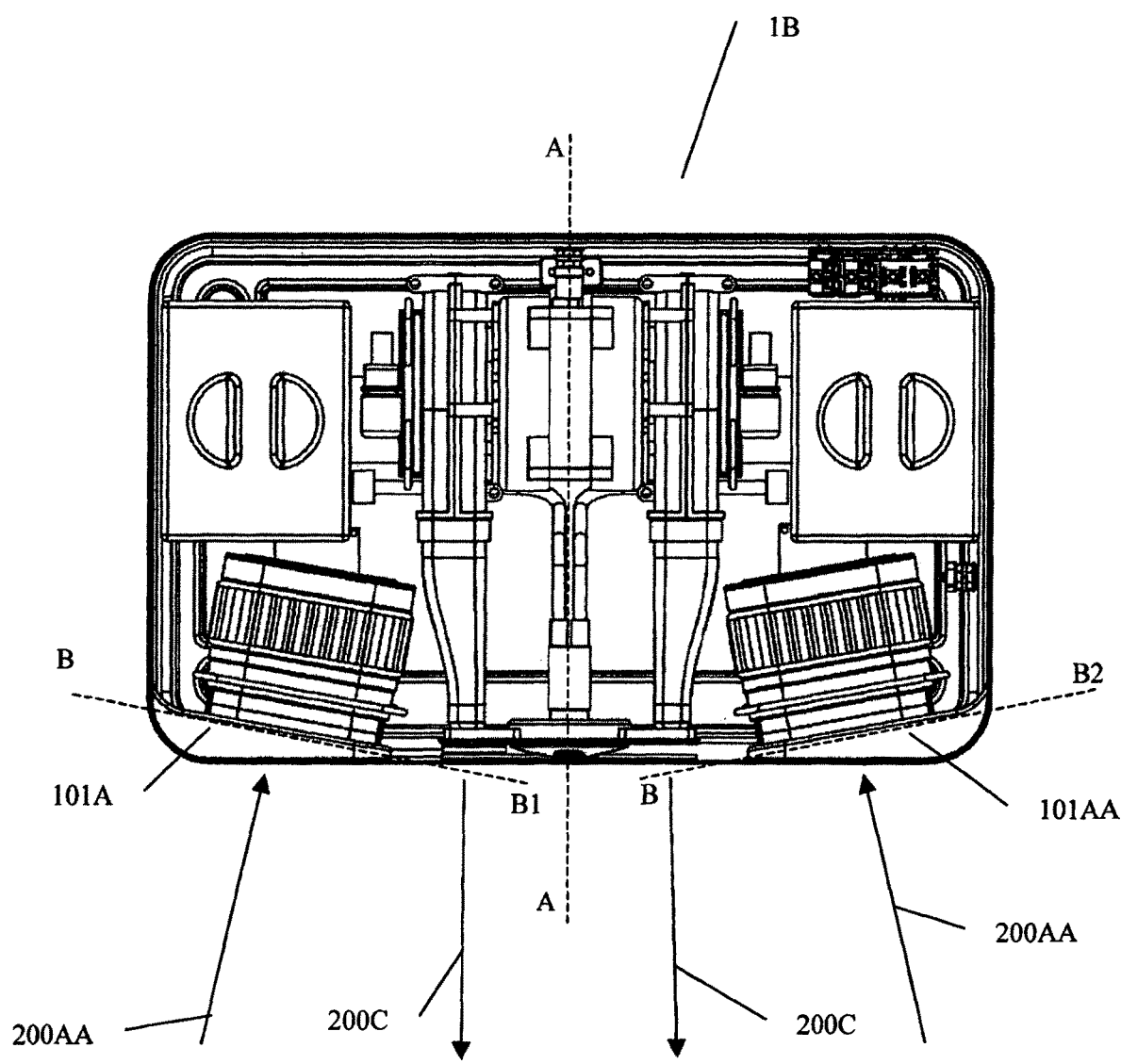
Figure 17B:
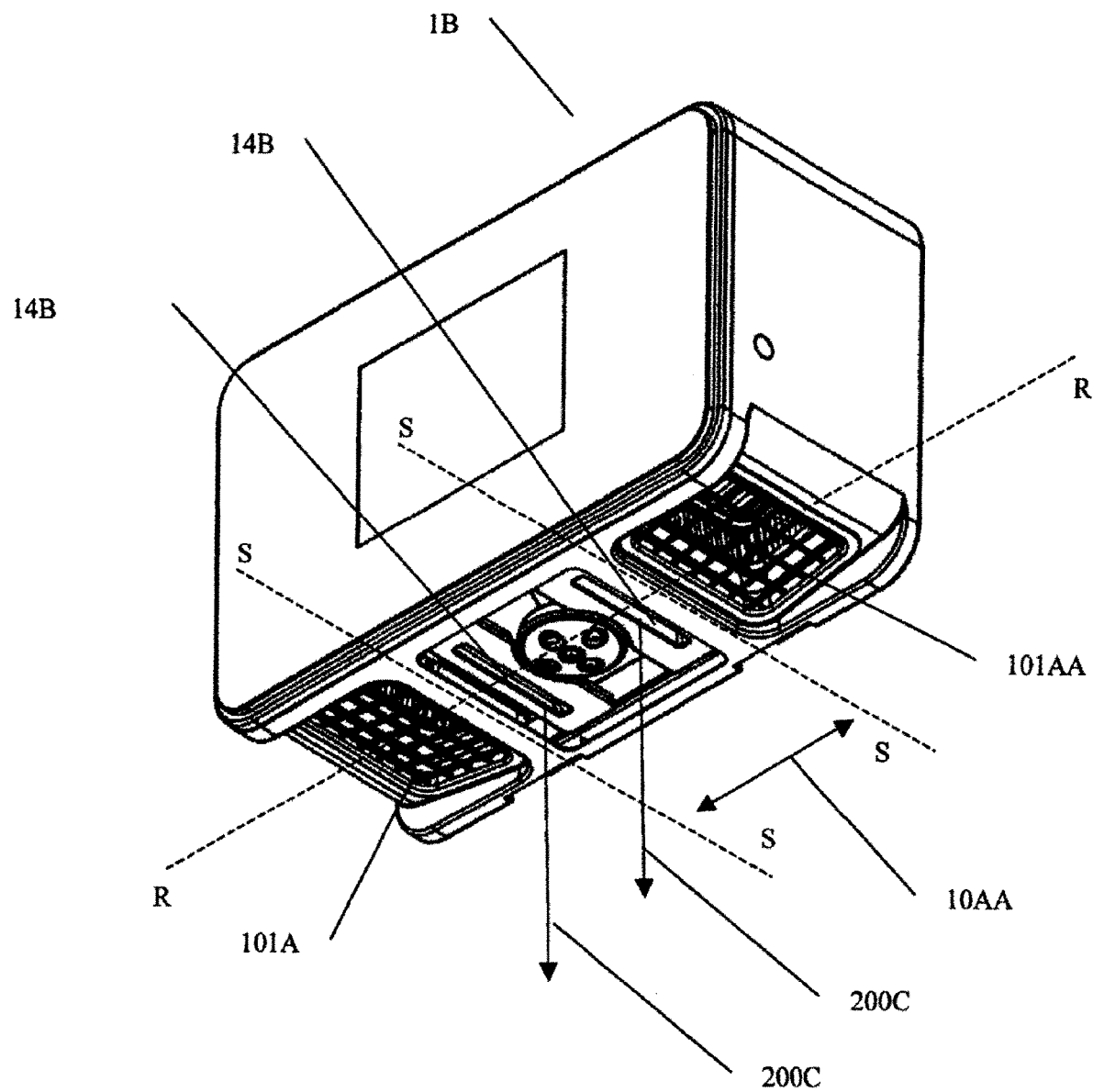
Figure 18:
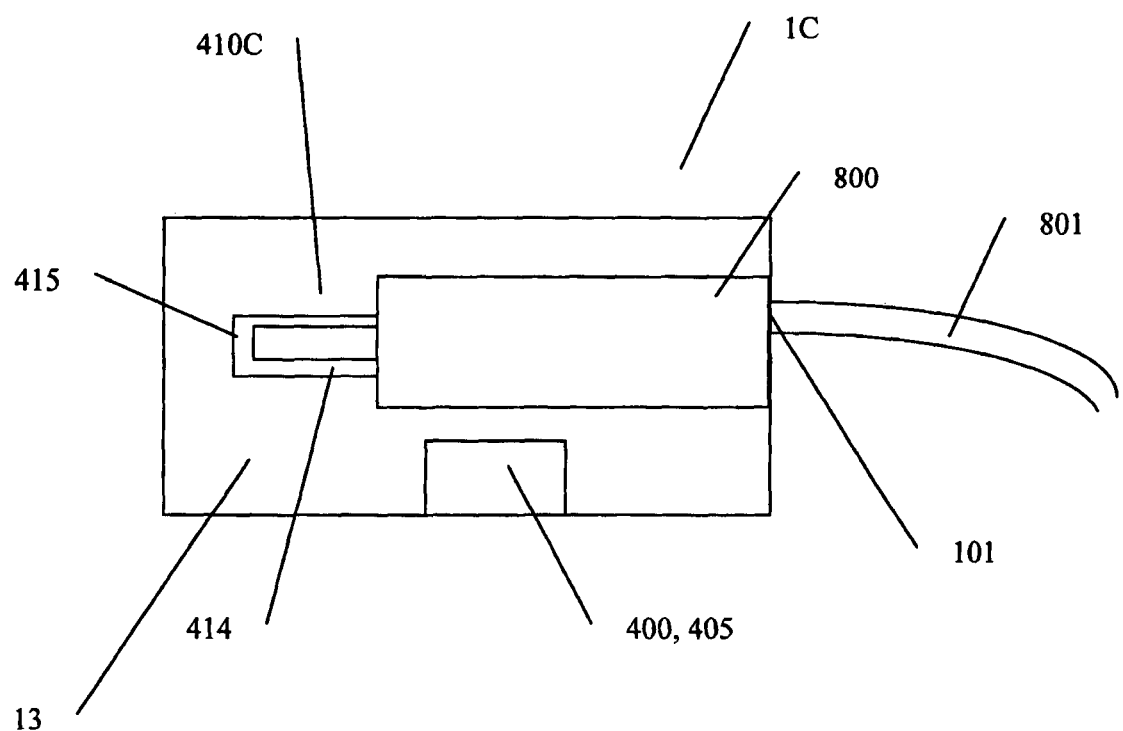

FIG. 4 is a partial perspective view of the embodiment of FIG. 1 shown with its hood in an opened arrangement; the drawing of FIG. 4 is regarded as a partial view in the sense that certain components, relating to a spraying apparatus, have been omitted from the drawing of the dryer in FIG. 4, in order to show the tapered passageway that would otherwise be partially hidden by the presence of the spraying apparatus;

FIG. 5 is a front view of the embodiment shown in FIG. 4, with the hood detached from the base plate. In this drawing of FIG. 5, in comparison to the partial FIG. 4, the spraying apparatus is shown in front of the tapered passageway;

FIG. 6A is a perspective view of a three-dimensional filter used in the embodiment in FIGS. 4 and 5;

FIG. 6B is an exploded perspective view of the three-dimensional filter of FIG. 6A and its tray supporting assembly;

FIG. 6C is a cross-section of a cut-away portion of the three-dimensional filter of FIG. 6A;

FIG. 6D is another cut-away, perspective view of the three-dimensional filter of FIG. 6A;

FIG. 6E is a cross-sectional plan view of the three-dimensional filter of FIG. 6A, with a sub-view showing an enlarged portion;

FIG. 6F is a perspective view of a modified alternative three-dimensional filter that is larger in size compared to the filter of FIG. 6A;

FIG. 6G is a perspective view of a modification to the three-dimensional filter of FIG. 6A in which the filter structure is provided with an external rack for carrying pieces of material to be effused into the airflow;

FIG. 7 is a perspective view of an assembly of a fan housing with an attached tapered passageway, and also shows, attached to this assembly, a filter holder that mounts a filter, and a liquid container support that supports a container of liquid;

FIG. 8A is an exploded view of components that make up the filter holder and the liquid container support shown in FIG. 7;

FIG. 8B shows a modification of the filter holder of FIG. 8A in which multiple fluid reservoirs with wicks are provided;

FIG. 9A is a side view of a first exemplary variant of a pump mechanism used in the embodiment shown in FIG. 5;

FIG. 9B is a perspective view of the variant of FIG. 9A;

FIG. 9C is an underside view of the variant of FIG. 9A;

FIG. 9D is an exploded perspective view of the variant of FIG. 9A;

FIG. 10 is a cut-away perspective view showing an example of a modification of the spray pump mechanism;

FIGS. 11A and 11B show side views of part of the modified spray pump mechanism of FIG. 10;

FIG. 12A to 12D show a sequence of diagrams indicating movement of the modified spray pump mechanism of FIG. 10;

FIG. 12E shows a modification to the modified spray pump mechanism of FIG. 10;

FIG. 13A is a perspective view of the pump-spray motor and rocking arm used in the embodiment of FIG. 10;

FIG. 13B is a side view of the rocking arm of FIG. 10;

FIG. 14A is a partial perspective end view of a further embodiment viewed from beneath when the apparatus is mounted on a wall or upright surface 3, where the modified external casing relates to the modifications shown in FIGS. 10 to 12F;

FIG. 14B is a similar viewpoint to FIG. 14A but showing another embodiment in which the nozzle is fixed in place and does not, in use, reciprocate back and forth;

FIG. 14C is a side view of the modified embodiment of FIG. 14B, where FIG. 14C has cut-away portions to reveal internal components of the modified pump mechanism;

FIG. 15A is a side view, and FIGS. 15B and 15C are perspective view of a further embodiment;

and the following drawings relate to a further modified embodiment of an air purifying apparatus in the form of a hand dryer which has two air intakes, where:

FIG. 16A is a bottom perspective view of yet another embodiment of an air purifying apparatus in the form of a hand cleaner-dryer, where the cleaner-dryer is viewed at an angle from below when the unit is mounted on an upright surface, such as a wall;

FIG. 16B is another perspective view of the embodiment of FIG. 16A, shown notionally mounted on a wall, with its cover opened to reveal internal components;

FIG. 16C is an exploded perspective view of the embodiment of FIG. 16A; and FIG. 16D is a front partial view of the embodiment of FIG. 16A shown with the cover removed to allow a view of parts of the internal components;

FIG. 17A is a front partial view of a further embodiment which is a modification of the embodiment of FIGS. 1 and 16A in that the present embodiment of FIG. 17A is provided with angled inlet apertures;

FIG. 17B is a bottom perspective view of the embodiment of FIG. 17A;

FIG. 18 is an variation of the invention embodied in a vacuum cleaner; and

Figure 3:
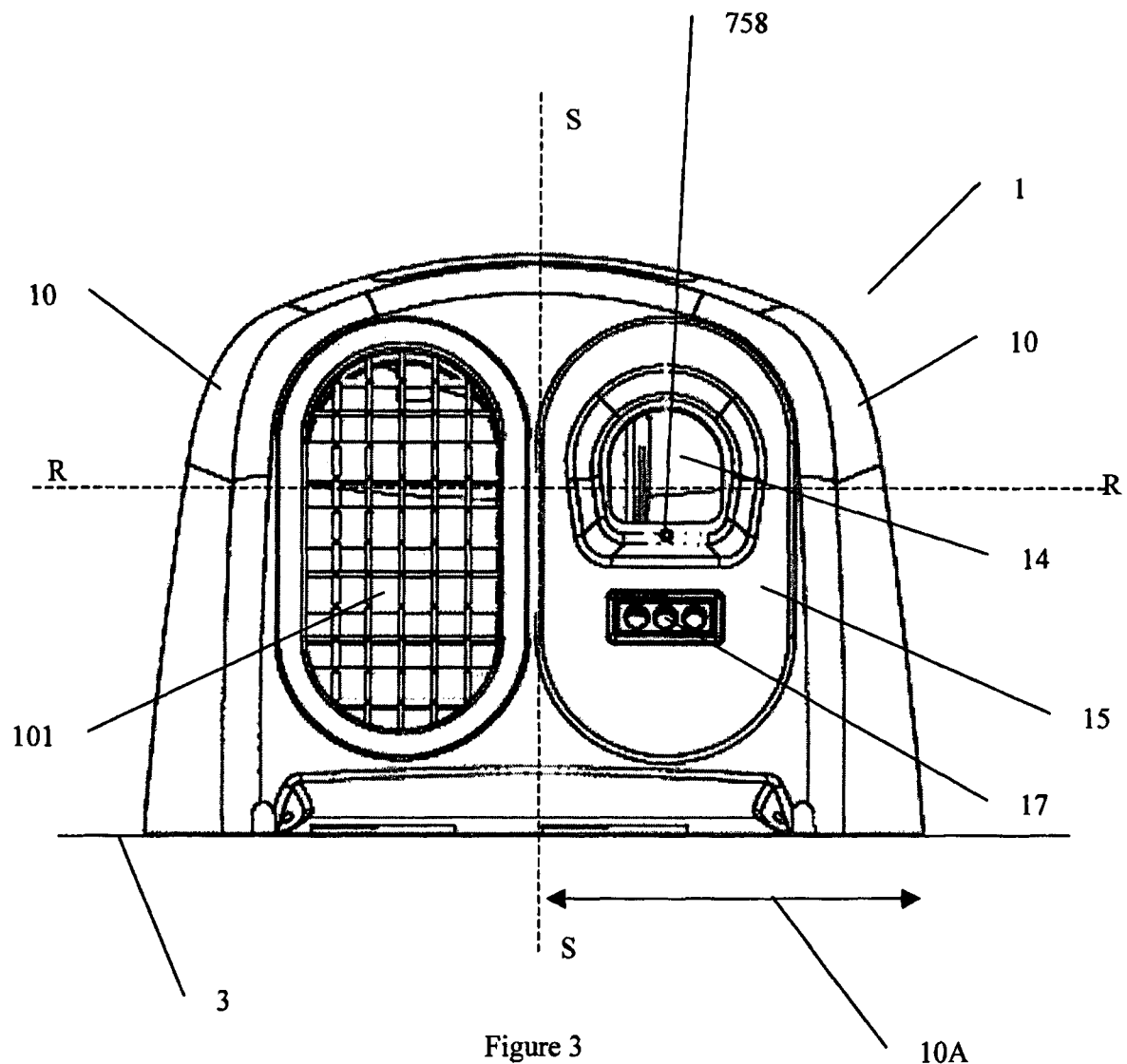
FIG. 3 is an end view or underside of the embodiment of FIG. 1 viewed from beneath when the apparatus is mounted on a wall or upright surface.
Figure 19A:
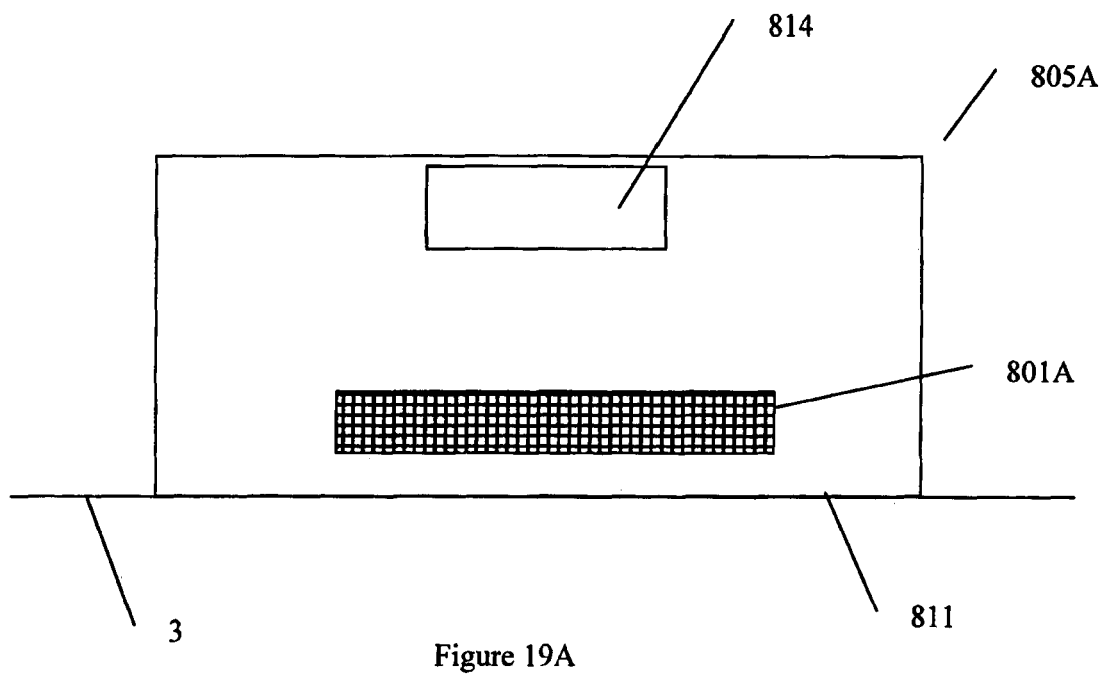
Figure 19B:
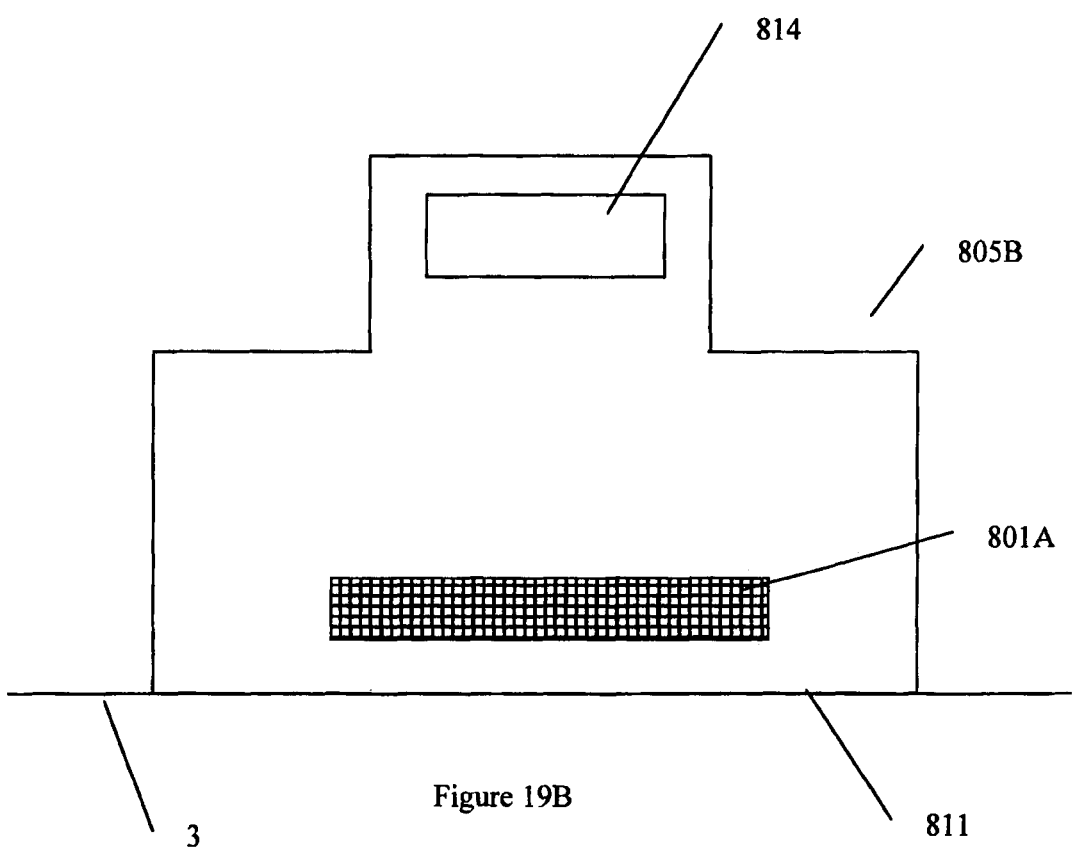

FIGS. 19A and 19B both relate to prior art, and are schematic diagrams of end or underside views a prior art hand dryer or air purifier viewed from beneath when the apparatus is mounted on a wall or upright surface (with these views corresponding to the view in the embodiment of FIG. 3 of the present invention).

In the embodiments, like components are labeled with like reference numerals merely for the sake of ease of understanding the different embodiments and modifications of the various aspects of the invention.

In the description, the reference numeral 200 refers to the airflow, and this numeral with various suffixes 200A, 200B, 200C etc, refer to earlier or later portions of the same airflow that moves through the apparatus, and are not intended to refer to separate independent airflows.

Some of the further embodiments, described below, may comprise a partial modification in only some, but not all, of the components illustrated in an earlier-described embodiment of the invention in this specification.

DESCRIPTION OF EMBODIMENTS

Referring to the accompanying drawings, FIG. 1 shows an embodiment of an air purifying apparatus in the form of a hand dryer 1.

In FIG. 1, the dryer 1, in use, draws in an airflow 200A from a human-activity ambient environment that is frequented by people, and then to expel that purified airflow 200C back into the ambient environment. The airflow 200A is drawn in through an inlet in the form of an inlet aperture 101. The airflow 200C exits the dryer through an outlet in the form of an exit-aperture 14.

The invention is not limited to a particular visual appearance of an inlet aperture and outlet aperture, and may be varied in accordance with other embodiments and modifications.

Examples of human-activity ambient environments, that are frequented by people, include toilets, doctors' waiting rooms, washrooms, rooms in a hospital, rooms for children, rooms for invalids, rooms in homes, to name but a few non-limiting examples.

Such human-activity ambient environments can also include closed environments that experience a high throughput of people such as waiting rooms, elevators, and in public transport such as trains and buses. Different embodiments of the invention are not limited to hand dryers, but may include apparatus of different varieties that can incorporate an air purifying function for a range of human-activity ambient environments.

In FIG. 1, the hand dryer 1 is adapted to expel from the dryer 1 an airflow of substantially sterilized air 200C that can be used, for example, for drying hands. In the exemplary embodiment, the operational range of the heated air may be around 55 to 65 degrees Centigrade, although other embodiments may use whatever temperature is suited for that particular environment. For example, winter climates may require airflows 200C of higher temperatures, while in warmer or tropical climates it may suffice for the dryer 1 to expel an airflow of lower or cooler temperature for drying hands in such warmer climates. The temperature of the airflow may be adjusted to achieve a comfort-level, relative to the ambient temperature, for the user whose hands are exposed to the airflow. In other embodiments that are solely intended to function as air purifiers, no specific heating of the airflow is required.

The hand dryer 1 has a housing. The housing includes a main hood 10 and a base-mounting in the form of a baseplate 11. The baseplate 11 is visible when the dryer 1 is in an open, partial view of FIG. 4. The baseplate 11 is partly visible when the dryer 1 is in a closed arrangement in the side view of FIG. 2.

Figure 2:
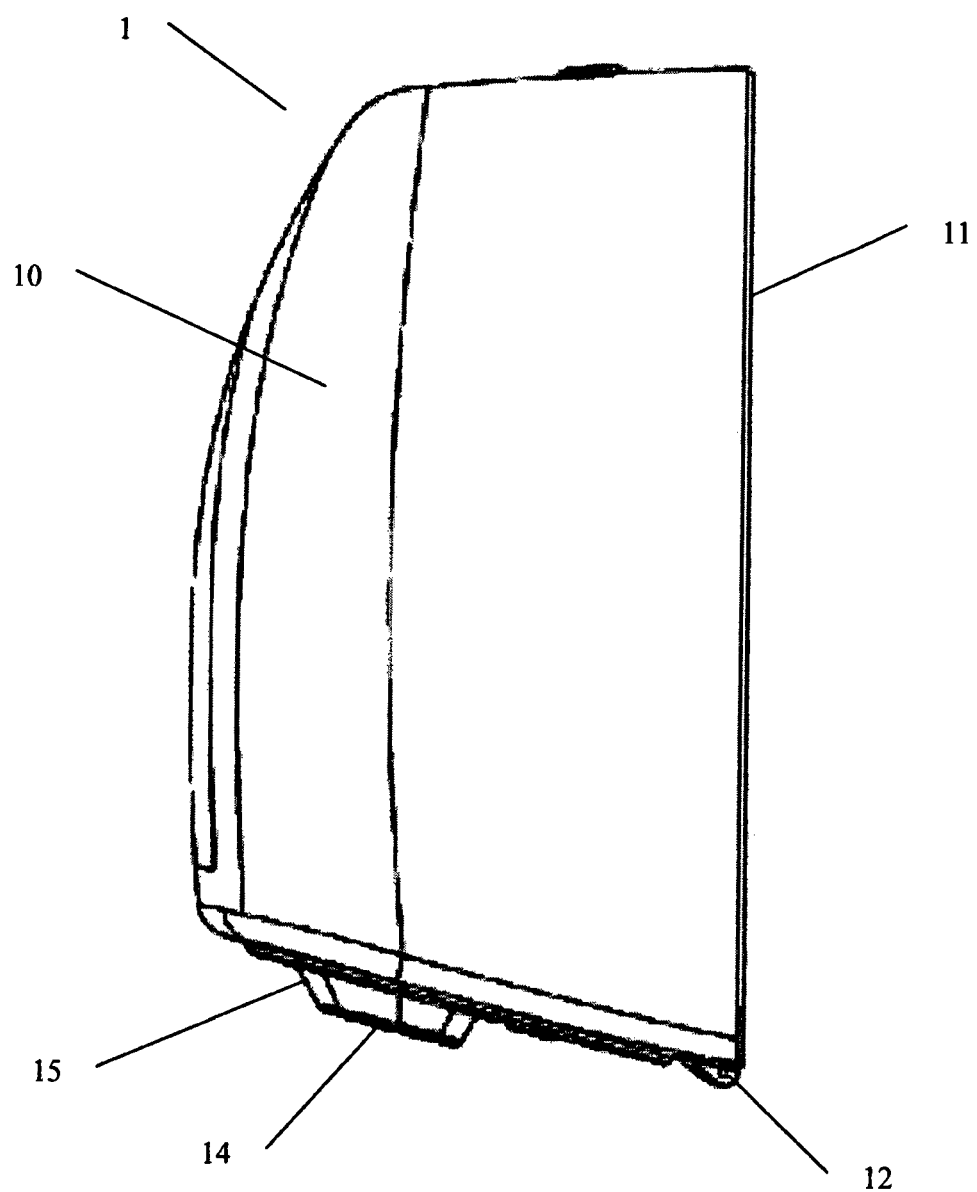
FIG. 2 is a side view of the embodiment of FIG. 1 showing the apparatus with the housing in a closed arrangement.

In FIG. 2 and FIG. 4, the hood 10 is mounted to the baseplate 11 by hinges 12. When the dryer 1 is installed in place for use, the baseplate 11 is secured to a wall or upright surface with screws, bolts or other appropriate fastening mechanism.

FIG. 1 shows the hood 10 arranged in a closed arrangement, which is the arrangement of the dryer 1 when installed in location.

FIG. 4 shows the hood 10 arranged in an opened arrangement.

In the embodiment, the hood 10 and the baseplate 11 of the housing define therein an interior chamber in the form of inner chamber 13. The inner chamber 13 is the interior space that is enclosed by the hood 10 and baseplate 11. FIG. 5 shows a range of components installed within the inner chamber 13.

Further embodiments are not limited to the shape, configuration or size of the housing 1 shown in FIG. 1, and the housings of other embodiments may vary in shape and configuration and many be greater or smaller in size.

During use, when the dryer 1 is operated to dry a user's hands, air from the ambient human-activity environment, in the form of an airflow 200A, is drawn into the inner chamber 13 of the housing 1 where the airflow is purified, and may be heated. The airflow is subsequently expelled onto the user's hands in the outgoing stream 200C of the airflow.

The dryer 1 has two kinds of users of the apparatus: firstly the users who rely on the dryer 1 to dry their hands and to kill germs in order to purify the air in the ambient environment, and secondly the users who maintain the dryer by installing and replacing consumables inside the dryer 1. It is believed that the context of each situation will make it clear as to which user is being described.

In the embodiment of FIG. 1, the incoming airflow 200A is sucked into the hand dryer 1 through the inlet aperture 101.

When the hand dryer 1 is closed, as in FIGS. 1 and 2, the interface of the hood 10 and baseplate 11 is sealed to prevent ingress of airflow, other than through the inlet aperture 101. The air-proof seal between the contact surfaces of the hood and baseplate may be created by a rubber gasket material, resilient polymer, or other form of material that is capable of providing such an air-tight seal.

In FIGS. 1 and 10, the inlet aperture 101 includes a grille structure 102. The grille structure 102 comprises a grid-like arrangement of rods or strips.

When the dryer is closed and in operation, the incoming airflow 200A enters the hand dryer 1 through the inlet aperture 101. For the purpose of illustration only, however, FIGS. 4 and 5, which show an opened arrangement, nevertheless indicate the incoming 200A and outgoing 200C airflow as if the dryer 1 were notionally closed and in use.

Also, in actual use, the airflow that occurs inside and through the dryer 1 has a degree of turbulence.

Fan

In FIGS. 4 and 5, the airflow 200A, 200B, 200C through the dryer 1 is created by airflow-generator in the form of a fan having a rotating fan-blade (not shown). The fan-blade revolves inside a fan-casing 400. Rotation of the fan-blade generates the airflow 200. The rotation of the fan-blade is operated by a fan-motor 405. The fan causes the airflow to flow from the inlet to the outlet. The invention is not limited to a particular shape of fan-blade.

In the embodiment, the fan, which is housed inside the fan-casing 400, is preferably a dual-fan comprising two fan-halves which together are adapted to draw airflow into the fan-casing 400 from two opposite directions.

In FIG. 5, the dual-intake fan draws airflow into the fan-casing 400 from either side of the casing. Having two inlet apertures into the fan-casing 400 provides for a greater rate of airflow into the fan-casing 400, than would be the case with a single aperture.

Hence, in FIG. 5, part of the airflow enters the fan-casing 400 through an aperture located in one side 401A of the casing. Another part of the airflow enters through another aperture in the other side 401B of the casing 400.

The fan is rotated by a fan-motor 405 that is at least partially housed in a motor-housing 403.

Part of the airflow, entering the other side 401B of the fan-casing 400, makes its way to the fan through a number of holes 402 located in the motor-housing 403. As the air enters through the holes 402, the air comes into contact or into proximity with parts of the fan-motor 405, and the airflow is heated to an extent by heat generated from the fan-motor 405.

Another part of the airflow, entering the other side 401B of the fan-casing 400, makes its way to the fan through a gap 407A between an adjacent outer surface of the fan-casing 400 and the motor-housing 403.

Air Heater

In FIG. 1, the dryer 1 may be provided with heating-apparatus in the form of a heating element. In FIG. 4, the heating element is located in a vicinity 20 downstream of where the airflow leaves the fan-casing 400. The heating element includes a grid of wires or plates adapted to be heated electrically when the dryer 1 is required to emit a heated airflow.

The heating element heats up the airstream 200B so that the expelled airflow 200C is sufficiently warm to dry the user's hands.

In other modified embodiments, there may be no need for a separate heating-apparatus. For instance, when the dryer 1 is used in countries with warmer or tropical climates, an airflow that has been warmed merely by heat from the fan-motor 405 may be sufficient to dry the hands comfortably for the user. Alternatively, where the hand dryer 1 is used in colder climates or where the ambient temperature is colder, a separate heating-apparatus, in addition to the heat from the fan-motor, may be provided.

Moreover, in other embodiments, which are not designed as hand dryers, but rather designed to function primarily or solely as air purifiers, in such embodiments there may be no requirement for a separate heating-apparatus over and above whatever heating may occur as the airflow passes through or proximate the fan-motor 405.

Germ-Killing System

In the embodiment of FIG. 1, the hand dryer 1 is provided with airflow-germ-killing-system. The airflow-germ-killing-system is in a form that includes one or more germ-killing sub-systems. These airflow-germ-killing-system sub-systems, either individually, or preferably in combination or combinations, serve the purpose of killing germs in the airflow. Description of embodiments of these one or more sub-systems of the airflow-germ-killing-system are provided below, by way of example only.

In the embodiments, various sub-systems of the airflow-germ-killing-system preferably are adapted to enhance airflow through the dryer 1.

Three-Dimensional Filter

In the embodiment of FIGS. 1, 4 and 5, a sub-system of the airflow-germ-killing-system comprises a three-dimensional filter structure in the form of a three-dimensional filter 410A. The phrase "three-dimensional filter structure" is used to distinguish it from another type of filter that consists of a generally two-dimensional, flat, planar sheet of filter material.

In this specification, the term "three-dimensional filter structure" excludes and should not be construed to refer to microscopic features of the filter, for example, such as would require a microscope to readily discern. For example, the term "three-dimensional filter structure" does not cover microscopic gaps between individual strands or threads in the filter fibre. Hence, in this specification, the term "three-dimensional filter structure" is intended to relate to engineering design characteristics of a part of the apparatus, such as shown in the non-limiting examples in the drawings.

In the embodiment of FIGS. 4, 5, and 6A to 6E, as an example, the three-dimensional filter 410A comprises air-filter-surfaces that define an encompassed filter interior region in the form of a filter interior 411 that is encompassed by the three-dimensional surfaces of the filter 410A.

In the embodiment, by way of example, the three-dimensional filter 410A is shaped as a container or a box having an opening 412 at one side. The three-dimensional filter 410A has semi-circular ends 413. In the embodiment, the filter interior 411 is an encompassed space or region which is bounded by the air-filter-surfaces of the three-dimensional filter 410A, and which has the opening 412 at one side.

The sectional cut-out view of FIG. 6D shows that the three-dimensional filter 410A is formed as a container or a box with one side 412 fully opened.

In this embodiment of the filter of FIGS. 6A to 6E, one entire side of the filter 410A is an opening 412, but in other modifications, the extent of the opening can be varied in terms of how much of the side is left open. For instance, in other modifications, merely part of a side may be opened, or portions or more than one side may be opened. In other words, other embodiments are not limited to a configuration where only one complete side is fully open.

In use, the three-dimensional filter 410A in FIG. 4 is positioned in connection with the inlet aperture, which inlet aperture 101 is seen in FIGS. 1 and 3. In the embodiment, the filter 410A is positioned over the inlet aperture 101 so that all of the airflow 200A, that enters into the dryer 1 through the inlet aperture 101, first enters through the open side 412 and into the filter interior 411, and then passes through the air-filter-surfaces of the three-dimensional filter 410A, and then is dispersed into the of inner chamber 13 of the hand dryer 1. It is through the open side 412 that the airflow 200A, from the inlet aperture 101, is able to flow into the filter interior 411 of the three-dimensional filter 410A.

In other modifications, there may be an internal passageway that connects the three-dimensional filter 410A to the inlet aperture 101, however, such internal passageways are not open to the main chamber 13, since the airflow can only enter the main chamber 13 after it has passed through the three-dimensional filter 410A.

In FIGS. 6A and 6E, the air-filter-surfaces of the three-dimensional filter 410A are in a form that comprise wall-structure. In FIGS. 6A and 6E, the wall-structure is in the form that comprises upright, side filter walls 414.

The air-filter-surfaces are in a form that also comprise ceiling-structure. In FIG. 6A, the ceiling-structure is in the form of a filter ceiling 415. The filter ceiling 415 has semi-circular ends. The side filter walls 414 depend from the rim of the filter ceiling 415. Hence the semi-circular ends of the ceiling 415 correspond in shape to the semi-circular ends 413 of the walls 414.

Referring to FIG. 6A, the filter ceiling 415 has a ceiling-frame 415A. The side filter walls 414 also have a wall-frame 414A. In manufacture, the ceiling-frame 415A may be connected to the wall-frame 414A by any suitable joining mechanism, such as through sonic welding or by the use of adhesives to bond the frames 415A, 414A together, or through the use of mechanical connections.

In the embodiment of FIG. 6D, the opening 412 has generally the same structural shape as the filter ceiling 415.

In the embodiment of FIG. 6D, the side filter walls 414 are generally perpendicular to the plane of the filter ceiling 415.

In FIGS. 6A and 6E, the side filter walls 414 and the filter ceiling 415 combine to define therein the filter interior 411 that is encompassed by the three-dimensional surfaces of the filter 410A.

In the embodiment, the three-dimensional nature of the filter 410A means that it has an encompassed internal volume, having height, length and breadth, which together define the filter interior 411 within the body of the filter 410A. The height of the filter walls 414 determine the height of the filter 410A. The filter interior 411 has a three-dimensional encompassed volume. This is distinguished from a generally flat sheet of filter material which, in this specification, is not regarded as three-dimensional, having no encompassed interior space defined by height, length and, breadth.

In other modifications, the three-dimensional nature of the filter may be such that the wall-structure and ceiling-structure are part of a seamless, contiguous structure, such as a dome or mound. In even further modifications, the three-dimensional nature of the filter may be such that the wall-structure and ceiling-structure are also a contiguous structure, such as a pyramid, cubic, or tent-shaped structure, even having rectangular sides, for example. In all these modifications, the modified three-dimensional filter would include an encompassed filter interior that has a three-dimensional volume. In other modifications, the open side 412 may alternatively be circular, square-shaped, rectangular, oval, or any suitable regular or irregular shape.

In use of the embodiment of FIG. 6D, the airflow 200A enters the dryer 1 through its inlet aperture 101, and then the airflow passes through the opening 412 of the three-dimensional filter 410A and into the filter interior 411. The air in the filter interior 411 is drawn through both the filter ceiling 415 and the upright filter walls 414. Thus, the airflow is dispersed in multiple directions exclusively through the wall and ceiling parts of the air-filter-surfaces of the three-dimensional filter 410A. The airflow 200A is dispersed in multiple directions, for example in the embodiment, by being dispersed straight through the ceiling 415 portions, and also dispersed laterally through the upright, side filter walls 414.

In modified embodiments where the three-dimensional filter structure is in the form of, for example, a dome, pyramid or tent, whether regular or irregular-shaped in each case, the air-filter-surfaces, that are arranged in substantially different orientations, enable the airflow to be dispersed in multiple directions. This is in contrast to airflow that disperses through a flat, sheet-like planar filter in a generally consistent uni-direction.

Compared to a scenario of using a flat, two-dimensional filter to span the inlet aperture 101, in contrast, the three-dimensional filter 410A of the present embodiment has a total combined surface area of the air-filter-surfaces, comprising the ceiling 415 portions and the upright filter walls 414, that provides a substantially and significantly larger surface area for the airflow 200A to enter the dryer 1. The larger effective surface area of walls and ceiling of the three-dimensional filter 410A enables a larger volume of airflow to pass through the filter 410A.

A greater filter surface area offers a larger air-transmission area through which the airflow 200A can pass through the three-dimensional filter 410A.

Without being limited by theory, it is believed that the provision of a greater air-transmission surface area equates to less resistance to the airflow. It is believed that, for a given amount of air that needs to pass through the filter, a filter provided with a greater air-transmission surface area would offer less resistance to the airflow.

Without being limited by theory, it is believe that having less resistance to the airflow may allow a less powerful fan-motor to be used to achieve the required rate of airflow through the hand dryer 1. Less powerful fan-motors, that drive the internal fan, may be linked to a lower degree of noise during use.

Alternatively, the lesser resistance to airflow may be utilized in a different manner, which is to use a more powerful fan-motor to achieve faster rates of airflow than would be possible without such a three-dimensional filter. In this regard, in the example of the hand dryer 1, the fan-motor is preferably a universal motor with a rated speed of 13,000 to 14,000 rpm, which is generally suited for intermittent, stop-start operation. In the example, this higher speed motor configuration provides a very fast throughput of airflow which reduces the time needed for a user to dry his hands. Drying times of less than 11 seconds have been achieved in experimental embodiments, whereas in the marketplace drying times of double that, around 20 seconds, are often considered acceptable.

Another advantage of the provision of greater surface area of such a three-dimensional filter is that it is able to last longer in use before needing replacement, compared to a filter that had less surface area A filter with greater surface area would tend to take longer to reach a point of being clogged up and needing to be replaced.

Another advantage is that the three-dimensional filter, with its larger surface area compared to a flat two-dimensional filter, may offer a greater surface area that can potentially carry a larger amount of anti-germ substance.

Another advantage is that, if all other factors were equal, a filter with greater surface area results in lesser resistance to airflow, which may tend to increase the lifespan of the fan-motor.

Filter Surface Structure

In the embodiment of FIG. 6D, the air-filter-surfaces may comprise a three-dimensional surface structure that is non-flat. In this specification, the phrase "non-flat" is not intended, and should not be construed, to refer to the microscope thread or strand filter structure that would be discernible by a microscope. For instance, a piece of paper is regard as having a flat surface structure, even though under a microscope it would not. Hence, in this specification, the term "non-flat" is to be construed from the same perspective as viewing all the engineering design components as shown in the non-limiting exemplary drawings.

In the embodiment, the non-flat surface structure may be a multi-faceted surface structure. The multi-faceted surface structure further provides a larger effective surface area compared to a totally flat, sheet-like surface. A larger surface area offers a greater surface area through which airflow can pass through the filter.

In the embodiment of the filter in FIGS. 4, 5 and 6A to 6E, the multi-faceted surface structure of the air-filter surfaces may be an undulating structure. The undulating structure may be in a form that has a pleated, corrugated, rippled or zig-zag-shaped structure, any of which would distinguish the undulating surface structure from totally flat sheet material. The undulations may have sharp edges, as shown in example of FIG. 6C, or the undulations may have curved or gently-contoured edges. In other words, the term multi-faceted in this specification includes, but is not limited to, a case where each of the facets is flat, as in the analogy of diamond facets.

In FIG. 6C, the multi-faceted surface structure comprises a corrugated or pleated structure, which are two alternative descriptive terms to describe the same structure shown in FIG. 6C.

In other modifications, the multi-faceted surface structure may comprise either a random or orderly, regular or irregular, pattern of three-dimensional bumps or protrusions on the surface of the three-dimensional filter structure. Such three-dimensional bumps or protrusions would likewise have an effect of increasing the available surface area of the filter through which air can flow, compared to the surface area of a flat, sheet-like surface of similar length and breadth.

In the embodiment of FIG. 6C, the cross-section of both the ceiling 415 portions and the upright filter walls 414 have a corrugated or pleated structure consisting of alternating ridges 416 and grooves 417. The ridges 416 have sharp edges along the length of the ridges. In other modifications, the ridges may have more gently-contoured, curved or rounded edges. For example, in other alternative embodiments, the multi-faceted, three-dimensional surface structure may include a corrugated structure where ridges and grooves are less pronounced, with the structure resembling an undulating wave-like structure.

Although the embodiments of surface structure shown in the illustrated embodiments comprise a regular three-dimensional surface structure, other modifications may comprise an irregular three-dimensional surface structure.

FIG. 10 shows a cross-sectional, cut-away view of the three-dimensional filter 410A of FIG. 5. A difference between the apparatus in each of FIG. 5 and FIG. 10 is that the former incorporates a first embodiment of a pump spray apparatus 700A, while the latter incorporates a second embodiment of a modified pump spray apparatus 700B (the pumps described below).

In other modifications, the overall shape and size of the three-dimensional filter structure can be varied. For example, a modified embodiment in FIG. 6F shows a larger three-dimensional filter 4106 that has a modified overall shape that is different to the filter used in the earlier embodiment in FIG. 4. In the modification in FIG. 6F, the three-dimensional filter 4106 has corrugated walls 414B and ceiling 4156 that have a somewhat more orthogonal three-dimensional structure, without the pronounced semi-circular ends 413 of the earlier embodiment of the filter of FIGS. 4, 5, and 6A to 6E.

For the sake of clarification, although the microscopic structure of the filter material may comprise interwoven fibres that, in other contexts, are regarded as three-dimensional, instead, in this specification, the three-dimensional nature of the filter, and also the nature of its filter surface structure, are regard here as being three-dimensional by having with regard to its overall design macrostructure as shown in the appended drawings, rather than its microstructure.

Filter Insertion

In the embodiment of FIGS. 4, 5 and 6B, and in the filter shown in FIG. 10, the three-dimensional filter 410A is able to be seated on a tray-structure. The tray-structure is in the form of a tray-frame 424 that has semi-circular ends 425, such that the shape of the tray-frame correlates with the cross-section shape of the three-dimensional filter 410A that is able to be seated on the tray-frame 424. The shape of the plan view of the tray-frame 424 corresponds to the shape of the base of the three-dimensional filter 410A.

In FIG. 6B and FIG. 10, the tray-frame 424 has an open central region 428. The open central region 428 is traversed by a grille structure 426. The grille structure 426 comprises an arrangement of crisscrossed rods that span from one side of the frame to the other in a grid-like arrangement. In FIG. 6B, the ends of the rods, of the grille structure 426, are supported by the tray-frame 424. In the cross-sectional view of FIG. 10, a sectional view of the tray-frame 424 is shown with the three-dimensional filter 410A seated thereon.

In FIG. 6B, the tray-frame 424 has a peripheral rim 429. When the filter 410A is seated on the tray-frame 242, the rim 429 prevents the filter 410A from moving from side to side when the airflow 200A passes through the filter 410A.

In the embodiments of FIGS. 5 and 10, the tray-frame 424 is able to slide into place in the hand dryer 1, with the base of the three-dimensional filter 410A attached to the tray-frame 424.

In FIG. 10, the tray-frame 424 has a base portion. The base portion has lateral sides that are each provided with a pair of elongated, outwardly projecting strips 427 that, in use, are able to slide in corresponding elongated grooves in the hand dryer 1. Slotting of the strips 427 into the grooves serves to anchor the three-dimensional filter 410A in order to provide resistance to the force of the airflow that flows through the filter 410A during operation of the hand dryer 1.

When the filter 410A needs to be replaced, the tray-frame 424 is slid out of place, a replacement filter attached to the tray-frame 424, and the tray-frame slid back into place in the hand dryer 1. Thus, the three-dimensional filter 410A, 4106 in its various embodiments, which is seated on the tray-frame 424, is able to be replaceably slid into position.

Multi-Layer Filter

In the embodiment in FIG. 6D, a further sub-system, of the overall airflow-germ-killing-system, relates to the air-filter-surfaces that comprise multiple layers of different filter material. The multiple layers of the air-filter-surfaces are seen in the cross-sectional view of FIG. 6C.

The cut-away, cross-sectional drawings of FIGS. 6C and 6D show that the ceiling 415 portions and the upright filter walls 414 are each made up of multiple layers. Each of these layers comprises a different filter material with distinguishing characteristics. Each of the different layers of filter material perform a different function.

In the embodiment, the layers of different filter material are ordered in a certain sequence, because adjoining layers perform roles that depend on the order of the layers in the sequence of layers.

In the embodiment in FIG. 6D, in the upright filter walls 414 and in the ceiling 415 portion, there is a first layer 418, a second layer 419, and there may be at least a further third layer 420. The layer-sequence will be described, starting with a description of the filter that is nearest to the filter interior 411, and then proceeding to the filter that is next furthest away from the filter interior 411. The first 418, second 419 and the preferred third filter layers 420 are shown in the cut-away drawing in FIG. 6C.

The filters are described in that sequential order because, in the embodiment, the filter interior 411 is where the airflow 200A first enters the hand dryer 1 apparatus. Therefore, as the airflow 200A passes through the air-filter-surfaces of the three-dimensional filter 410A, it is the first filter layer 418, of the layer-sequence, that makes initial contact with the airflow 200A.

First Layer

In the sequence of layers, the first filter layer 418 comprises: a germ-killing filter layer in the form of germ-killing filter 418.

The expression, first layer, is used to describe the germ-killing filter 418 because this is the first layer of the three-dimensional filter 410A that, in use, initially encounters the incoming airflow 200A.

The incoming airflow 200A, which is drawn from a human-activity ambient environment, contains germs.

The first filter, the germ-killing filter 418, carries germ-killing substance. As the incoming airflow 200A passes through the first filter 418, germs in the airflow are killed in the first germ-killing filter 418.

The germ-killing substance, carried by the first germ-killing filter 418, can be any suitable substance that is adapted to kill germs in the airflow 200A. Examples of suitable germ-killing substances are as follows: Nano-$TiO_2$, nano $SiO_2$ and nano $ZnO_2$. An example of a filter material used for the first germ-killing filter 418 consists of: 77% polyester and 19% polypropylene fibres, together with 2.6% nano-$TiO_2$, 0.7% nano $SiO_2$ and 0.7% nano $ZnO_2$. The embodiment is not limited to this particular type of filter, and other appropriate antibacterial filter material may be used.

It is appreciated, however, that embodiments of the invention are not limited to any particular germ-killing substances being carried in the germ-killing filter layer, and can be varied and adapted depending on the nature of germs that are encountered in a particular ambient environment.

Second Layer

The second layer 419 of the three-dimensional filter 410A is the second in the layer-sequence that the incoming airflow 200A encounters as it moves through the three-dimensional filter 410A.

The second layer 419 comprises a germ-killing-substance interception filter layer that intercepts or substantially intercepts the germ-killing-substance that come from the first layer 418.

In the embodiment in FIG. 6D, the germ-killing-substance interception filter layer comprises a filter layer that is impregnated with charcoal or carbon.

An example of a filter material used for the second layer 419 consists of a nonwoven mix of functional polyester and bonding bicomponent fibers with polyester core and co-polyester sheath, impregnated with ethylacrylate-vinylchloride-copolymer, polyfosfate flame retardant, activated carbon powder and black pigment. The embodiment is not limited to this particular type of filter, and other appropriate carbon or charcoal-impregnated filter material may be used.

When the airflow 200A moves through the air-filter-surfaces of the three-dimensional filter 410A, a portion of the germ-killing-substance may come off the first filter 418 and thus enter the airflow. Some germ-killing-substance, which are deadly to germs, may likewise be harmful to humans. Hence, the carbon or charcoal in the second layer 419 intercepts any germ-killing substance that comes from the first layer 418. As a consequence, the second layer 419 prevents, or at least minimizes, the amount of germ-killing-substance that is allowed to be carried by the airflow into the inner chamber 13 of the hand dryer 1.

The impregnated carbon or charcoal in the second layer 419 is also able to remove smells and odors from the airflow. For example, some germ-killing substance, that are needed to kill highly toxic germs, may themselves have malodors or smells. Hence, the charcoal may also remove or at least minimize the extent of those smells in the airflow that enters the inner chamber 13 of the hand dryer 1. Thus, as a result of the second layer 419, the airflow that enters the inner chamber 13 is able to be substantially free of malodours.

Third Layer

In the embodiment, the three-dimensional filter 410A may be provided with a third layer 420 which comprises: a material entrapment layer that entraps at least any filter material that come from or is released from the first filter layer 418 or from the second filter layer 419.

In the embodiment, as the airflow 200A flows through the first two filter layers 418, 419, microscopic fibers or particles, originating from the material from which the first 418 and second 419 filter layers are made from, may be released into the airflow 200A. If these microscopic fibers or particles in the airflow were to be released in the outgoing airflow 200C that exits from the hand dryer 1, then, once these are released into the ambient environment, these minute objects may cause irritation, for instance, in the nasal passages or eyes of people in the human activity environment. Such microscopic fibers or particles may be particularly irritating to people that suffer from allergies.

In the embodiment, in this third layer 420, the material entrapment layer includes anti-fiber-migration filter material. The material entrapment layer includes a fiber material that is able to entrap the said material that may emanate from the first 418 and second 419 filters.

An example of an anti-fiber-migration filter material comprises a polyester fabric of greater than 85% polyester component, and less than 15% binder resin. The third layer 420 of the embodiment is not limited to this particular filter material, and other suitable materials may be used based on their ability to intercept said material that may emanate from the first 418 and second 419 filters.

Layers: Modifications

In other modified embodiments, the first, second and third layers may be embodied, not merely as discrete layers, but alternatively may be in the form of functional layer-regions. For instance, a modified embodiment may have two or more initial sub-layers that both perform the function of killing germs. In this example, the two germ-killing sub-layers combine to form a first functional layer-regions. Each of the sub-layers, in this first functional layer-regions, may carry a different germ-killing substance for killing different variety of germs. In other words, the first layer-region is not restricted to being just one layer, but may have two or more layers having similar functional characteristics.

Likewise, the second layer-region may have two or more layers each sharing similar functions.

Likewise, the preferred third layer-region may have two or more layers each sharing similar functions.

Interchangeable Anti-Germ Material

In FIG. 6B, the airflow-germ-killing-system of the hand dryer 1 may optionally include a further germ-killing sub-system that comprises germ-killing-substance positioner in the form of a mounting structure 421, 422, 423. This germ-killing-substance positioner is a preferred feature that is not necessarily present in all embodiments.

The mounting structure is able to position one or more sources of one or more air-diffusible germ-killing-substances inside the filter interior 411.

The air-diffusible germ-killing-substances are characterized in their ability to air-diffuse upon engagement with any airflow in the filter interior 411. Before air diffusion occurs, each of the one or more sources is initially in the form of a solid or gel. Then, when the airflow 200A flows over the air-diffusible germ-killing-substances, the substances are diffused into the airflow, mostly by an evaporation mechanism.

The mounting structure includes tablets 421 that have an outer frame 422. In the embodiment, the air-diffusible germ-killing-substances is in the form of a block of gel that is carried inside the frame 422. The frame 422 has an internal mesh (not shown) that acts as a web that transverses the region within the frame 422. The gel is formed around this mesh. The mesh prevents the gel from falling off the frame 422.

In the embodiment, the mounting structure also includes clasping mechanisms 423 located on the rods of the grille structure 426. The frames 422 are mounted on the grille structure 426 by engaging with the clasping mechanisms 423.

FIG. 6B shows, for example, three such sources of air-diffusible germ-killing-substances in the form of air-diffusible anti-bacteria tablets 421A, 421B, 421C.

In the embodiment of FIG. 6B, the active germ-killing-substance may be in the form of an air-diffusible gel. In use, as the airflow 200A rushes over the tablets 421, the germ-killing-substance on each tablet progressively diffuses in the stream of airflow 200A that rushes over the tablets, thus infusing the airflow with the germ-killing-substance to kill the associated germs in the airflow.

Optionally, there may be multiple sources where each of the tablets 421A, 421B, 421C is provided with a different germ-killing-substance that kills different types of germs.

A range of available air-diffusible germ-killing-substances may be used for the tablets 421A, 421B 421C, and their selection depends on their known properties for killing the type of germs in a particular ambient human-activity environment.

For example, in FIG. 6B, there are shown three such tablets 421A, 421B, 421C, and these three tablets may each be carrying the same germ-killing-substance, or alternatively each of the tablets may each carry a different substance each designed to combat different type of germs.

In the embodiment of FIG. 6B, there is a synergy between the germ-killing first filter 418 of the three-dimensional filter 410A which, in this embodiment, acts in tandem with the optional air-diffusible anti-bacteria tablets 421A, 421B, 421C.

On one hand, the first germ-killing filter 418 of the three-dimensional filter may be suited for carrying germ-killing-substance for killing germs that are of a ubiquitous variety, which are encountered week in week out. The germ-killing-substance on the first layer, the germ-killing filter 418, is capable of lasting for a long time, such that the three-dimensional filter 410A tends not to have to be replaced frequently.

On the other hand, the optional mounting structure 421, 422, 423 enables tablets to be interchanged and replaced as often as needed. This interchangeability also provides a degree of customization, which enables different germ-killing-substance to be placed in position, or later replaced with other different substances. For example, epidemic-level germs, such as the SARS or H1N1 virus, can tend to prevalent for a limited season. Hence, administrative operators of the hand dryer 1 can insert customized tablets 421, as the need arises, to adapt and respond to newly discovered threats of emerging viruses.

Moreover, in a preferred embodiment, the ability to optionally mount the tablets 421A, 421B, 421C, each having different germ-killing substances thereon, enables the administrative operators of the hand dryer 1 to utilize tablets carrying two or more different germ-killing substances so as to combat several types of major prevailing viruses at the same time, rather than being limited to using only one type of germ-killing substance at a time.

Also, it is observed that the germ-killing substances, often needed to combat highly virulent viruses, such as the H1N1 virus, may also be toxic to humans. Hence, the ability to position these human-toxic anti-bacteria tablets 421A, 421B, 421C inside the internal filter interior 411 of the three-dimensional filter 410A means that any human-toxic substances, diffused off the tablets 421 into the airflow 200A, may be intercepted by the second layer 419 of the three-dimensional filter 410A.

It is noted that these tablets 421A, 421B, 421C ideally would not be used to carry fragrance or perfume since these substances would be trapped or intercepted by the charcoal layer in the second filter 419, thus nullifying the influence of the fragrance in the airflow 200C emitted from the dryer 1 back into the human activity environment.

FIG. 6G is a perspective view of a modification to the three-dimensional filter of FIG. 6A in which the filter structure is provided with an external rack 430 for carrying pieces of preferably fragrance-effusing material 431 to be effused into the airflow. The fragrance material is placed outside of the three-dimensional filter 410A so that the fragrance material is not intercepted by any of the layers of that filter 410A, particularly the second layer which is impregnated with carbon or charcoal.

Wick

In the embodiment of FIG. 7, the airflow-germ-killing-system of the hand dryer 1 may optionally include a further germ-killing sub-system that comprises a wick-delivery-system.

In the embodiment of FIG. 7, the wick-delivery-system is in a form of a wick filter arrangement 612 that includes an air wick 600. The air wick 600 is able to effuse an anti-bacterial, germ-killing liquid that is stored in a replaceable container. The replaceable container is in the form of one or more replaceable bottles 610.

In FIG. 7, part of the airflow enters the fan-casing 400 through the aperture that is located in the one side 401A of the casing which is located further away from the motor-housing 403. The air wick 600 is positioned in front of the aperture in the side 401A of the fan-casing 400 which is located further away from the motor-housing 403.

The air wick 600 is arranged so as to be dipped in the liquid that is inside the bottle 610. As airflow 200 in the inner chamber 13 flows past the wick 600 as it enters the fan-casing 400, the liquid in the bottle 610 is drawn up through the wick and is dispersed into the airflow as it enters the fan-casing 400.

In the embodiment of FIG. 7, the wick filter arrangement 612 also includes a filter holder 611 that is able to support a further germ-killing-substance interception filter layer in the form of wick filter arrangement 612.

The wick filter arrangement 612 may comprise one or more layers of filter that performs a similar role to the second layer 419 of the three-dimensional filter 410, namely to intercept or substantially intercept the germ-killing-substance in the airflow that comes from the wick 600, before the airflow enters the fan-casing 400. For a non-limiting example of a filter material useable with this filter holder 611 for interception of germ-killing substances, see the example given above use with for the second layer 419 of the three-dimensional filter 410A, since the function of both of these filters is to intercept germ-killing substances.

FIG. 8A shows an exploded view of the wick filter arrangement 612, comprising the wick 600 that is attached to the bottle 610, the filter 613, and the filter holder 611. The filter holder 611 has a pair of resilient pincers 614 that are adapted to hold the neck of the bottle 610. The filter 613 is provided with a slot 615 that fits over the pincers 614. When assembled, the bottle 610 is held by the pincers, and the filter is held by the pincers.

The wick filter 613 is also able to intercept moisture in the airflow, for instance any moisture emanating from the wick 600, so as to minimize the likelihood of moisture being in the air by the time the airflow reaches the optional heating element. In the embodiment, as mentioned, the optional heating element is located in the vicinity 20 downstream of where the airflow exits the fan-casing 400.

In other modifications, the filter holder 611 may also support a further material entrapment layer that performs a similar role to the third layer 420 of the three-dimensional filter 410, namely to entrap at least any filter material that come from the material of the wick filter 613. For a non-limiting example of a filter material useable with this further material entrapment layer, see the example given above use with for the third layer 420 of the three-dimensional filter 410A.

FIG. 8B shows a further modification where multiple fluid reservoirs 610 with wicks 600 are provided. Having multiple reservoirs enables a user to infuse a wider range of materials into the airflow. For instance, one bottle may contain an anti-germ or anti-bacteria fluid, while the other bottle may contain a fragrance liquid.

In a further possible modification, the wick 600 and bottle 610 may be placed inside the filter interior 411 that is within the three-dimensional surfaces of the filter 410A, 410B. In such a modification, the three-dimensional filter 410A, 410B is made of sufficient size to accommodate the wick and bottle within. An advantage of such an embodiment is that any harmful substances, distributed by the wick, can be subsequently intercepted by the charcoal filter material in the second layer 419 of the three-dimensional filter 410A.

The embodiment in FIG. 5, in contrast to the modification in FIG. 7, omits the wick 600 and bottle 610, indicating that the wick mechanism is a preferred feature that is not necessarily present in all embodiments.

Examples of germ-killing-substance in liquid form that can be delivered by the wick mechanism, include known available anti-bacterial liquids that can be effused into the air to kill germs, and the embodiment is not intended to be limited to any one type of substance for this purpose.

Selection of Different Options of Delivery

In the exemplary embodiments, the air wick 600 in FIG. 7 and the tablets in FIG. 6B are preferred features.

The wick filter arrangement 612 in the exemplary embodiment of FIG. 7 is useful for delivering substances that are ideally delivered from a liquid source, such that the liquid substance is stored in the bottle 610 for delivery into the airflow via the wick.

The tablet system in the exemplary embodiment of FIG. 6B is useful for delivering substances that are ideally delivered from a solid source, such as a gel.

Hence, in various embodiments, the decision on whether to include a wick or tablet system may be influenced by the nature of substance that needs to be delivered into the airflow, and/or depending perhaps on the nature of germs that need to be killed in a particular ambient human-activity environment.

Spray

In FIG. 5, the airflow-germ-killing-system of the hand dryer 1 may optionally include a further germ-killing subsystem in a form that may include germ-killing-substance-sprayer. Several exemplary, non-limiting variants of germ-killing-substance-sprayer will be described below by way of example only.

Spray Pump Variant 1

FIG. 5 shows a germ-killing-substance-sprayer in the form of a pump spraying apparatus 700A.

A function of the pump spraying apparatus is to emit a brief burst of spray of anti-bacterial liquid into the airflow 200C that exits the dryer 1.

Although several embodiments are described below, the embodiments of the invention are not limited to any one of these exemplary spray mechanisms, since other variations can be proposed to achieve a similar pumping spray action. (In the partial illustration of FIG. 4, the pump spraying apparatus 700A has been omitted from the cut-away diagram in order to show, in the illustration, the tapered passageway 16 which are located behind the pump spraying apparatus 700A when all assembled).

In FIG. 5, the pump spray apparatus 700A introduces yet further germ-killing-substance, in the form of a liquid anti-germ substance, to the airflow by spraying the germ-killing substance into the airflow. The spray liquid comprises an anti-bacterial germ-killing liquid, and may also include a fragrance liquid provided that there is no chemical reaction between the anti-bacterial liquid and the fragrance substance.

Preferably, this further germ-killing-substance is sprayed into the airflow at a location where the germ-killing-substance does not become coated on surfaces of the apparatus itself. In the embodiment of FIG. 5, the pump spray apparatus 700A is arranged to spray the liquid anti-germ substance into the airflow at a point where the airflow has already exited the hand dryer 1.

In the embodiment, the liquid anti-germ substance is sprayed in such a way that the anti-germ substance from the spray apparatus 700A emerges through a spray-outlet in the form of spray aperture 758, and enters the airflow where the airflow is already outside the dryer 1 mingling with the ambient human-activity environment. The spray apparatus 700A sprays the anti-germ substance into the airflow that is already outside of the apparatus 1 so that the force of the airflow carries the substance onto the user's hands when the users expose their hands to the exiting airflow 200C.

In other words, the anti-germ substance from the spray apparatus 700A is preferably not sprayed inside the apparatus 1 itself. This is to minimize the likelihood of build-up of the sprayed anti-germ substance on internal surfaces of the dryer 1, which could otherwise occur if the anti-germ substance were to be sprayed into the airflow while the airflow is still inside the dryer 1.

Alternatively, in a yet further embodiment, the spray apparatus 700A may spray the liquid anti-germ substance directly onto the user's hands, however, even in such a modified embodiment, the substance is sprayed in such a manner that it avoids or substantially minimizes the substance reaching and coating surfaces of the apparatus 1 itself.

In the embodiment, the liquid anti-germ substance may be a non-alcohol-based liquid, since it is found that the airflow around the person's hands, as the liquid is blown onto the hands, is sufficient to dry the liquid without the added effect of alcohol evaporation.

In other embodiments, if desired, the liquid anti-germ substance may be an alcohol-based liquid which is able to rely on alcohol evaporation to expedite drying of the liquid on the user's hands.

The liquid anti-germ substance, that the spray apparatus 700A sprays onto the user's hands, may be a mild antiseptic substance, and not a powerful toxic anti-germ substance which could inadvertently be toxic or irritating to humans.

In the embodiment of FIG. 5, the pump spray apparatus 700A includes a pumping mechanism that is able to be activated to emit a brief burst of spray.

In this first exemplary variant of the pumping mechanism, in FIG. 5 and FIGS. 9A to 9D, the pumping mechanism includes a solenoid-driven pump mechanism. The hand dryer 1 is provided with a microprocessor and electrical circuit that is programmed to determine when to instruct and activate the solenoid 750A, 750B to drive the pump.

In FIG. 9A, the pump spray apparatus 700A includes a reservoir container 751 supported on a circular holder 752. The reservoir container 751 is able to hold a quantity of liquid such as an anti-germ substance in liquid form. In other modifications, the anti-germ liquid substance may also include a fragrance mixed into the anti-germ liquid.

In FIG. 9D, the container 751 is provided with an exit nipple 753 which engages with a corresponding hole 754 in a nozzle cap 755. The nozzle cap 755 presses on an internal spring-loaded pump tube, whereby pressing on the nozzle cap 755 causes a pumping action. Each depression of the cap 755 draws out an amount of liquid from the container 751. To emit several bursts of spray, the nozzle cap 755 is pressed several times for as many times as are required.

The hole 754 in the nozzle cap is connected via an internal channel to an exit nipple 756. A thin tube 757 connects the exit nipple 756 to the spray aperture 758.

In FIG. 9D, the solenoid includes two reciprocable components 750A, 750B. Activation of the solenoid causes the outer one of these two components 750B to move so as to press against the nozzle cap 755. This pressing action causes an amount of liquid to be pumped out of the container 751, through the internal channel, then through the thin tube 757, and finally to be sprayed out through the spray aperture 758. The spray aperture 758 is shaped to cause the liquid to be emitted as a fine mist of droplets of the liquid.

In FIG. 9C, the exit-facia plate 15 is provided with a circular hole 759. The liquid sprays from the spray aperture 758 through this circular hole 759.

In FIG. 9C, the exit-facia plate 15 is provided with an aperture 19 that enables sensors 17 to have a clear line of sight to the region where the user's hands would be placed when using the hand dryer 1. In various modifications, the number of sensors 17 can be varied. In the variant in FIG. 3 there are three sensors 17, while in the variant of FIG. 9C there are two sensors, although the number of sensors may be modified.

Spray Pump Variant 2

In FIG. 10, a second exemplary variant of a pumping mechanism makes use of an eccentric drive to perform the act of intermittently pressing against a modified nozzle cap 755A to activate a burst of spray.

FIGS. 11A and 11B show the eccentric drive 760 that moves a rocking arm 763 that intermittently presses on the nozzle cap 755A to emit a spray.

The sequence of diagrams in FIGS. 12A to 12D illustrate the movement of the rocking arm 763 that enables the arm to intermittently press against the nozzle cap 755A.

In the embodiment of FIGS. 11A and 11B, the nozzle cap 755A is provided with a spray-outlet in the form of an atomizer spray duct 758A. When the rocking arm 763 presses on the nozzle cap 755A, a small burst of liquid is emitted from the spray duct 758A. The liquid is drawn from an internal reservoir container that resides inside the reservoir shell 701 of the modified pump spray apparatus 700B.

As the rocking arm 763 presses on and lifts off the nozzle cap 755A, the spray duct 758A reciprocates back and forth. Hence, in the embodiment of FIG. 14A, the exit-facia plate 15, of that particular modification, is provided with an elongated aperture 759A to reveal the spray duct 758A. The aperture 759A is elongated so as to reveal the spray duct 758A throughout the range of its reciprocal motion.

Consequently, in the modification in FIG. 12E, the nozzle cap 755A is provided with a semi-cylindrical shield 755B. The shield 755B fits across whatever portion of the elongated aperture 759A that is not taken up by the spray duct 758A. The shield 755B seals the aperture 759A to prevent ambient air entering from the aperture 759A into the inner chamber 13. The seal, created by the shield 755B and the elongated aperture 759A, may be enhanced by a resilient gasket material or other suitable methods of enhancing seals to prevent ingress of air.

In FIG. 12A to 12E, and FIGS. 13A and 13B, the eccentric drive 760 is formed around an axial shaft 761 of a spray-pump motor 762. The eccentricity of the drive 760 imparts a rocking motion to the pivotal rocking arm 763 that has a lower end 764. The lower end 764 is adapted to press against the nozzle cap 755A.

FIG. 11A shows an arrangement where the nozzle cap 755A is not depressed by the end 764 of the rocking arm 763.

FIG. 11B shows the same arrangement with the nozzle cap 755A is depressed by the end 764 of the rocking arm 763 that causes liquid to be sprayed through the atomizer spray duct 758A.

In use, when a user places his hands underneath the hand dryer 1 to dry his wet hands, the sensor or sensors 17 detect the presence of the hands. An electrical control circuit instigates the pump spray apparatus 700B to emit one or more bursts of sprayed liquid.

In the embodiment, electrical control circuit includes a spray-stop-start system comprising a combination of components, as described below:

In the rotational sequence in FIGS. 12A to 12D, the shaft 761 rotates around its axis. The circular cross-section of the eccentric drive 760 is not concentric with the axis of the shaft 761. Rather, the circular cross-section is biased towards one lateral side of the axial shaft 761. Therefore, as the shaft 761 rotates axially, the biased portion of the body of the eccentric drive 760 moves around the axis of the shaft 761.

(For illustration sake only, in FIG. 12A the body of the eccentric drive 760 generally points around 3 o'clock; in FIG. 12B the eccentric drive 760 generally points around 6 o'clock; in FIG. 12C the eccentric drive 760 generally points around 9 o'clock; in FIG. 12D the eccentric drive 760 generally points around 11 o'clock; which brings the eccentric drive 760 back to its starting position generally around 3 o'clock in FIG. 12A.)

In order to communicate to the spray-stop-start system that a burst of spray has been emitted, the shaft 761 is provided with a laterally projecting tab 765. The end of the tab carries a small magnet, and this magnet rotates in a circular path as the tab 765 rotates with the axial shaft 761. In the embodiment, the magnet is a rare earth magnet.

In FIGS. 11B and 12B, a Hall-sensor 766 is positioned in front of a window 767 that is positioned on a portion of the circular path of the magnet. The Hall-sensor 766 is part of an electrical circuit on a printed circuit board 768 of the electrical control circuit that is housed in the body of an internal component of the apparatus.

The Hall-sensor 766 is able to detect the magnetic field from the magnet on the tab 765, each time the tab rotates past the window. In FIG. 12C, the arrangement is such that the tab 765 passes the Hall-sensor 766 at or proximate the point when the rocking arm 763 presses on the nozzle cap 755A to emit the spray. Thus, each passing of the tab 765 over the Hall-sensor communicates to the control mechanism of the electrical circuit that a single burst of spray has been emitted.

Each 360 degree rotation of the eccentric drive 760 equates to one rocking motion of the lower end 764 of the rocking arm 763, which equates to one press of the pump, which equates to a single spray emitted from the spray duct 753A.

Thus, each single full rotation of the shaft 761 corresponds to one pump action that emits one burst of spray. Hence, the rotation of the tab 765 tells the control mechanism that one pump action has been effected, and thus the motor can stop gradually rotating.

Thus, FIG. 12A shows the rocking arm 764 in its rest position. When a user places his hands beneath the hand dryer 1, the spray-stop-start system instructs the spray-pump motor 762 to start rotating, and it does so according to the rotational sequence of FIGS. 12B to 12D. When the tab 765 rotates past the Hall-sensor 766, the spray-stop-start system instructs the spray-pump motor 762 to gradually stop rotating such that it comes to back to its rest position shown in FIG. 12A. In the embodiment, this is achieved by the electrical control circuit gradually decreasing the electrical current to the spray-pump motor 762 such that decelerates to a halt in its resting position of FIG. 12A.

In the embodiment of FIG. 1, each time the user places his hands under the hand dryer 1, either one or preferably two bursts of spray are emitted. In other embodiments, any number of bursts may be emitted as is considered desirable under the prevailing conditions.

In the embodiment, electrical control circuit instructs the spray-stop-start system instigates the emission of two bursts of spray, and the timing is such that a period of a few seconds elapses between the two bursts, for instance, five seconds in between each burst of spray.

The spray can be activated at various times, depending on the intended outcome for the spray for each embodiment and modification. For example, in one scenario example, the spray may be required merely to be sprayed into the airflow to cover a user's hands with the liquid anti-germ substance. In such a scenario, the embodiment can includes the sensors 17 which identify when a user's hands are placed beneath. The embodiment includes an electronic circuit that connects the sensors 17 to the activation mechanisms of the pump spray apparatus 700A, so that the pumping mechanism is activated periodically during the timeframe that the sensors 17 detect that the user's hands remain under the hand dryer while the user is drying his or her hands.

In another scenario example, the apparatus 1 is embodied merely as an air purifier, for instance, that is designed to purify the ambient air in a living room or a public area. In such a scenario, the embodiment can includes an electronic timing circuit that periodically and simultaneously activates, firstly, the fan-motor 405 that drives the fan inside the fan-casing 400 and, secondly, also activates the pump spray apparatus 700A to add the liquid substance into the outgoing airflow 200C. In various such embodiments, the sprayed liquid substance may be an anti-germ substance or a fragrance substance.

In a preferred further embodiment of FIG. 12E, the spray duct 758A is preferably positioned at the distal end of a protrusion 754. In the embodiment, the length of the protrusion 754 allows the spray duct 758A to be positioned slightly away from internal regions of the hand dryer 1. Within the internal regions of the hand dryer 1, air is sucked into the fan-casing 400, and this movement of air towards the fan in the fan-casing 400 is experienced, to varying degrees, throughout the internal regions of the hand dryer 1 that are in communication with the inner chamber 13. Therefore, the preferred protrusion 754 is able to position the spray duct 758A slightly away from the main inner regions of the hand dryer 1. Even though, in the further embodiment, the protrusion 743 is only about 2 mm, it is found that such a small extra distance aids to minimize the likelihood of sprayed substance being substantially sucked back inside the hand dryer 1.

In other embodiments, the position of the printed circuit board 768 may be re-arranged in other locations inside the inner chamber 13. In other embodiments, preferably the printed circuit board 768 is located in a position inside the chamber 13 where it is not directly underneath a potential source of liquid, such as directly beneath the replaceable bottles 610, or the internal reservoir container that resides inside the reservoir shell 701. In normal usage, it is not anticipated that there would be any leakage from such sources of liquid, however, as a precaution again un-intended failure of such liquid containers or liquid sources, the printed circuit board 768 is preferably located away from directly under these liquid sources, should any leakage occur, so as to avoid damage to the electrical circuitry.

Spray Pump Variant 3

In FIG. 14B, a third exemplary variant of a pumping mechanism is a modification which is provided with a stationary spray duct 758C that slightly protrudes from the undersurface of the exit-facia plate 15. The stationary spray duct 758C is arranged to spray its liquid into the outgoing airflow 200C.

FIG. 14C shows cut-away portions of the variant of FIG. 14B. A rocking arm 763 rocks backwards and forwards in a manner described for the earlier embodiment. The lower end 764 of the rocking arm 763 intermittently presses on a head of a plunger assembly 755C. Such depression of the plunger assembly 755C causes a burst of liquid to be emitted from the stationary spray duct 758C. The liquid is drawn from an internal reservoir container that resides inside the reservoir shell 701 into the plunger assembly 755C. A thin tube 757 connects the plunger assembly 755C to the stationary spray duct 758C.

Placement of Anti-Germ Material and Substances

Preferably, any anti-germ substance used in the first layer 418 of the three-dimensional filter 410, or in the filter interior 411 of the three-dimensional filter 410, for example the tablets 421, is able to be substantially toxic to humans. This is because any such toxic materials are entrapped by the second layer 419 of the filter 410.

In contrast, preferably, any anti-germ substance used elsewhere in the filter interior 411, the airflow path and outside of the three-dimensional filter 410, is substantially non-toxic to humans. For example, any anti-germ material effused off the air wick 600 would be substantially non-toxic. Also, any anti-germ liquid sprayed by the pump spraying apparatus 700A onto a user's hands would consist of substantially non-toxic material. There reference to "substantially non-toxic" means that the materials are regarded as non-toxic when used according to prescribed guidelines, since such non-toxic substances may become toxic when used outside of guidelines for that particular material.

Exit of Airflow

In partial FIG. 4, and in partial FIG. 5, after the airflow 200A emerges from the top and lateral sides of the three-dimensional filter 410, the airflow 200B moves within the inner chamber 13 until the airflow is sucked and drawn into the fan-casing 400.

In FIG. 7, after the airflow is drawn into the fan-casing 400, the airflow 200C travels through the elongated, tapered passageway 16 until the air is exits the hand dryer 1 through the exit-aperture 14 which is located at the end of an elongated, tapered passageway 16.

The tapered passageway 16 is shown in partial FIG. 4 and FIG. 7, and partially obstructed from view in FIG. 5. The exist-aperture 14 is located in an exit-facia plate 15. The exit-facia plate 15 is snap-fastened to the hood 10 by resilient claws 18.

Note that FIG. 4 is, in a sense, a cut-away or partial drawing because, in FIG. 4, parts of the embodiment have been omitted from the drawing merely in order to show the tapered passageway 16, whereas FIG. 5 provides a normal view in which the tapered passageway 16 is partly obstructed from view by the components.

Air Freshener

In other embodiments, the air purifying apparatus may be embodied, instead of a hand dryer 1, but rather as an air purifier or air freshener.

In an embodiment of an air purifying apparatus, which is in the form an air purifier or air freshener, the apparatus and its components are substantially represented by the example given in the hand dryer 1, with the following preferred modifications:

1) An induction motor is used since the activity of an air purifier or air freshener can require the apparatus to purify airflow for considerably longer time periods than an embodiment in the form of a hand dryer. An induction motor is more suited to this manner of operation than a universal motor. For instance, where a hand dryer might operate for less than a minute while the user dries his hands, an embodiment in the form of an air purifier or air freshener may operate, for instance, for an hour or so or longer, to continuously purify the ambient atmosphere of the human-activity environment.

2) The motion sensor 17 may be arranged to detect motion in the wider vicinity around the apparatus, for instance, a person entering the room in which the air purifier or air freshener is installed, as compared to a hand dryer 1 where its motion sensor system is intended to detect the presence of a user's hands directly under the hand dryer.

Alteration of Airflow Path Size

In operation of the hand dryer 1, the fan, which is housed in the fan-casing 400, generates an internal airflow 200B that is instrumental in transferring the anti-bacteria substances from various components of embodiments of the germ-killing system: such as the germ-killing filter 418 of the three-dimensional filter 410A, the anti-bacteria tablets 421A, 421B, 421C, and the air wick 600.

Without being limited by theory, in the exemplary embodiments, it is found that the speed or rate of airflow over or through these components can influence the efficiency with which the anti-bacteria substances are transferred from the components into the airflow. Moreover, each type of component, from which the anti-bacteria substances emanate, may have an optimum airflow that differs for each components. Also, the rate of airflow throughput, and the speed of the airflow over each of the components, are influenced by a number of parameters, including such as: the power of the fan-motor, the shape of the spaces through which the airflow passes, the total volumetric size of the inner chamber 13, to name a few such parameters. Another relevant factor may be the level of noise which is generated by the fan-motor for any given rate of airflow throughput, with a tendency of higher noise levels being associated with faster motor speed.

Hence, in each exemplary embodiments and in further modifications, there may be required some degree of experimentation to identify an achievable rate of airflow that is judged to be an optimum, having regard for the performance of each of the anti-bacteria-emitting components operating with that one rate of airflow throughput through the apparatus, as well as regard for the noise-level of the fan-motor.

Therefore, the embodiment may be provided with an airflow-path-size-alterable arrangement which enables adjustment of the size of the path through which the airflow passes.

The embodiment of FIG. 4 and FIG. 5, and the embodiment in FIGS. 15A-C, is provided with airflow-path-size-alterable arrangement that enables adjustment of the size of at least part of the airflow path within the dryer 1.

In the embodiment, the airflow-path-size-alterable arrangement is in a form that includes a gap-adjustment plate 404 that enables adjustment of the size of the gap 407A. Adjustment of the size of the gap 407A either increases or decreases the size of the path through which airflow passes to reach the fan.

The fan-motor 405 and motor-housing 403 are supported on the gap-adjustment plate 404.

The plate 404 has one or more apertures through which parts of the fan-motor 405 connect to the fan that is inside the fan-casing 400. For example, the fan-motor 405 has a rotating shaft that imparts rotation to the fan. The shaft passes through an aperture in the gap-adjustment plate 404. Part of the airflow passes through the holes 402 of the motor-housing, and then through the aperture or apertures in the plate 404, en route to the fan in the fan-casing 400.

The gap-adjustment plate 404 is attached to the fan-casing 400 by a number of supporting posts 406. In the embodiment, there are four such posts 406, but the number can vary in other modifications, for example, there may be three or four posts or other forms of support.

In the embodied examples of FIG. 4, 5, 7, 15A, 15B, the airflow-path-size-alterable arrangement may be in the form of, or may include, an arrangement that facilitates adjustment of the gap-adjustment plate 404. The embodiment is not restricted to one particular mechanism for enabling adjustment of the size of the gap 407A. In the embodiment of FIG. 5, and the embodiment in FIGS. 15A, 15B and 15C, adjustment of the gap 407A may be achieved by the selection of varying thickness of ring-like gaskets 408. The ends of the posts 406, have narrowed ends which receive the ring-like gaskets 408. The gap-adjustment plate 404 is provided holes that each correspond with the location of one of the posts 406. The gap-adjustment plate 404 is seated on the set of posts 406, with the gaskets 408 sandwiched in between. Selection of thicker gaskets causes the gap 407A to be wider, while selection of thinner gaskets causes the gap 407A to be thinner.

In the embodiment, the gaskets 408 are preferably made of a resilient material such as natural rubber, artificial rubber, or a resilient polymer suitable for use as a resilient gasket. The resilient gaskets are able to at least partially absorb vibrations from the fan-motor 405.

In the embodiment, the gap 407A is about 10 mm, and in the example it is found that adjustments in the gap size in the order of around 10 to 20 mm, for example, may result in a noticeable change in the rate of airflow inside the inner chamber 13. This example of a 10 mm gap size, however, is not prescriptive for every other embodiment because experimentation is required in each configuration.

In a further example, in the modification of FIGS. 15A, 15B and 15C, the airflow-path-size-alterable arrangement may also include, or may be in the form of a modified filter holder 611A that is provided with slits 407B which act as pathways for the airflow to pass through en route to the fan that is inside the fan-casing 400. In the arrangement, the airflow-path-size is alterable by interchanging the filter holder 611A with a replacement holder that has a different sized flow path. The difference in flow path size can be achieved by modifying the replacement holder to have larger slits and/or an increased number of slits.

In the embodiment of FIGS. 15A, 15B and 15C, airflow passes through the two slits 407B en route to the fan in the fan-casing 400.

As the airflow passes through the slits 407B into the fan-casing, that airflow passes across the inner face of the filter 613 that is carried by the modified filter holder 61 VA.

Thus, at the filter holder 611A, part of the airflow passes directly through the filter 613, and another part of the airflow enters through the side slits 407B to pass across the rear face of the filter 613. Without being limited by theory, it is believed that movement of airflow, across the inner or rear face of the filter 613, partially contributes to the drawing of airflow through the front of the filter. (In FIGS. 15A, 15B and 15C, the inner or rear face of the filter is that portion that is closer to the fan-casing).

The one or more side slits 407B are adapted to allow, in use, a portion of the airflow to enter the filter holder through the one or more side slits 407B so as to pass across a rear face of the filter 613 while, in use, another portion of the airflow enters through the filter 613, such that the passage of airflow through the one or more side slits 407B serves to draw the airflow through the filter 613.

In the embodiment of FIGS. 15A, 15B and 15C, preferably there are two side slits 407B.

In other modifications, preferably there are two slits 407B, but the number of slits 407B in the modified filter holder 611A may vary from having one slit to having several slits.

Preferably, as shown in FIGS. 15A, 15B and 15C, the two side slits 407B are provided only on one hemispherical half of the modified filter holder 611A, and not around the entire circumference or rim. Without being limited by theory, it is believed that having slits only on one side contributes to a smoother airflow behind the inner face of the filter, thus avoiding a tendency for greater turbulence if the airflow were to enter through slits at opposing sides, for example.

In referring to the provision of slits 407B only on one hemispherical side, it is understood that, in use, the one hemispherical side may be positioned at any location on the rim of the filter holder. In FIGS. 15A, 15B and 15C, the slits are positioned on a lateral side of the filter holder, but in other modifications the slits may be positioned at a lateral top or bottom of the filter holder.

In the embodiment, the combined flow paths, firstly provided by the gap 407A between the plate 404 and the fan-casing 400, and secondly provided by the slits 407B in the modified filter holder 611A, can be adjusted to achieve a desired rate of airflow through the dryer 1.

The inner chamber 13 is a sealed enclosure, with the inlet aperture 101 being the only air inlet aperture and the exit-aperture 14 being the only air exit. Therefore, preferably, the rate of airflow through the dryer 1 is set such that the amount of airflow 200A entering the apparatus is roughly equivalent to the amount of airflow 200C exiting the apparatus, in order to avoid fluctuations in pressure in the inner chamber 13 of the hand dryer 1.

Water-Less Hand Washing

FIG. 16A shows yet another embodiment of an air purifying apparatus in the form of a hand cleaner-dryer 1A. The hand cleaner-dryer is adapted to be used in a method of water-less washing of hands, however, there are some spheres of activity where washing of hands with water brings with it a set of disadvantages.

Bacteria and germs breed and live in water. Without being limited by theory, it is believed that, when users wash their hands with water and do not properly dry their hands, a result is that the bacteria can be carried particularly in the moisture that remains on the hands. Even the drying of hands with paper towels can leave amounts of moisture on hands that can encourage bacteria growth on the hands.

Normally, a user washes his hands with water, and then may use a hand drying apparatus to dry the hands in the stream of air.

In contrast, in the embodiment of FIG. 16A, a method of waterless washing of hands involves dousing the user's unwashed hands with a large quantity of anti-germ liquid, and using a high-speed stream of substantially germ-free air to dry the hands rapidly.

The hand cleaner-dryer 1A has a baseplate 11A that is able to be mounted on a wall during installation.

The embodiment of FIG. 16A is provided with two sets of components of an airflow-germ-killing-system both working in parallel in order to deliver the large quantities of anti-germ liquid and germ-free airflow onto the hands when implementing a system of water-less washing of hands.

Large quantities of anti-germ liquid are stored in two large internal reservoir containers 701A.

In use, airflow 200A enters the hand cleaner-dryer 1A through an inlet in the form of two inlet apertures 101A, and each stream of airflow immediately enters one of the larger three-dimensional filter 410B, described above in relation to FIG. 6F.

In an analogous manner to the operation of the embodiment shown in FIGS. 1, 4 and 5, the present embodiment of FIG. 16B operating on the basis of the airflow being purified by passing through the larger three-dimensional filter 410B, and then entering into the inner chamber 13A of the hand cleaner-dryer 1A, and then bring drawn into a pair of fan-casings 400A, and then being expelled as an airflow 200C of substantially germ-free air from the cleaner-dryer 1A through a pair of tapered passageway 17A. The outgoing airflow 200C is directed onto the user's hands.

In the example embodiment of FIG. 16A, the hand cleaner-dryer 1A is provided with modified embodiments of an airflow-germ-killing-system which have been described by way examples with reference to the earlier embodiment of FIG. 1.

For example, in the embodiment of FIG. 16A, the intakes to the fan-casings 400A may be provided with a wick-delivery-system such as in the examples described with reference to FIGS. 8A and 8B.

Rotary Spray

In the embodiment of FIG. 16A, the hand cleaner-dryer 1A is provided with germ-killing-substance-sprayer in a form that has a spray-outlet. The spray-outlet is in a form of an arrangement of several atomizer spray ducts 758B. In FIG. 16A, five spray ducts 758B are arranged on a duct-support 749. Each of the spray ducts 758 are shaped to spray liquid in a roughly cone-shaped trajectory. On the duct-support 749, each of the spray ducts 758 is arranged to spray liquid in a different direction in order to allow the liquid to hit the user's hands in a range of varied directions.

In a modified embodiment, the duct-support 749 may be rotated as spray is emitted from its spray ducts 758. In other modifications, the direction of rotation of the duct-support 749 may be intermittently and periodically changed, for example, from clockwise to anti-clockwise.

In FIG. 16B, the several atomizer spray ducts 758B receive anti-germ fluid from the two large reservoirs via thin tubes 757A (which are not shown, for the sake of clarity, in the exploded view of FIG. 16C or the partial view of FIG. 16D).

For the embodiment of FIG. 16A, in use, when a user places unwashed hands underneath the hand cleaner-dryer 1A, a large quantity of anti-germ liquid is expelled on the user's hands via the several atomizer spray ducts 758B. The outgoing airflow 200C of substantially germ-free air is used to dry the user's hands. In such a manner, the user's hands are able to be washed and dried without the use of water.

In FIG. 16D, each of the inlet apertures 101A, 101AA has a plane B-B1, B-B2 that defines the front face of its opening. For each of the apertures 101A, 101AA their respective planes B-B1, B-B2 are perpendicular to the central axis A-A, such that the face of each inlet apertures points directly downwards in the direction of the central axis A-A. In other words, in FIG. 16D, the plane B-B1 of one of the inlet apertures is co-planar with the plane B-B2 of the other of the inlet apertures.

Dual Direction Inlet Apertures

FIG. 17A shows another embodiment of an air purifying apparatus in the form of another hand dryer 1B.

In the embodiment of FIG. 17A, the incoming stream 200AA of the airflow is sucked into the hand dryer 1B through an inlet.

In FIG. 17A, the inlet is in the form of two inlet apertures 101A, 101AA. The two inlet apertures 101A, 101AA each draw in part of any incoming airflow 200AA in a lateral direction relative to a central axis AA of the housing of the hand dryer 1B.

Each of the inlet apertures 101A, 101AA draws in part of any incoming airflow 200AA from a different direction relative to other of the inlet apertures. Thus, in FIG. 17A, one 101A of the inlet apertures draws in airflow from the left side of the axis A-A, while the other 101AA of the inlet apertures draws in airflow from the right side of the axis A-A.

The two inlet apertures 101A draw in the incoming airflow laterally from the right hand side and left hand side of the central axis of the housing when mounted on a wall.

In this embodiment, the inlet apertures 101A are arranged so as to receive air from either side of the hand dryer 1B when mounted on a wall, in contrast to the embodiment of FIG. 1 which is arranged to receive air generally from directly beneath the apparatus.

Each of the inlet apertures 101A, 101AA has a plane B-B1, B-B2 that defines the front face of its opening. For each of the apertures 101A, 101AA their respective planes B-B1, B-B2 are not perpendicular to the central axis A-A, in order that the face of each inlet aperture points, to a degree, away from the central axis, and not directly downwards in the direction of the central axis A-A. In other words, in FIG. 17A, the plane B-B1 of one of the inlet apertures is not co-planar with the plane B-B2 of the other of the inlet apertures. This is in order to maximize the area from which air can be actively drawn into the apparatus from the ambient human-activity-environment.

In further modifications, the number inlet apertures may be increased beyond two apertures. For instance, a modified unit may have four inlet apertures, with the faces of the inlet apertures all pointing in a variety of directions to maximize the area from which air can be actively drawn into the apparatus from the ambient human-activity-environment.

In other embodiments the angle of the plane B-B can be varied from just a few degrees from being perpendicular to the axis A-A, all the way to the plane B-B being parallel to the axis A-A.

An advantage of having an inlet, in the form of multiple inlet apertures which point in different directions relative to the axis A-A, is that the inlet apertures are thus able to draw in contaminated air from a wider region of the ambient human activity environment so as to be more efficient at purifying the ambient atmosphere of germs.

Arrangement of Inlet & Outlet

Prior art FIGS. 19A and 19B are schematic diagrams of end views a prior art hand dryer or air purifier viewed from beneath when the apparatus is mounted on a wall 3 or other upright surface. In each case, in the known hand dryers 805A, 805B in FIGS. 19A and 19B, when the apparatus is installed on the wall for use, the arrangement of the apparatus is such that the inlet 801A is in between the wall 3 and the outlet 814. Without being limited to theory, it has been found that such an arrangement, resulting from the design of the known hand dryers 805A, 805B, tends to result in a significant build-up of dirt and grime on the exterior parts of the hand dryers 805A, 805B.

In contrast, in embodiments of the present invention in FIGS. 3, 16A and 17B, when the hand dryers and other air purifiers 1, 1A, 1B are mounted on a wall 3 or other upright surface, the arrangement of each of the apparatus is such that the respective inlet apertures 101, 101A, 101AA are not in between the wall 3 and the outlet 14 or whatever form of outlet each embodiment provides.

Rather, in FIGS. 3, 16A and 17B, in each embodiment, the inlet is alongside the outlet.

In the embodiments of FIGS. 3, 16A and 17B, each apparatus has a baseplate 11, 11A. In each embodiment, the respective inlet apertures 101, 101A, 101AA are not in between the baseplate and the outlet 14 or whatever form of outlet each embodiment provides.

In FIGS. 1, 2 and 3, the inlet 101 is not between the outlet 14 and the baseplate 11. Both the inlet and the outlet are on the underside of the apparatus.

In FIG. 16A, the two inlets 101A are not between the outlets 14A and the baseplate 11A.

In FIG. 16B, the two inlets 101A, 101AA are not between the outlets 14B and the baseplate of the embodiment of FIG. 16B.

Another way of describing the arrangements in FIGS. 3, 16A and 17B is that each inlet and outlet is arranged on the underside generally in a row or sequence where the direction of the row or sequence is generally alongside the base-mounting.

For example, in FIG. 3, the general direction of the row or sequence is shown as dotted line R-R. This direction R-R is generally alongside the baseplate 11 that is also alongside the wall 3.

For example, in FIG. 17B, the general direction of the row or sequence is also shown as another dotted line R-R. This direction R-R is generally alongside the baseplate 11 that is also alongside the wall 3.

Substantial Size of Inlet.

By way of background, the airflow 200C that exits each air purifier 1, 1A, 1B has been purified, and so the exiting airflow 200C will not contribute substantially or at all to build-up of dirt on the underside of the dryer 1, 1A, 1B. Indeed, in use, the strength of the outgoing airflow 200C deters un-purified air of the incoming airflow 200A from contacting a region of the underside that is proximate the outlet apertures 14B. In this specification, this general region that is, in effect, largely shielded from any incoming airflow 200A by the force and flow of the outgoing airflow 200C, is referred to by definition as an outgoing-airflow-protected-surface-region.

In the example of FIG. 3, the approximate region of the outgoing-airflow-protected-surface-region is regarded as being the entire half of the underside of the hood 10 indicated by the arrow 10A and dotted line S-S.

In another example of FIG. 17B, the approximate region of the outgoing-airflow-protected-surface-region is regarded as being around the central portion of the underside of the hood 10 indicated by the arrow 10AA and the dotted lines S-S.

Build-up of dirt and grime occurs as the un-purified incoming airflow 200A passes across surface area of the hood 10 and its underside, over a period of time, resulting in a build-up of dirt on these surfaces that are in regular contact with the un-purified incoming airflow 200A.

In this regard, in the exemplary embodiments in FIGS. 3, 16A and 17B, on the surface where the outlet and inlet are positioned, it is preferable that the inlet aperture or apertures 101, 101A occupy a very substantial portion of the surface that is outside the outgoing-airflow-protected-surface-region. The effect is to minimize the amount of exposure to the incoming airflow 200A experienced by the underside surface that is outside the outgoing-airflow-protected-surface-region. In other words, it is a minimization of the amount of surface area on which dirt can accumulate.

Germ-Killing-Liquid-Substance Modified Embodiment

In a modified embodiment, a variant of the germ-killing-substance-sprayer of the dryer is provided with, and is thus able to spray, a germ-killing-liquid-substance. The germ-killing-liquid-substance is sprayed into the outgoing airflow 200C in order for the germ-killing-liquid-substance to reach and sufficiently coat the user's hands.

In the modification, the germ-killing-liquid-substance preferably contains a disperser. In the modification, the disperser plays a role in enhancing the dispersal of at least one or more antimicrobial agents on the skin of the user's hands.

Without being limited by theory, it is believed that the disperser acts as a carrier for at least one or more germ-killing components of the germ-killing-liquid-substance. As the disperser is carried by the airflow 200C onto and dispersed over the user's hands, the disperser effectively aids in the dispersal of one or more germ-killing components over the skin of the user's hands.

Preferably, the disperser comprises one or more surfactants, optionally including one or more super surfactants. The disperser may include an alkyl glucoside. Preferably, the disperser includes one or more glucosides, such as Decyl Glucoside and/or Octyl Glucoside.

The mixture further includes at least one antimicrobial or biocide substance. The biocide may include one or more quaternary ammonium compounds. Preferably, the mixture includes a first biocide substance in the form of a quaternary ammonium salt of the formula:

$$\left[ R1 - \underset{\underset{R2}{|}}{\overset{\overset{R}{|}}{N}} - R1 \right]^+ \quad X^-$$

Ar is an optionally substituted aryl or heteroaryl group

Preferably, Ar N selected from optionally substituted phenyl, benzyl, napthyl and pyridyl groups. Most preferably, Ar is an optionally substituted aryl group. Most preferably Ar is an optionally substituted benzyl group.

R Is any C6 or above unsubstituted branched or linear alkyl group

Preferably, R is any C8 or above unsubstituted branched or linear alkyl group. More preferably, R is any C12 to C20 unsubstituted branched or linear alkyl group. Most preferably, R is any C12 to C20 unsubstituted linear alkyl group. Particularly preferred, R is an unbranched unsubstituted C18 alkyl group.

Each group R1 is independently selected from any C1 to C4 branched or unbranched unsubstituted alkyl Preferably, R1 are each Independently selected from methyl, ethyl, propyl, butyl and isopropyl. More preferably, R1 are each methyl groups.

X is a halide anion.

Preferably X is a chloride, bromide or Iodide anion. Most preferably, X is a chloride anion.

Still more preferably, the mixture includes a quaternary ammonium salt of the formula:

$$\left[ R1 - \underset{\underset{CH_3}{|}}{\overset{\overset{CH_3}{|}}{C}} - CH_2 - \!\!\!\bigcirc\!\!\!\!-\!\!R2 \right]^+ \quad X^-$$

R1 is C8, C10, C12, C14, C16, C18, preferably C12, C14

R2 is H or C1-C5, preferably H

X is Br, Cl or F, preferably Cl

Most preferably, the first biocide substance is an Alkyl Dimethyl Benzyl Ammonium Chloride (BAC).

The mixture preferably further comprises a second biocide substance. The second biocide substance may be a cationic biocidally active surfactant. The second biocide substance is optionally taken from the group including alkyl dimethyl benzyl ammonium (C8-C18), dialkyl dimethyl ammonium (C8-C12) and didecyl methyl polyethoxyethyl ammonium and trimethyl ammonium. Most preferably, the second biocidal substance is in the form of Didecyl Dimethyl Ammonium Chloride (DDQ) having the formula:

$$\left[ H_{21}C_{10}-\underset{\underset{CH_3}{|}}{\overset{\overset{CH_3}{|}}{N}}-C_{10}H_{22} \right]^+ Cl^-$$

The ratio of the first biocide substance and the second biocide substance may be between 1:2 and 2:1, more preferably 1:1, and most preferably is 4:6.

Advantageously, the germ-killing-liquid-substance, including the disperser, includes a precise mixture of 3 active biocide substances.

Accordingly, in a preferred form of the invention, the mixture includes a first biocide substance in the form of Alkyl Dimethyl Benzyl Ammonium Chloride (BAC), and a second biocide substance in the form of Didecyl Dimethyl Ammonium Chloride (DDQ).

Preferably, the ratio of the first biocide substance and the second biocide substance may be between 1:2 and 2:1, more preferably 1:1, and most preferably is about 4:6.

Preferably, the third biocide substance is a biguanide.

The third biocide substance may comprise a substance of the formula:

$$-\left[\underset{H}{\overset{}{N}}-\overset{\overset{NH}{||}}{C}-\underset{H}{\overset{}{N}}-\overset{\overset{NH_n}{||}}{C}-\underset{H}{\overset{}{N}}\right]-$$

where n is 1 or 2.

The third biocide substance more preferably comprises a guanide having the formula:

$$-\left[NH-C-\underset{}{\overset{\overset{NH}{|}}{}}-\underset{+}{\overset{\frown}{}}-\overset{\overset{NH}{|}}{C}-NH-(CH_2)_n\right]_n- Cl_n^-$$

where n is the number of monomers consistent with stabilised micelles in the range of 1-100 nm, preferably 5-10 nm.

Preferably the third biocide substance is therefore polyhexamethylene biguanide. The ratio of the third biocide to the combination of the first two biocidal substances may be between 1:2 and 2:1, more preferably between 2:3 and 3:2 and most preferably is about 1:1.

The disperser may also include at least one inactive ingredient. The inactive ingredient may be a surfactants. The surfactant is preferably an alkyl glucoside. Still more preferably, the inactive ingredient includes one or more of DecylGlucoside and OctylGlucoside. This or these inactive ingredients are preferably effective to stabilize the mixture. Preferably, the ratio of DecylGlucoside to OctylGlucoside is between 1:2 and 2:1, more preferably between 7:5 and 5:7, and most preferably about 6:5.

The inactive ingredients, for example DecylGlucoside (DG) and OctylGlucoside (OG), are effective to stabilize the mixture of the one, two or three biocide substances Applicants believe that the inactive ingredients, such as DG and OG, act as the carrier and disperser to spread the biocide substances mixture effectively.

The inventive formulation preferably results in stabilised micelles in the 5-10 nanometer (nm) range. This allows the germ-killing-liquid-substance (such as the exemplary mixture of 3 biocide substances) to achieve a higher germ-killing efficiency at lower concentrations, than would an unstabilized mixture of the one or more biocide substances.

Accordingly, with respect to the preferred germ-killing-liquid-substance, the combined mixture of the first biocide substance, the second biocide substance, and the disperser, all three acting together, mean that lesser quantities of the first and second biocide substances are required to achieve the same kill-rate of germs on the user's hands, compared to a case if the disperser is not present.

More particularly, the combined mixture of the three active biocide substances, and the disperser, the one or more components interacting and/or acting together, mean that lesser quantities of the included biocide substances are required to achieve the same kill-rate of germs on the user's hands, compared to a case where the disperser was not present.

Without being limited by theory it is believed that, when the germ-killing-liquid-substance reaches the user's hands, the actual biocides do not bond effectively to the user's skin. However, according to the preferred mixture containing the disperser, it is believed that the biocides can effectively bond to the disperser which, in turn, is able to effectively bond to the user's skin. Thus, it is believed that the preferred mixture works because the disperser aids in effectively bonding the biocide to the user's hands.

Advantageously, the apparatus is able to coat the user's hands with a very thin layer of germ-killing-liquid-substance that contains far less active germ-killing agent, than would be the case if the disperser, that is in the germ-killing-liquid-substance, were not used.

Furthermore, in a further modified embodiment, without being limited by theory, a reason as to why far less germ-killing active ingredient is required on the hands is believed to be the result of a synergy between (i) the usage of the three-dimensional filter 410A, and (ii) the preferred presence of the disperser in the modified germ-killing-liquid-substance.

According to the theory, this synergy is a result of the air being cleaner due to the operation of the three-dimensional filter 410A. A consequence of that operation is that fewer germs are blown onto the user's hands from the airflow 200C. Therefore, a smaller amount of germ-killing-liquid-substance is required to be transmitted onto the user's hands. It will be understood by the skilled person that a sufficient amount of the biocide substance is required mostly to focus on killing germs on the user's hands, and since the airflow 200C itself has already been purified inside the apparatus, it is believed that less germs make it onto the user's hands and hence a smaller amount of germ-killing agent is required.

However, it is notionally more difficult to evenly spread such a smaller amount of germ-killing-liquid-substance over the surface of the user's hands. Therefore, an advantage of the disperser is believed to be that it aids in the dispersal of this smaller quantity of substance over the user's skin.

It is further postulated that the synergy also is a result of the faster airflow afforded by the three-dimensional filter 410A. The faster airflow, from the three-dimensional filter 410A, provides more physical force to spread the disperser across the user's hands while the user exposes his hands to the airflow. This may explain why less germ-killing-liquidsubstance is required to sufficiently coat the user's hands with an adequate, thin layer of germ-killing substance.

Moreover, another result of the observed advantageous results of the apparent synergy is that the sufficient coating of the user's hands can be achieved by a shorter burst of spray of the germ-killing-liquid-substance into the airflow 200C.

Furthermore, in the modified embodiment, a smaller amount of active germ-killing-liquid-substance is required. Therefore, in terms of the sensation that the user feels on his hands in practice, the user may feel that his hands have less material coating. Subjectively, this smaller amount of material on the user's hands may cause the user to perceive that his hands feel less sticky after the anti-bacteria material is applied to the hands.

In this specification, the references to airflow are understood to be when the respective embodiments are installed and in operation. It is also understood that an embodiment is capable of generating an airflow, but would not be ready to do so until it is installed and put into operation.

Embodiments of the present invention relates particularly, but not exclusively, to hand dryers and air purifiers, and can be embodied in other apparatus, that involve air-purifying, that draw in air from a human-activity environment, and expel that air purified back into the ambient environment, for example: hair dryers, vacuum cleaners, air fans, air conditioners, refrigerators, vacuum cleaners and clothing tumble dryers, to name a few non-limiting examples. FIG. 18 shows a schematic diagram of an arrangement of use of an embodiment of the three-dimensional filter structure in a vacuum cleaner IC. The vacuum cleaner has a motor and fan 400, 405 that draws an airflow into the apparatus through a pipe 801. The air enters a main collection chamber 800 where the dirt is collected, and then enters into a three-dimensional filter structure in the form of a three-dimensional filter 410C. The filter 410C is in connection with the inlet aperture 101 of the vacuum cleaner via the main collection chamber 800. Thus, the main chamber 800 filters out filters out large particulate, and then the three-dimensional filter 410C is used to remove germs and odours, as per the description of the three-dimensional filter 410A in relation to earlier embodiments. Furthermore, embodiments may have one or more inlet apertures, and one or more outlet apertures. The phrases "an inlet" and "an outlet" includes modifications also may have multiple inlet apertures and/or multiple outlet apertures.

In this specification, the word germ is used as a generic umbrella term that includes both bacteria and viruses.

The embodiments have been advanced by way of example only, and modifications are possible within the scope of the invention as defined by the appended claims.

In this specification, where the words comprise or comprises or derivatives thereof are used in relation to elements, integers, steps or features, this is to indicate that those elements, integers, steps or features are present but it is not to be taken to preclude the possibility of other elements, integers, steps or features being present.

What is claimed is:

1. A human-activity-environment air-purifying apparatus that draws in an airflow from an ambient human-activity-environment, kills germs in the airflow within the apparatus and expels the airflow purified back into the human-activity-environment, the apparatus comprising:
    a housing having an interior chamber into which an airflow enters through an inlet and from which interior chamber the airflow is expelled through an outlet;
    an airflow-germ-killing-system adapted to kill germs in the airflow; and
    an airflow-generator which causes the airflow to flow from the inlet to the outlet;
    wherein the airflow-germ-killing-system includes a three-dimensional filter structure comprising air-filter-surfaces that define a filter interior region therein and encompassed by the air-filter-surfaces of the filter structure, the encompassed filter interior region, in use, positioned in connection with the inlet so that airflow entering the inlet is dispersed into the housing interior chamber in multiple directions exclusively through the air-filter-surfaces of the three-dimensional filter structure; and
    wherein said air-filter-surfaces include top and lateral sides through which the airflow is able to disperse into the housing interior chamber.

2. The apparatus of claim 1 wherein the three-dimensional filter structure is formed as a container or a box with one side fully opened, and wherein the air-filter-surfaces include wall-structure and ceiling-structure.

3. The apparatus of claim 2 wherein the air-filter-surfaces comprise a multi-faceted surface structure having a pleated or corrugated structure.

4. The apparatus of claim 1 wherein the air-filter-surfaces comprise multiple layers of different filter material, and wherein the multiple layers of the air-filter-surfaces comprise a sequence of layers from nearest to the filter interior region to furthest from the filter interior region as follows:
    i) a germ-killing filter layer that carries germ-killing-substance;
    ii) a germ-killing-substance interception filter layer that intercepts or substantially intercepts the germ-killing-substance; and
    iii) a material entrapment layer that entraps at least any filter material that come from said germ-killing filter layer and said germ-killing-substance interception filter layer.

5. The apparatus of claim 4 wherein the germ-killing-substance interception filter layer includes charcoal or carbon.

6. The apparatus of claim 4 wherein the material entrapment layer includes anti-fibre-migration filter material that is able to entrap material that has potential to cause nasal irritation or allergies in humans.

7. The apparatus of claim 1 wherein the airflow-germ-killing-system includes a wick-delivery-system that includes a wick mechanism able to effuse into the airflow within the apparatus a germ-killing-liquid-substance stored in a replaceable container.

8. The apparatus of claim 1 wherein the airflow-germ-killing-system includes a germ-killing-substance-sprayer that sprays germ-killing-liquid-substance into the airflow at a location where, in use, the germ-killing-liquid-substance does not coat onto surfaces of the apparatus itself.

9. The apparatus of claim 1 wherein the filter structure is provided with an external rack, and/or an internal germ-killing-substance positioner, for carrying material to be effused into the airflow.

10. An airflow-germ-killing-system-filter adapted to be used in a human-activity-environment air-purifying apparatus that draws in an airflow from an ambient human-activity-environment, kills germs in the airflow within the apparatus and expels the airflow purified back into the human-activity-environment, the apparatus comprising:

a housing having an interior chamber into which an airflow enters through an inlet and from which interior chamber the airflow is expelled through an outlet;

an airflow-germ-killing-system adapted to kill germs in the airflow; and an airflow-generator which causes the airflow to flow from the inlet to the outlet;

wherein the airflow-germ-killing-system-filter comprises a three-dimensional filter structure having air-filter-surfaces that define a filter interior region therein and encompassed by the air-filter-surfaces of the filter structure, the encompassed filter interior region, in use, positioned in connection with the inlet so that airflow entering the inlet is dispersed into the interior chamber in multiple directions exclusively through the air-filter-surfaces of the three-dimensional filter structure; and wherein said air-filter-surfaces include top and lateral sides through which the airflow is able to disperse into the housing interior chamber.

11. The filter of claim 10 wherein the three-dimensional filter structure is formed as a container or a box with one side fully opened.

12. The filter of claim 10 wherein the air-filter-surfaces comprise a multi-faceted surface structure having a pleated or corrugated structure.

13. The filter of claim 10 wherein the air-filter-surfaces comprise multiple layers of different filter material, and wherein the multiple layers of the air-filter-surfaces comprise a sequence of layers from nearest to the filter interior region to furthest from the filter interior region as follows:

i) a germ-killing filter layer that carries germ-killing-substance; and ii) a germ-killing-substance interception filter layer that intercepts or substantially intercepts the germ-killing-substance.

14. The filter of claim 13 wherein said sequence of layers from nearest to the filter interior region to furthest from the filter interior region comprises:

i) said germ-killing filter layer that carries germ-killing-substance; and ii) said germ-killing-substance interception filter layer that intercepts or substantially intercepts the germ-killing-substance, and iii) a material entrapment layer that entraps at least any filter material that come from said germ-killing filter layer and said germ-killing-substance interception filter layer.

15. The filter of claim 14 wherein the germ-killing-substance interception filter layer includes charcoal or carbon.

16. The filter of claim 14 wherein the material entrapment layer includes anti-fibre-migration filter material that is able to entrap material that has potential to cause nasal irritation or allergies in humans.

17. The filter of claim 10 wherein the filter structure is provided with an external rack, and/or an internal germ-killing-substance positioner, for carrying material to be effused into the airflow.

* * * * *